(12) United States Patent
Neville

(10) Patent No.: US 8,538,778 B2
(45) Date of Patent: Sep. 17, 2013

(54) METHODS AND SYSTEMS FOR INTEGRATED HEALTH SYSTEMS

(75) Inventor: Thomas Neville, Incline Village, NV (US)

(73) Assignee: Soar BioDynamics, Ltd., Incline Village, NV (US)

( * ) Notice: Subject to any disclaimer, the term of this patent is extended or adjusted under 35 U.S.C. 154(b) by 477 days.

(21) Appl. No.: 12/466,684

(22) Filed: May 15, 2009

(65) Prior Publication Data

US 2010/0049546 A1  Feb. 25, 2010

Related U.S. Application Data

(60) Provisional application No. 61/053,600, filed on May 15, 2008.

(51) Int. Cl.
*G06Q 50/00* (2012.01)

(52) U.S. Cl.
USPC .................................. 705/3; 705/2

(58) Field of Classification Search
USPC ........................................ 705/2, 3
See application file for complete search history.

(56) References Cited

U.S. PATENT DOCUMENTS

| | | | |
|---|---|---|---|
| 5,501,983 A | 3/1996 | Lilja et al. | |
| 5,594,638 A | 1/1997 | Iliff | |
| 5,660,176 A | 8/1997 | Iliff | |
| 5,937,387 A | 8/1999 | Summerell et al. | |
| 5,989,811 A * | 11/1999 | Veltri et al. | 435/6.14 |
| 6,108,635 A | 8/2000 | Herren et al. | |
| 6,423,503 B1 | 7/2002 | Mikolajczyk et al. | |
| 6,807,531 B1 | 10/2004 | Kanai | |
| 6,871,171 B1 | 3/2005 | Agur et al. | |
| 7,211,397 B2 | 5/2007 | Mikolajczyk et al. | |
| 7,467,119 B2 | 12/2008 | Saidi et al. | |
| 7,593,913 B2 | 9/2009 | Wang et al. | |
| 2003/0101075 A1 | 5/2003 | Ban et al. | |
| 2003/0133903 A1 | 7/2003 | Dang et al. | |
| 2004/0044546 A1 * | 3/2004 | Moore | 705/2 |

(Continued)

FOREIGN PATENT DOCUMENTS

| | | |
|---|---|---|
| EP | 1399868 | 12/2002 |
| EP | 1842139 | 8/2006 |

(Continued)

OTHER PUBLICATIONS

Carter, H.B. et al., "Detection of life-threatening prostate cancer with prostate-specific antigen velocity during a window of curability," Journal of the National Cancer Institute 98(21):1521-1527 (2006).

(Continued)

*Primary Examiner* — Robert Morgan
*Assistant Examiner* — Charles P Coleman
(74) *Attorney, Agent, or Firm* — Wilson Sonsini Goodrich & Rosati

(57) ABSTRACT

Methods, business methods, and systems are provided herein for integrated healthcare. As the amount of medical information increases rapidly, including information from multiple biomarkers, analysis and management of that information becomes more and more important to extract meaningful conclusions from the information. Statistical and computational methods are described herein that have been created for the methods and systems for integrated healthcare. For example, a computer system is described extracts significance over time of PSA and fPSA biomarker tests for prostate health.

50 Claims, 54 Drawing Sheets

(56) References Cited

U.S. PATENT DOCUMENTS

| | | |
|---|---|---|
| 2004/0087635 A1 | 5/2004 | Hammarsten |
| 2004/0092807 A1 | 5/2004 | Breskin et al. |
| 2004/0172225 A1 | 9/2004 | Hochberg et al. |
| 2004/0243362 A1 | 12/2004 | Liebman |
| 2005/0165285 A1 | 7/2005 | Iliff |
| 2005/0282199 A1 | 12/2005 | Slawin et al. |
| 2006/0051836 A1 | 3/2006 | Tang et al. |
| 2006/0088894 A1 | 4/2006 | Wright et al. |
| 2006/0218010 A1 | 9/2006 | Michon et al. |
| 2006/0269921 A1 | 11/2006 | Segara et al. |
| 2007/0005257 A1 | 1/2007 | Cheng et al. |
| 2008/0033253 A1 | 2/2008 | Neville |
| 2008/0045811 A1 | 2/2008 | Iliff |
| 2008/0228043 A1 | 9/2008 | Kenedy et al. |
| 2008/0228735 A1 | 9/2008 | Kenedy et al. |
| 2009/0006133 A1 | 1/2009 | Weinert et al. |
| 2009/0047694 A1 | 2/2009 | Shuber |
| 2009/0054740 A1* | 2/2009 | Gudmundsson et al. ..... 600/300 |
| 2009/0062624 A1* | 3/2009 | Neville .......................... 600/300 |
| 2009/0087860 A1 | 4/2009 | Todd et al. |
| 2009/0088981 A1 | 4/2009 | Neville |
| 2009/0187420 A1 | 7/2009 | Hancock et al. |
| 2010/0168621 A1 | 7/2010 | Neville |
| 2012/0259555 A1 | 10/2012 | Neville |

FOREIGN PATENT DOCUMENTS

| | | |
|---|---|---|
| EP | 1939777 | 7/2008 |
| WO | WO-02-09568 A1 | 2/2002 |
| WO | WO-2005-119582 A2 | 12/2005 |
| WO | WO-2007-035766 A2 | 3/2007 |
| WO | WO-2007-123914 | 11/2007 |
| WO | WO-2008-109797 A1 | 9/2008 |
| WO | WO-2009-050643 A1 | 4/2009 |

OTHER PUBLICATIONS

D'Amico, A.V. et al., "Preoperative PSA velocity and the risk of death from prostate cancer after radical prostatectomy," N Engl J Med 351(2):125-35 (2004).

Efstathiou, J.A. et al., "Prostate-specific antigen-based serial screening may decrease prostate cancer-specific mortality," Urology 68(2):342-7 (2006).

Han, M. et al., "Biochemical (prostate specific antigen) recurrence probability following radical prostatectomy for clinically localized prostate cancer," J Urol 169(2):517-23 (2003).

Kaplan, S.A. et al., "Combination therapy with doxazosin and finasteride for benign prostatic hyperplasia in patients with lower urinary tract symptoms and a baseline total prostate volume of 25 ml or greater," J Urol 175 (1): 217-20 (2006).

Martin, N.E. et al., "The influence of serial prostate-specific antigen (PSA) screening on the PSA velocity at diagnosis," Cancer 113(4):717-22 (2008).

Mochtar, C.A. et al., "Prostate-Specific Antigen as an Estimator of Prostate Volume in the Management of Patients with Symptomatic Benign Prostatic Hyperplasia," European Urology44:695-700 (2003).

Mochtar, CA et al., "Prognostic role of prostate-specific antigen and prostate volume for the risk of invasive therapy in patients with benign prostatic hyperplasia initially managed with alpha1-blockers and watchful waiting," Urology. Feb. 2005; 65(2): 300-5.

Mochtar, CA et al., "PSA velocity in conservatively managed BPH: can it predict the need for BPH-related invasive therapy?" Prostate. Sep. 15, 2006;66(13):1407-12.

Ng, M.K. et al., "Prostate-specific antigen (PSA) kinetics in untreated, localized prostate cancer: PSA velocity vs PSA doubling time," BJU Int (Oct. 16, 2008).

O'Brien, M.F. et al., "Pretreatment prostate-specific antigen (PSA) velocity and doubling time are associated with outcome but neither improves prediction of outcome beyond pretreatment PSA alone in patients treated with radical prostatectomy," J Clin Oncol 27(22):3591-7 (2009).

Stephenson, A.J. et al., "Prostate cancer-specific mortality after radical prostatectomy for patients treated in the prostate-specific antigen era," J Clin Oncol 27(26):4300-5 (2009).

Stephenson, A.J. et al., "Preoperative nomogram predicting the 10-year probability of prostate cancer recurrence after radical prostatectomy," J Natl Cancer Inst 98(10):715-7 (2006).

Vickers, A.J. et al., "Prostate-Specific Antigen Velocity for Early Detection of Prostate Cancer: Result from a Large, Representative, Population-based Cohort," Eur Urol (Aug. 7, 2009).

U.S. Appl. No. 11/431,248, filed May 9, 2006.
U.S. Appl. No. 11/431,119, filed May 9, 2006.
U.S. Appl. No. 11/431,157, filed May 9, 2006.
U.S. Appl. No. 11/431,156, filed May 9, 2006.
U.S. Appl. No. 60/914,125, filed Apr. 26 2007.

International search report dated Jan. 18, 2010 for PCT Application No. US2009/44246.

D'Amico, et al. Identifying patients at risk for significant versus clinically insignificant postoperative prostate-specific antigen failure. J Clin Oncol. Aug. 1, 2005;23(22):4975-9.

International search report dated Apr. 22, 2010 for PCT Application No. US2009/069302.

Brant, et al. Screening for prostate cancer by using random-effects models. J. R. Statist. Soc. A (2003) 166, Part 1, pp. 51-62.

Gaynor, et al. On the use of cause-specific failure and conditional. Journal of the American Statistical Association. 1993; 88(422):400-409.

Kwiatkowski, et al. In prostatism patients the ratio of human glandular kallikrein to free PSA improves the discrimination between prostate cancer and benign hyperplasia within the diagnostic "gray zone" of total PSA 4 to 10 ng/mL. Urology. Sep. 1998;52(3):360-5.

Dutkiewicz, et al. Serum PSA levels at 6 month after surgery, TURP or Doxazosin therapy for BPH. Dutkiewicz et al. Database Medline AN 1997243195. Mater Med Pol. Apr.-Jun. 1996;28(2):69-70. (abstract only).

Fitzpatrick, et al. PSA measurement in the treatment of BPH. BJU Int. Mar. 2004;93 Suppl 1:2-4.

Hara, et al. Application of serum PSA to identify acute bacterial prostatitis in patients with fever of unknown origin or symptoms of acute pyelonephritis. Prostate. Sep. 1, 2004;60(4):282-8.

Stoltzfus, JC. Logistic regression: a brief primer. Acad Emerg Med. Oct. 2011;18(10):1099-104. doi: 10.1111/j.1553-2712.2011.01185. x.

Wang, et al. Effects of antibiotic and anti-inflammatory treatment on serum PSA and free PSA levels in patients with chronic prostatitis IIIA. Database Medline, AN 2006579735 (National Journal of Andrology, 2006, vol. 12, No. 9, pp. 787-790), Zhonghua Nan Ke Xue. Sep. 2006;12(9):787-90. (abstract only).

Boddy, et al. Intra-individual variation of serum prostate specific antigen levels in men with benign prostate biopsies. BJU Int. Apr. 2004;93(6):735-8.

Bruun, et al. Assessment of intra-individual variation in prostate-specific antigen levels in a biennial randomized prostate cancer screening program in Sweden. Prostate. Nov. 1, 2005;65(3):216-21.

Kobayashi, et al. Intraindividual variation in total and percent free prostate-specific antigen levels in prostate cancer suspects. Urol Int. 2005;74(3):198-202.

Komatsu, et al. Physiologic (intraindividual) variation of serum prostate-specific antigen in 814 men from a screening population. Urology. Mar. 1996;47(3):343-6.

Lujan, et al. Prostate specific antigen variation in patients without clinically evident prostate cancer. J Urol. Oct. 1999;162(4):1311-3.

Morote, et al. Intraindividual variations of total and percent free serum prostatic-specific antigen levels in patients with normal digital rectal examination. Eur Urol. Aug. 1999;36(2):111-5.

Nixon, et al. Day to day changes in free and total PSA: significance of biological variation. Prostate Cancer Prostatic Dis. Dec. 1997;1(2):90-96.

Yan. Intraindividual variation of prostate specific antigen measurement and implications for early detection of prostate carcinoma. Cancer. Aug. 15, 2001;92(4):776-80.

Bartsch, et al. Tyrol Prostate Cancer Demonstration Project: early detection, treatment, outcome, incidence and mortality. BJU Int. Apr. 2008;101(7):809-16.

Carter, et al. Longitudinal evaluation of prostate-specific antigen levels in men with and without prostate disease. JAMA. Apr. 22-29, 1992;267(16):2215-20.

Carter, et al. Prostate-specific antigen velocity risk count assessment: a new concept for detection of life-threatening prostate cancer during window of curability. Urology. Oct. 2007;70(4):685-90.

Carter, et al. PSA velocity for the diagnosis of early prostate cancer. A new concept. Urol Clin North Am. Nov. 1993;20(4):665-70.

Fang, et al. Low levels of prostate-specific antigen predict long-term risk of prostate cancer: results from the Baltimore Longitudinal Study of Aging. Urology. Sep. 2001;58(3):411-6.

Freedland, et al. Risk of prostate cancer-specific mortality following biochemical recurrence after radical prostatectomy. JAMA. Jul. 27, 2005;294(4):433-9.

Freedland, et al. Time to prostate specific antigen recurrence after radical prostatectomy and risk of prostate cancer specific mortality. J Urol. Oct. 2006;176(4 Pt 1):1404-8.

Loeb, et al. PSA doubling time versus PSA velocity to predict high-risk prostate cancer: data from the Baltimore Longitudinal Study of Aging. Eur Urol. Nov. 2008;54(5):1073-80. Epub Jul. 2, 2008.

Partin, et al. Evaluation of serum prostate-specific antigen velocity after radical prostatectomy to distinguish local recurrence from distant metastases. Urology. May 1994;43(5):649-59.

Pearson, et al. Longitudinal analysis of serial measurements of free and total PSA among men with and without prostatic cancer. Urology. Dec. 1996;48(6A Suppl):4-9.

Pearson, et al. Mixed-effects regression models for studying the natural history of prostate disease. Stat Med. Mar. 15-Apr. 15, 1994;13(5-7):587-601.

Schroder, et al. Early detection of prostate cancer in 2007. Part 1: PSA and PSA kinetics. Eur Urol. Mar. 2008;53(3):468-77. Epub Nov. 5, 2007.

Thiel, et al. Role of prostate-specific antigen velocity in prediction of final pathologic stage in men with localized prostate cancer. Urology. May 1997;49(5):716-20.

U.S. Appl. No. 13/429,641, filed Mar. 26, 2012, Neville.

U.S. Appl. No. 13/454,058, filed Apr. 23, 2012, Neville et al.

* cited by examiner

Bayes Probability of Other Conds
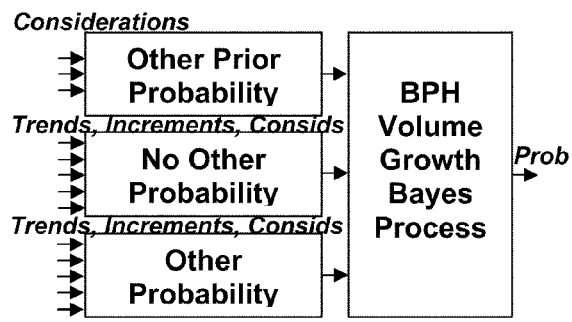
Bayes Probability of Inflammation
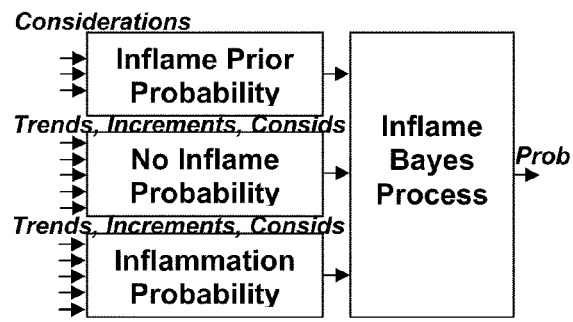
Bayes Probability of Infection
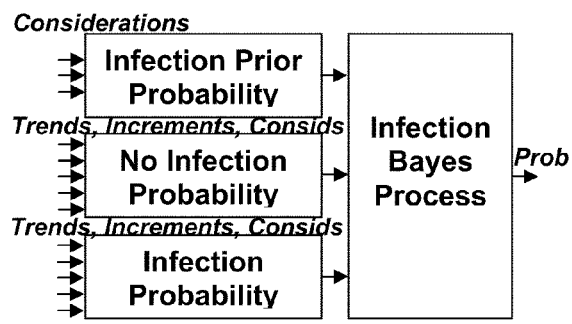
FIG. 35

Partition of the Prostate into Condition Combinations

Definitions of Conditions
 O = Other Conditions
 I = Inflammation Prostatitis
 *I* = Infection Prostatitis Partitions – Condition Combinations
 O, I, *I*         (1 condition)
 OI, O*I*, I*I*   (2 conditions)
 OI*I*            (3 conditions)

Probability Generators for Monte Carlo Iterations for Bayes Process
O – Other
I – Inflammation
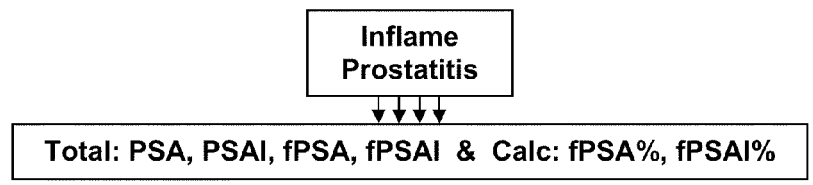
***I* – Infection**
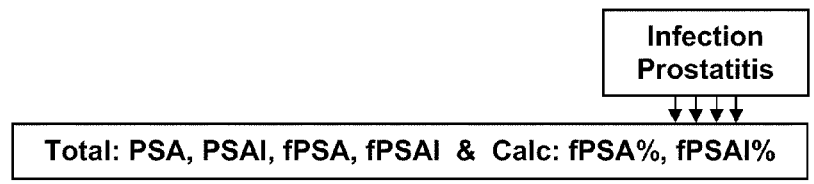
FIG. 37

Probability Generators for Monte Carlo Iterations for Bayes Process
OI – Other, Inflammation
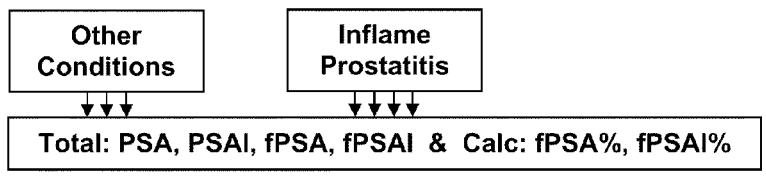
OII – Other, Infection
II – Inflammation, Infection
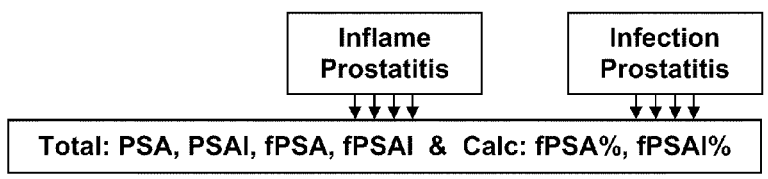
OII – Other, Inflammation, Infection
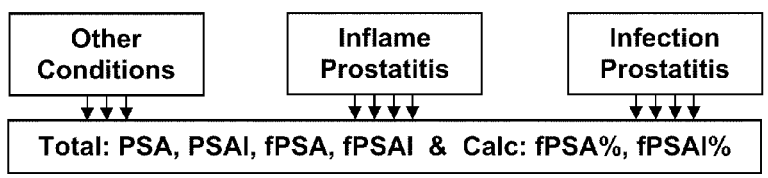
FIG. 38

Distributions for Other Conditions Probability Generators

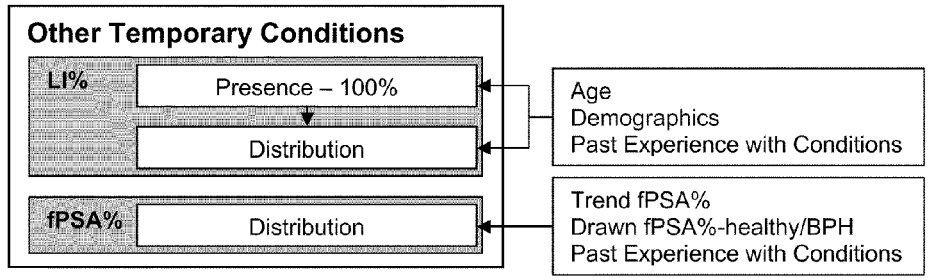

Example Free PSA % Distribution

Free PSA % Distribution = Normal Distribution (Mean, Standard Deviation)
Mean = Other% * Trend fPSA%
SD   = CV% * Mean

Distributions for Inflammation Prostatitis Probability Generators

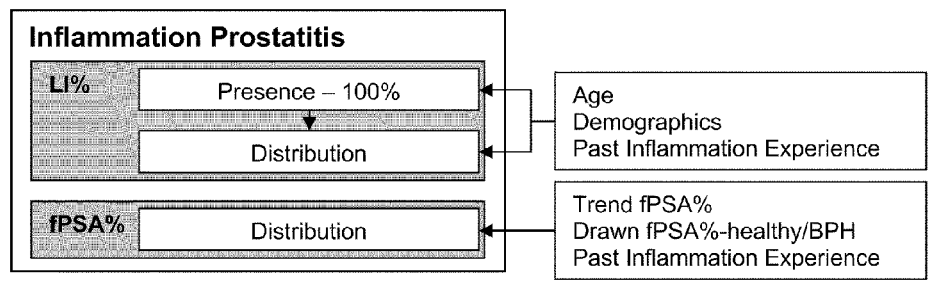

Example Free PSA % Distribution

Free PSA % Distribution = Normal Distribution (Mean, Standard Deviation)
Mean = Inflammation% * Trend fPSA%
SD   = CV% * Mean

Distributions for Infection Prostatitis Probability Generators

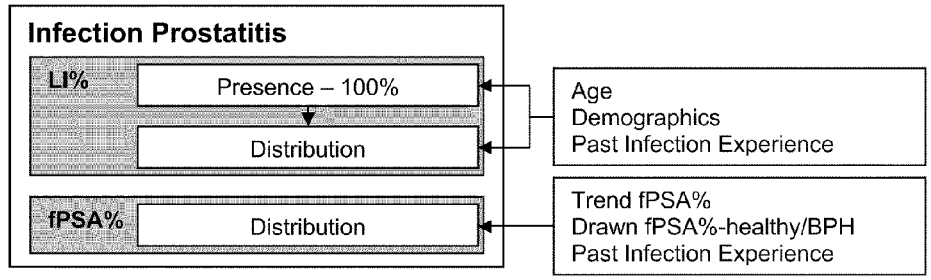

Example Free PSA % Distribution

Free PSA % Distribution = Normal Distribution (Mean, Standard Deviation)
Mean = Infection% * Trend fPSA%
SD   = CV% * Mean

FIG. 41

Bayes Process for Four Prostate Conditions
Bayes Probability of BPH Volume
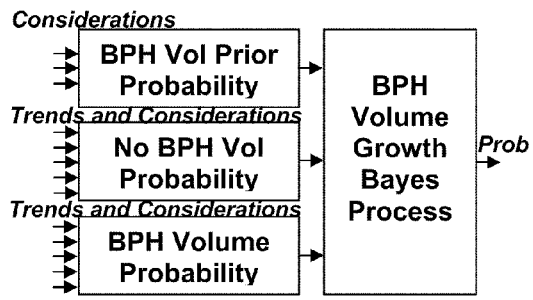
Bayes Probability of Inflammation
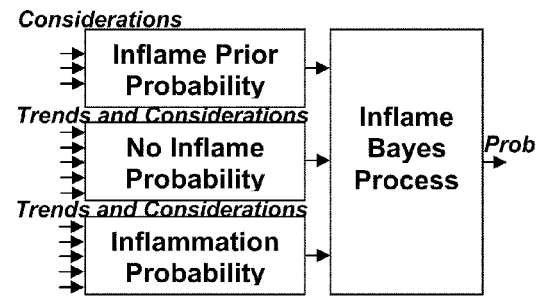
Bayes Probability of Infection
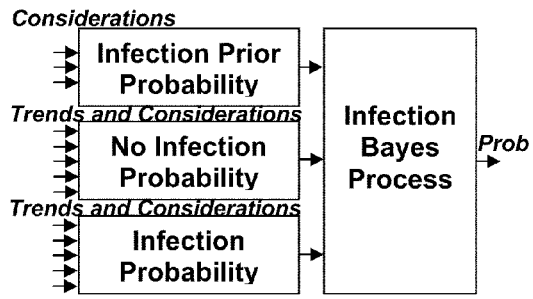
Bayes Probability of Cancer
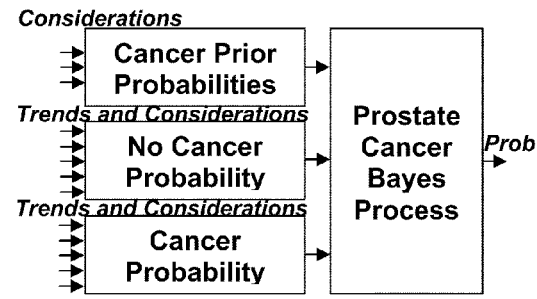
FIG. 46

Partition of the Prostate into Condition Combinations

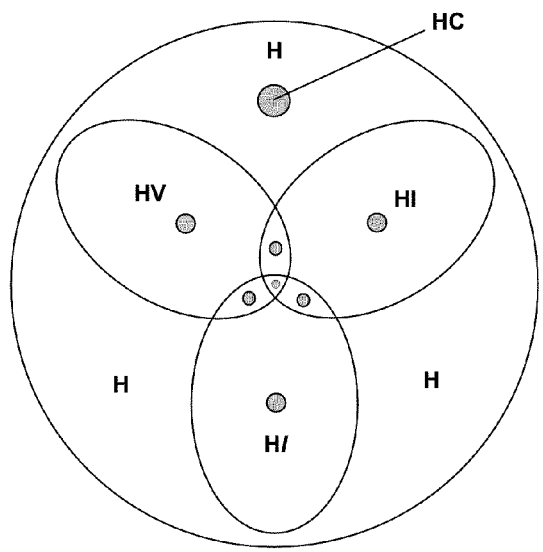

Definitions of Conditions
H = Healthy Prostate
V = Volume Growth Due to BPH
I = Inflammation Prostatitis
*I* = Infection Prostatitis
C = Progressing Prostate Cancer

Partitions – Condition Combinations
H                                    (1 condition)
HV, HI, H*I*, HC                     (2 conditions)
HVI, HV*I*, HVC, HI*I*, HIC, H*I*C   (3 conditions)
HVI*I*, HVIC, HV*I*C, HI*I*C         (4 conditions)
HVI*I*C                              (5 conditions)

FIG. 47

Probability Generators for Monte Carlo Iterations for Bayes Process
H – Healthy
HV – Healthy, Volume
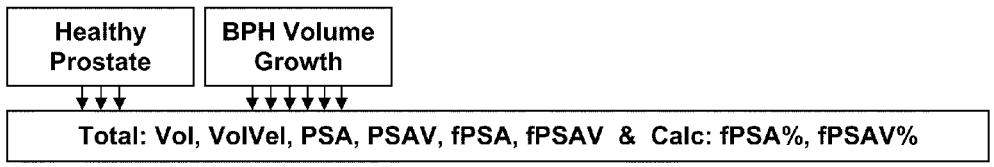
HI – Healthy, Inflammation
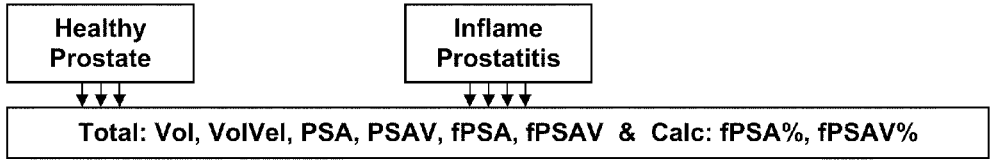
H/ – Healthy, Infection
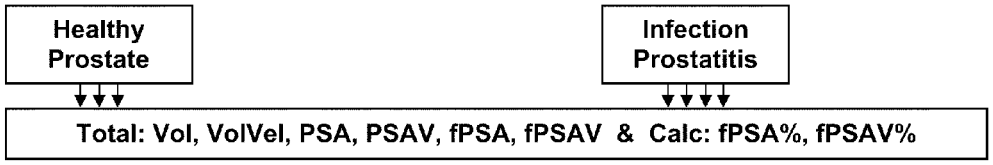
HC – Healthy, Cancer
FIG. 48

Probability Generators for Monte Carlo Iterations for Bayes Process
HVI – Healthy, Volume, Inflammation
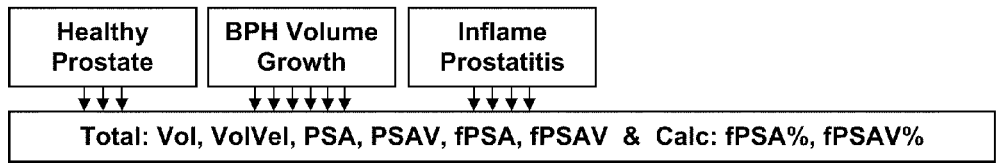
HV*I* – Healthy, Volume, Infection
HVC – Healthy, Volume, Cancer
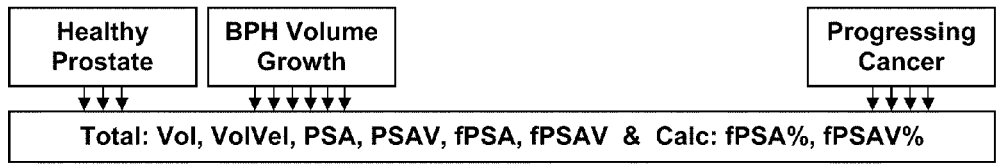
H*II* – Healthy, Inflammation, Infection
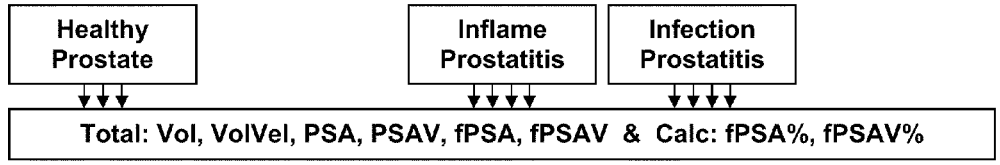
HIC – Healthy, Inflammation, Cancer
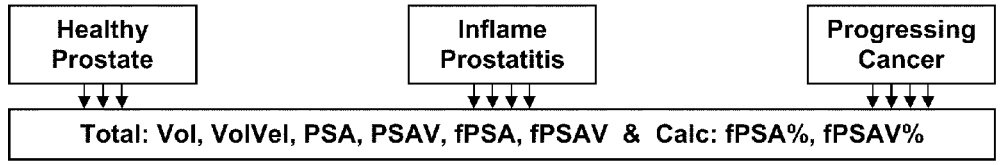
H*I*C – Healthy, Infection, Cancer
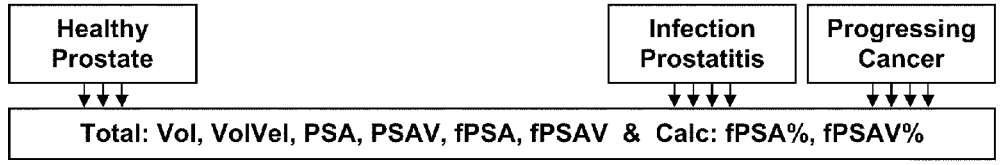
FIG. 49

Probability Generators for Monte Carlo Iterations for Bayes Process
HVI*I* – Healthy, Volume, Inflammation, Infection
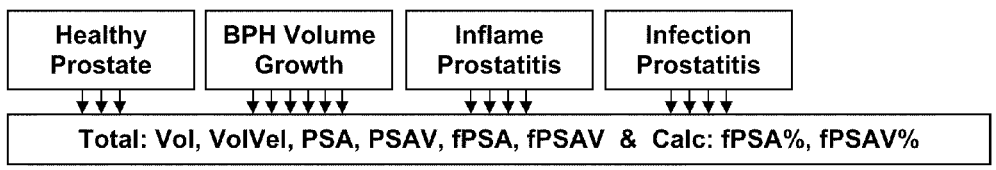
HVIC – Healthy, Volume, Inflammation, Cancer
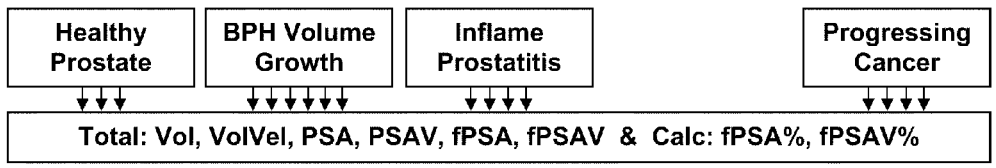
HV*I*C – Healthy, Volume, Infection, Cancer
HI*I*C – Healthy, Inflammation, Infection, Cancer
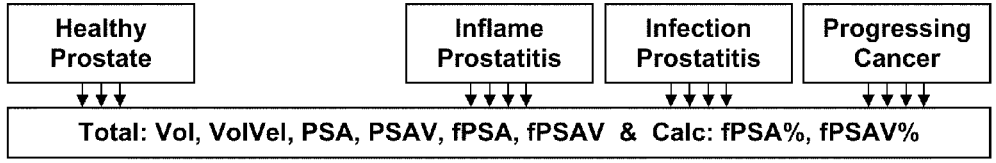
HVI*I*C – Healthy, Volume, Inflammation, Infection, Cancer
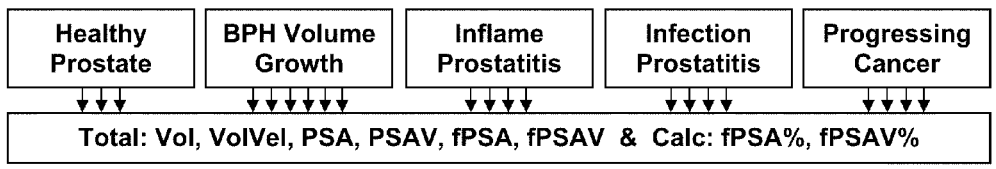
FIG. 50

Distributions for Healthy Prostate Probability Generator

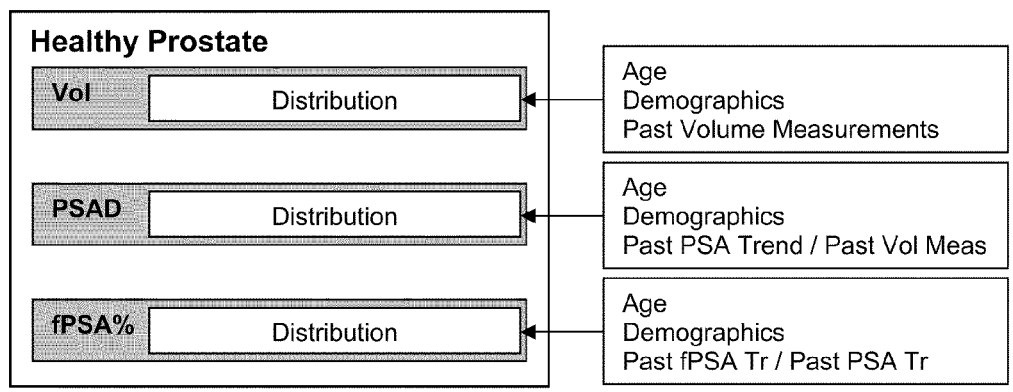

Example Healthy Prostate Volume Distribution

PSAD Distribution = Normal Distribution (Mean, Standard Deviation)
        Mean = 28.0
        SD   = 4.3

Example PSA Density Distribution

PSAD Distribution = Normal Distribution (Mean, Standard Deviation)
        Mean = 0.035
        SD   = 0.008

Example Free PSA % Distribution

Free PSA % Distribution = Normal Distribution (Mean, Standard Deviation)
        Mean = 28%
        SD   = 7%

FIG. 53

Distributions for BPH Volume Growth Probability Generators

Example PSA Density Distribution

PSAD Distribution = Normal Distribution (Mean, Standard Deviation)
 Mean = BPH% * Drawn Healthy PSAD
 SD   = CV% * Mean

Example Free PSA % Distribution

Free PSA % Distribution = Normal Distribution (Mean, Standard Deviation)
 Mean = BPH% * Drawn Healthy fPSA%
 SD   = CV% * Mean

Distributions for Inflammation Prostatitis Probability Generators

Example Free PSA % Distribution

Free PSA % Distribution = Normal Distribution (Mean, Standard Deviation)
  Mean = Inflammation% * Sum Health/BPH fPSA / Sum Health/BPH PSA
  SD   = CV% * Mean

Distributions for Infection Prostatitis Probability Generators

Example Free PSA % Distribution

Free PSA % Distribution = Normal Distribution (Mean, Standard Deviation)
  Mean = Infection% * Sum Health/BPH fPSA / Sum Health/BPH PSA
  SD   = CV% * Mean

METHODS AND SYSTEMS FOR INTEGRATED HEALTH SYSTEMS

CROSS-REFERENCE

This application claims the benefit of U.S. Provisional Application No. 61/053,600, filed May 15, 2008, which application is incorporated herein by reference.

BACKGROUND OF THE INVENTION

There is increasing emphasis on disease prevention, early detection and treatment, avoiding unnecessary treatment, timing of treatments, avoiding invasive procedures, and reducing costs. Significant investments are being made to accelerate discovery and use of biomarkers that effectively detect progressing cancer. However, assaying or testing for an individual biomarker is often not effective for detection of progressing cancer.

The use of screening blood tests, where multiple markers are tested, is becoming more prevalent and cost-effective. Screening for many conditions using blood from a single draw can reduce medical costs. The incremental cost of additional tests decreases if subsequent blood draws are not needed. A further means of reducing costs is to store blood for later testing if needed. New technology is also reducing the cost of specific tests.

There is a need in the art to extract additional information from a diagnostic test, whether it is a biomarker test or a series of biomarker tests, or a medical image. Novel methods and systems of extracting additional quantitative information for use by patients or physicians are increasingly desirable to reduce the cost of medical diagnostics and treatments and to improve the accuracy of diagnosis and efficacy of treatments.

SUMMARY OF THE INVENTION

In an aspect, a method is disclosed of performing a course of medical action for a medical condition of a subject comprising: obtaining a first value of at least one biomarker from a subject; sending said first value to a computer system that calculates a first plurality of posterior probabilities of the occurrence of a plurality of medical conditions of said subject using said first value, wherein said plurality of medical conditions comprises at least a first and second medical condition; receiving said first plurality of posterior probabilities; performing a first course of medical action for the first medical condition based on said first plurality of posterior probabilities; observing a result of said first course of medical action; obtaining a second value of at least one biomarker from said subject; sending said second value and said result of said first course of the medical action to said computer system that calculates a second plurality of posterior probabilities of the occurrence of said plurality of medical conditions of said subject, wherein said calculation uses said at second value and said result; receiving said second plurality of posterior probabilities; and performing a second course of medical action for the second medical condition based on said second plurality of posterior probabilities.

In an embodiment, the first or second value is a PSA value or fPSA value. In another embodiment, the subject is a human, for example a patient.

In an embodiment, a computer system comprises a device for network communication, a storage unit, and a processor. The computer system can comprise a Monte Carlo engine.

In an embodiment, sending comprises entering said first and second values into a webpage or using a device that transmits either or both of said first and second values to said computer system through a wireless network.

In an embodiment, first and second values are a first and second biomarker trend of biomarker values over a period of time. A computer system can calculate each of said first plurality of posterior probabilities by relating: a prior probability of a medical condition; a probability of observing said first biomarker trend for an individual with said medical condition; and a probability of observing said first biomarker trend for an individual without said medical condition. A computer system can calculate each of said second plurality of posterior probabilities by relating: a prior probability of a medical condition, wherein said prior probability was calculated using subject information comprising said result of a course of medical action; a probability of observing said second biomarker trend for an individual with said medical condition; and a probability of observing said second biomarker trend for an individual without said medical condition.

In an embodiment, a plurality of medical conditions are prostate medical conditions, for example they can be selected from the group consisting of the following: prostatitis due to inflammation, prostatitis due to infection, prostate cancer, benign prostate hyperplasia, and no prostate disease.

In an embodiment, receiving comprises viewing a display of said posterior probabilities, for example a display on an output device. An output device can be selected from the group consisting of the following: a computer, a webpage, an electronic medical record, a printout, and a personal electronic device.

In an embodiment, a first or second course of medical action is delivering medical treatment to said subject, such as a medical treatment is selected from a group consisting of the following: a pharmaceutical, surgery, organ resection, and radiation therapy. In an embodiment, a pharmaceutical comprises a chemotherapeutic compound for cancer therapy. In another embodiment, the first or second course of medical action comprises administration of medical tests or medical imaging of said subject or setting a specific time for delivering medical treatment or a biopsy or a consultation with a medical professional.

In another aspect, a business method is disclosed that comprises: receiving a first value of at least one biomarker of a subject; calculating a first plurality of posterior probabilities of the occurrence of a plurality of medical conditions of said subject with a computer system using said a first value; delivering said first plurality of posterior probabilities to a user; receiving a second value of at least one biomarker of a subject and a result of a course of medical action taken by said user based upon said delivery of said first plurality of posterior probabilities; calculating a second plurality of posterior probabilities of the occurrence of a plurality of medical conditions of said subject with said computer system using said a second value and said result of a course of the medical action; and delivering said second plurality of posterior probabilities to said user. In an embodiment, the first or second values are received from a user, such as a user selected from the group consisting of the following: a physician, a health care provider, a pharmacy, an insurance company, and the subject. A first or second value can also be received from said user through a webpage or an electronic device or an assay device.

In another embodiment, the first or second values are received from a device, such as a device selected from the group consisting of the following: a lab test device, a point-of-care assay device, a personal electronic device, an electronic medical record, and a computer system.

Calculating can be carried out by a Monte Carlo engine and can be a Bayesian statistical calculation.

In an embodiment, a plurality of medical conditions is at least four medical conditions, for example from the group consisting of: prostatitis due to inflammation, prostatitis due to infection, prostate cancer, benign prostate hyperplasia, and no prostate disease. A biomarker value can be from a PSA or fPSA assay.

A result of a course of medical action can be selected from the group consisting of the following: a test result, a diagnosis, a cure, an effect, and no effect. Posterior probabilities can be delivered to a user through an electronic medical record or a webpage or an electronic device with a display or a printout.

In an embodiment, the computer system comprises a processor, a storage unit, and a device for network communication.

In an embodiment, a business method is carried out for a fee, for example each delivery of posterior probabilities is carried out for a fee.

A business method can further comprise suggesting a course of medical action to said user based on said posterior probabilities, and the suggestion can be provided for a fee.

In an aspect of the invention, a method of delivering a probability that a subject has a medical condition to a user comprises: calculating a plurality of posterior probabilities of the occurrence of a plurality of medical conditions of a subject having a biomarker trend, wherein said biomarker trend comprises biomarker values from said subject at more than one time, and wherein each of said plurality of posterior probabilities is calculated by relating: a prior probability of the occurrence of each of said plurality of medical conditions; and a probability of observing said biomarker trend for an individual with each medical condition; and a probability of observing said biomarker trend for an individual without each medical condition; and delivering said plurality of probabilities of said plurality of medical conditions to a user with an output device.

In another aspect, a method of delivering a probability that a subject has a medical condition to a user comprises: calculating a plurality of posterior probabilities of the occurrence of a plurality of medical conditions of a subject having a result of a course of medical action and having a biomarker trend, wherein said biomarker trend comprises biomarker values from said subject at more than one time, and wherein each of said plurality of posterior probabilities is calculated by relating: a prior probability of the occurrence of each of said plurality of medical conditions, wherein said prior probability was calculated using subject information comprising said result of a course of medical action; a probability of said biomarker trend for an individual with each medical condition; and a probability of said biomarker trend for an individual without each medical condition; and delivering said plurality of probabilities of said plurality of medical conditions to a user with an output device. A biomarker trend can be a PSA trend or fPSA trend.

In an embodiment, an output device is selected from the group consisting of the following: a computer, a webpage, an electronic medical record, a printout, and a personal electronic device.

A course of medical action can be delivering medical treatment to said subject, for example a medical treatment selected from a group consisting of the following: a pharmaceutical, surgery, organ resection, and radiation therapy.

The course of medical action can also comprise administration of medical tests, medical imaging of said subject, setting a specific time for delivering medical treatment, a biopsy, and/or consultation with a medical professional.

In yet another aspect, a method of delivering a probability that a subject has a medical condition to a user is disclosed comprising: calculating a plurality of posterior probabilities of the occurrence of a plurality of prostate medical conditions of a subject having a PSA value and an fPSA value, each at more than one time thereby having a PSA trend and an fPSA trend, wherein each of said plurality of posterior probabilities is calculated by relating: a prior probability of a prostate medical condition; and a probability of observing said PSA trend and said fPSA trend for an individual with said prostate medical condition; and a probability of observing said PSA trend and said fPSA trend for an individual without said prostate medical condition; and delivering said plurality of probabilities of said plurality of medical conditions to a user with an output device. In an embodiment, a method can further comprise: calculating a second plurality of posterior probabilities of the occurrence of said plurality of prostate medical conditions of a subject having a result of a course of medical action and having a new PSA value and a new fPSA value, each at more than one time thereby having a second PSA trend and a second fPSA trend, wherein each of said plurality of posterior probabilities is calculated by relating: a prior probability of a prostate medical condition, wherein said prior probability was calculated using subject information comprising said result of a course of medical action; and a probability of observing said second PSA trend and said second fPSA trend for an individual with said prostate medical condition; and a probability of observing said second PSA trend and said second fPSA trend for an individual without said prostate medical condition; and delivering said second plurality of probabilities of said plurality of medical conditions to the user with an output device.

INCORPORATION BY REFERENCE

All publications mentioned in this specification are herein incorporated by reference to the same extent as if each individual publication was specifically and individually indicated to be incorporated by reference.

BRIEF DESCRIPTION OF THE DRAWINGS

Many features of the invention are set forth with particularity in the appended claims. A better understanding of the features and advantages of the invention will be obtained by reference to the following detailed description that sets forth illustrative embodiments, in which many of the invention are utilized, and the accompanying drawings of which:

FIG. 35 illustrates that prior probabilities may be a function of age, race, genetics, demographics, past experience with the conditions and other considerations.

FIG. 37 and FIG. 38 demonstrate a probability generator for all temporary prostate conditions consolidates output from three separate probability generators: inflammation prostatitis, infection prostatitis and other temporary conditions.

FIG. 41 shows an embodiment of other clinical conditions PSA increment is the product of the other conditions leak rate increment, drawn from the other conditions LI % distribution, and trend PSA from the PSA module.

FIG. 46 shows an embodiment of how four similar Bayes processes are used to calculate the probability of the prostate conditions: volume growth due to BPH, inflammation prostatitis, infection prostatitis and progressing cancer.

FIG. 47 shows the status of the prostate is partitioned into 16 different condition combinations that are composed of five different prostate conditions.

FIG. 48, FIG. 49, and FIG. 50 show an aspect of the invention, a probability generator for all prostate conditions consolidates output from five exemplary separate probability generators for a healthy prostate and the four prostate that include without limitation: volume growth due to BPH, inflammation prostatitis, infection prostatitis and progressing cancer.

FIG. 51 shows the probability distributions of each prostate condition can be affected by past experience and the results of imaging, tests, treatment and other medical procedures as shown in.

FIG. 53 shows an embodiment of a healthy prostate module that has three distributions for Monte Carlo draws: Vol, PSAD and fPSA %.

DETAILED DESCRIPTION OF THE INVENTION

Methods, business methods, and systems are provided herein for integrated healthcare. As the amount of medical information increases rapidly, including information from multiple biomarkers, analysis and management of that information becomes more and more important to extract meaningful conclusions from the information. Methods and systems, as described herein, provide calculations of biomarker values into useful analytical data for a user. The methods and systems have potential in a variety of healthcare cases, including genomics, diagnosis, point-of-care applications, pharmaceuticals, and clinic trials. For the purpose of example, many of the methods and systems are described herein in the context of analyzing data from men regarding prostate medical conditions.

In an aspect, a method utilizes computer-implemented personalized probability determination systems. In another aspect, the invention features methods for use in integrated health systems and methods related to organs of the human body and to cancer.

A treatment timing system can help men and their medical advisers choose a time for treatment of prostate cancer. The Treatment Timing system can build on the results of personalized probability analysis. The timing of treatment for prostate cancer can be a balancing act. Early treatment often increases the chance of cure but may increase the risk of unnecessary treatment and side effects.

Timing System

Figure 1:
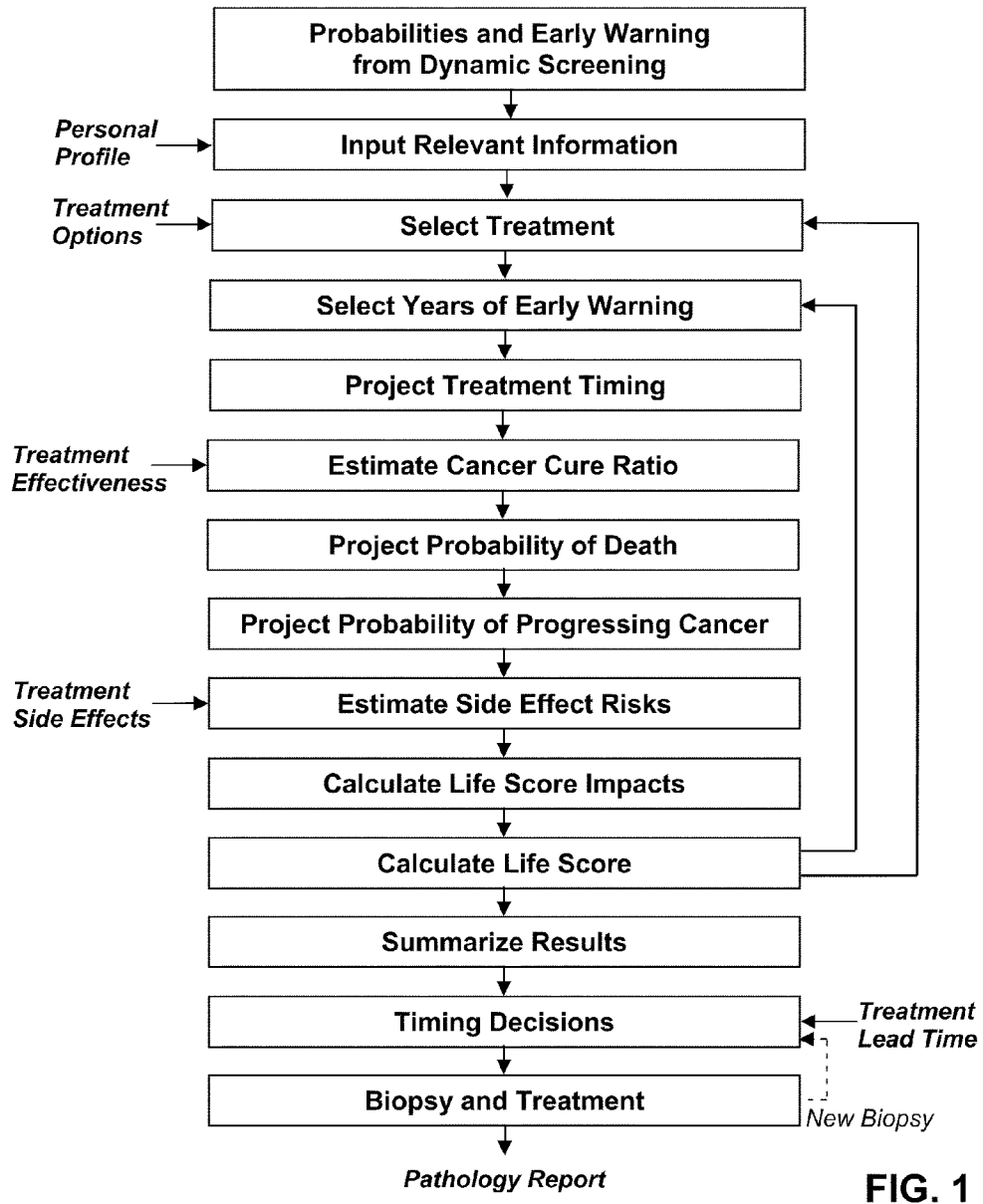
FIG. 1 illustrates an exemplary treatment timing flow chart.

Exemplary methods and systems are introduced briefly herein along with a flow chart on FIG. 1 as described here. The Probabilities and Early Warning results from dynamic screening are an input to the Treatment Timing system. Other relevant information including personal profile information is entered. Treatment is selected for analysis by the user or treatments are analyzed in iterative fashion by the system. The system analyzes a range of years of early and late warning in iterative fashion. The annual probability of treatment for each future year is projected based on the current probability of progressing cancer and years of early warning from the dynamic screening system in step. The Cancer Cure Ratio is estimated for treatment each year based on the amount of early or late warning. The Cure Ratio is used to project the probability of recurrence after treatment over time and subsequent progression. The probability of death from prostate cancer is projected from the risk of subsequent progression for each year of potential treatment and then cumulated for an overall probability projection. The risk of death from other causes is considered in estimating the increase in the overall risk of death for each future year. For each year of treatment the probability of treatment in that year is used to weight the subsequent risk of side effects. The risks for each year of treatment are cumulated to estimate an overall risk of side effects for each future year. Changes in Life Score are calculated for the increased risk of death by year and for the risk of side effects using the Emotional Weights entered by the user in his Personal profile. The man's overall Life Score may be reduced by the Life Score Impacts of increased risks of death and side effects. Results are summarized for each strategy. A man, medical personnel and other users (for example, family) can use Life Score simulations to help them choose the best timing for biopsy and treatment of progressing cancer. For a biopsy, a doctor uses a device to inject thin hollow needles into the prostate to extract tissue. Typically, a pathologist examines the tissue and may provide a diagnosis of prostate cancer. Primary treatment is intended to cure prostate cancer and can include surgery to remove the prostate and various types of radiation to kill the cancer. A pathology report after surgery can provide useful information about the progress of cancer.

Figure 2:
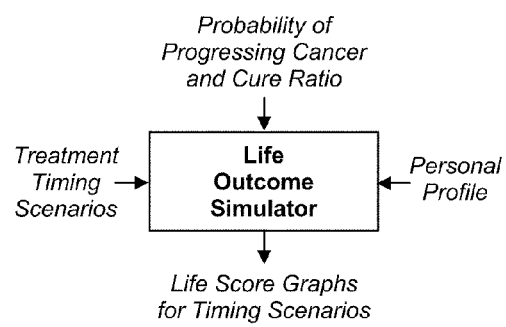
FIG. 2 shows an exemplary life outcome simulator for a range of treatment timing scenarios.

An exemplary life outcome simulator, as shown on FIG. 2, can be used to calculate Life Score Impacts and Life Scores on FIG. 1 for a range of treatment timing scenarios. The probability of progressing cancer from a previous module is an example input. The user may supply information on his Personal profile. The system may supply a standard range of treatment timing scenarios.

Figure 3:
FIG. 3 shows an exemplary Life Score graph of how Life Score varies for a range of treatment timing.
Figure 4:
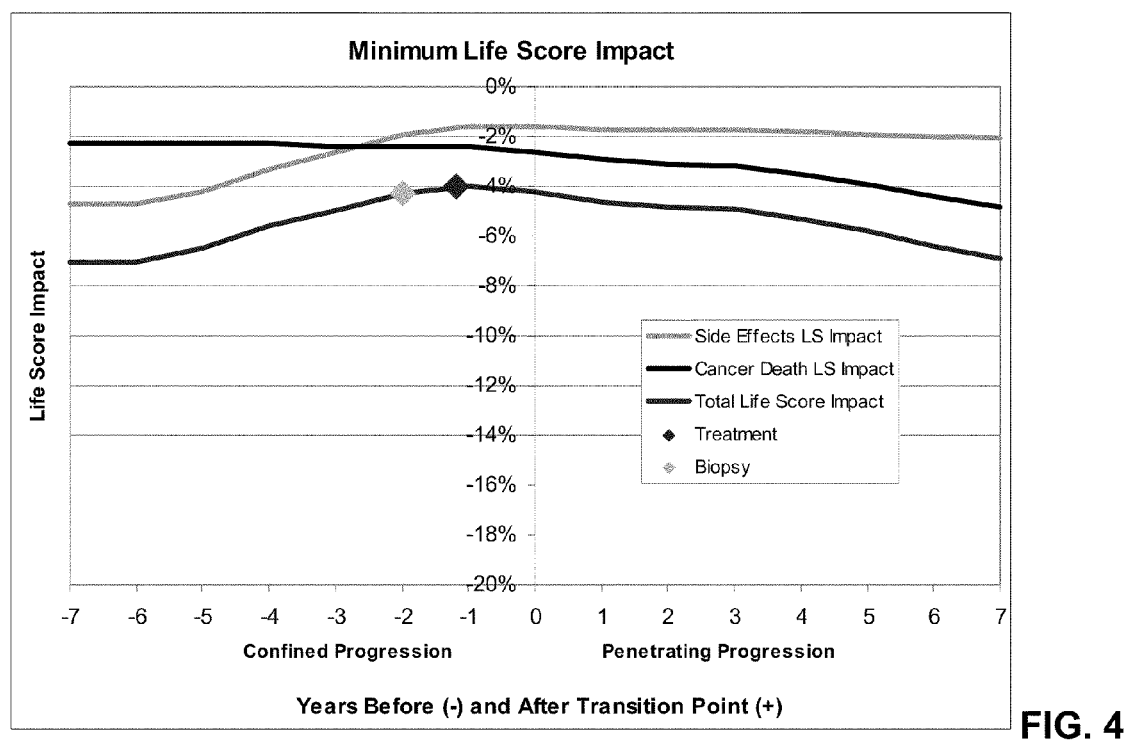
FIG. 4 shows an exemplary Life Score curve that is relatively flat because timing of prostate cancer treatment causes relatively small changes in well-being and length of life.

In an embodiment, Life Score is a measure of well-being and length of life, based on the information entered in the profile. The exemplary Life Score graph on FIG. 3 shows how Life Score varies for a range of treatment timing. A value of 100% may represent Life Score in the absence of prostate cancer and serve as a point of reference. In the example of FIG. 4, The Life Score curve is relatively flat because timing of prostate cancer treatment causes relatively small changes in well-being and length of life. Timing can be measured in years before and after the Transition Point, (for example, the time of progression when the cure rate begins to decline steeply) of progressing cancer (year 0). Before the Transition Point the Cure Ratio may decline relatively slowly. After the Transition Point the Cure Ratio can drop more steeply as the risk increases that cancer has spread outside of the prostate.

The line and treatment diamond on the graph on FIG. 3 may depend on the primary treatment selected in the profile (for example, surgery, dual radiation, seed radiation and external radiation). The treatment diamond on each graph shows the treatment timing that maximizes Life Score and minimizes Life Score impact. For Life Scores that are different, one way to interpret the difference can be in the context of a total life. For example, if someone expects to live thirty more years, a 3% difference in Life Score would be equivalent to almost 1 year of life. In the exemplary figures, the diamond on each graph shows a rough estimate of biopsy timing that corresponds with the treatment timing that maximizes Life Score. A first biopsy should occur roughly six months to a year before the optimal time for treatment, so the biopsy timing diamond may show up on the graphs approximately six months to a year or more before the treatment timing diamond. The actual size of the biopsy lead time depends on a variety of factors.

In an embodiment, Life Score Impact is the reduction in Life Score by side effects and death from prostate cancer. Life Score Impact can measure the drop from 100% on the Life Score graph of the previous FIG. 3. The graph on FIG. 4 shows an exemplary Life Score Impact for the range of treatment timing. The bottom curve shows the total Life Score Impact for the treatment that is chosen. It is the sum of reduction in Life Score from side effects and death from prostate cancer. The curve is more pronounced than on the previous graph because the scale has been expanded. It does not span the full range of possible impacts from 0% to 100%. The treatment diamond on each graph shows the treatment timing that maximizes Life Score and minimizes Life Score impact. The diamond on each graph shows a rough estimate of biopsy timing that corresponds with the treatment timing that maximizes Life Score. The top curve shows the Life Score Impact of all side effects. The impact is greatest on the left when the risk of unnecessary treatment is greatest. The middle curve shows the Life Score Impact of death from prostate cancer. The impact is greatest on the right when late treatment leads to a decrease in cure rate and an increased risk of cancer death.

Disclosed herein are computer-implemented personalized probabilities determination systems and methods for use in integrated health systems and methods related to organs of the human body and to cancer. For example, a system and method is disclosed herein for estimating trends in biomarkers and calculating the probability of certain conditions of one or more organs of the human body. This exemplary system and method could be used for any condition of any organ of the human body. An application to the male prostate with a focus on progressing prostate cancer is disclosed as an example here without limitation.

Personalized Probabilities

In an aspect, a method is disclosed of performing a course of medical action for a medical condition of a subject comprising: obtaining a first value of at least one biomarker from a subject;

sending said first value to a computer system that calculates a first plurality of posterior probabilities of the occurrence of a plurality of medical conditions of said subject using said first value, wherein said plurality of medical conditions comprises at least a first and second medical condition; receiving said first plurality of posterior probabilities; performing a first course of medical action for the first medical condition based on said first plurality of posterior probabilities; observing a result of said first course of medical action; obtaining a second value of at least one biomarker from said subject; sending said second value and said result of said first course of the medical action to said computer system that calculates a second plurality of posterior probabilities of the occurrence of said plurality of medical conditions of said subject, wherein said calculation uses said at second value and said result; receiving said second plurality of posterior probabilities; and performing a second course of medical action for the second medical condition based on said second plurality of posterior probabilities.

In an embodiment, the first or second value is a PSA value or fPSA value. In another embodiment, the subject is a human, for example a patient.

In an embodiment, a computer system comprises a device for network communication, a storage unit, and a processor. The computer system can comprise a Monte Carlo engine.

In an embodiment, sending comprises entering said first and second values into a webpage or using a device that transmits either or both of said first and second values to said computer system through a wireless network.

In an embodiment, first and second values are a first and second biomarker trend of biomarker values over a period of time. A computer system can calculate each of said first plurality of posterior probabilities by relating: a prior probability of a medical condition; a probability of observing said first biomarker trend for an individual with said medical condition; and a probability of observing said first biomarker trend for an individual without said medical condition. A computer system can calculate each of said second plurality of posterior probabilities by relating: a prior probability of a medical condition, wherein said prior probability was calculated using subject information comprising said result of a course of medical action; a probability of observing said second biomarker trend for an individual with said medical condition; and a probability of observing said second biomarker trend for an individual without said medical condition.

In an embodiment, a plurality of medical conditions are prostate medical conditions, for example they can be selected from the group consisting of the following: prostatitis due to inflammation, prostatitis due to infection, prostate cancer, benign prostate hyperplasia, and no prostate disease.

In an embodiment, receiving comprises viewing a display of said posterior probabilities, for example a display on an output device. An output device can be selected from the group consisting of the following: a computer, a webpage, an electronic medical record, a printout, and a personal electronic device.

In an embodiment, a first or second course of medical action is delivering medical treatment to said subject, such as a medical treatment is selected from a group consisting of the following: a pharmaceutical, surgery, organ resection, and radiation therapy. In an embodiment, a pharmaceutical comprises a chemotherapeutic compound for cancer therapy. In another embodiment, the first or second course of medical action comprises administration of medical tests or medical imaging of said subject or setting a specific time for delivering medical treatment or a biopsy or a consultation with a medical professional.

In an aspect of the invention, a method of delivering a probability that a subject has a medical condition to a user comprises: calculating a plurality of posterior probabilities of the occurrence of a plurality of medical conditions of a subject having a biomarker trend, wherein said biomarker trend comprises biomarker values from said subject at more than one time, and wherein each of said plurality of posterior probabilities is calculated by relating: a prior probability of the occurrence of each of said plurality of medical conditions; and a probability of observing said biomarker trend for an individual with each medical condition; and a probability of observing said biomarker trend for an individual without each medical condition; and delivering said plurality of probabilities of said plurality of medical conditions to a user with an output device.

In another aspect, a method of delivering a probability that a subject has a medical condition to a user comprises: calculating a plurality of posterior probabilities of the occurrence of a plurality of medical conditions of a subject having a result of a course of medical action and having a biomarker trend, wherein said biomarker trend comprises biomarker values from said subject at more than one time, and wherein each of said plurality of posterior probabilities is calculated by relating: a prior probability of the occurrence of each of said plurality of medical conditions, wherein said prior probability was calculated using subject information comprising said result of a course of medical action; a probability of said biomarker trend for an individual with each medical condition; and a probability of said biomarker trend for an individual without each medical condition; and delivering said plurality of probabilities of said plurality of medical conditions to a user with an output device. A biomarker trend can be a PSA trend or fPSA trend.

In an embodiment, an output device is selected from the group consisting of the following: a computer, a webpage, an electronic medical record, a printout, and a personal electronic device.

A course of medical action can be delivering medical treatment to said subject, for example a medical treatment selected from a group consisting of the following: a pharmaceutical, surgery, organ resection, and radiation therapy.

The course of medical action can also comprise administration of medical tests, medical imaging of said subject, setting a specific time for delivering medical treatment, a biopsy, and/or consultation with a medical professional.

In yet another aspect, a method of delivering a probability that a subject has a medical condition to a user is disclosed comprising: calculating a plurality of posterior probabilities of the occurrence of a plurality of prostate medical conditions of a subject having a PSA value and an fPSA value, each at more than one time thereby having a PSA trend and an fPSA trend, wherein each of said plurality of posterior probabilities is calculated by relating: a prior probability of a prostate medical condition; and a probability of observing said PSA trend and said fPSA trend for an individual with said prostate medical condition; and a probability of observing said PSA trend and said fPSA trend for an individual without said prostate medical condition; and delivering said plurality of probabilities of said plurality of medical conditions to a user with an output device. In an embodiment, a method can further comprise: calculating a second plurality of posterior probabilities of the occurrence of said plurality of prostate medical conditions of a subject having a result of a course of medical action and having a new PSA value and a new fPSA value, each at more than one time thereby having a second PSA trend and a second fPSA trend, wherein each of said plurality of posterior probabilities is calculated by relating: a prior probability of a prostate medical condition, wherein said prior probability was calculated using subject information comprising said result of a course of medical action; and a probability of observing said second PSA trend and said second fPSA trend for an individual with said prostate medical condition; and a probability of observing said second PSA trend and said second fPSA trend for an individual without said prostate medical condition; and delivering said second plurality of probabilities of said plurality of medical conditions to the user with an output device.

A system to perform the Bayes calculation of the probability of progressing cancer can be configured with the following components: 1) prior probabilities of cancer at various stages of progression; 2) probability of the observation of various biomarker trends conditional on no progressing cancer; and 3) probability of the observation of various biomarker trends conditional on cancer at various stages of progression.

A system can be configured for generating one or both of the last two categories of probabilities for an individual man with specific observed biomarker trends and corresponding measurement uncertainty in those trends.

For example, consider a man concerned about prostate cancer with a series of PSA and free PSA biomarker results from blood tests. Trends can be estimated for each biomarker and analyzed using methods previously disclosed. For example, trend PSA velocity is the annual rate of change in trend PSA; trend free PSA % is trend free PSA divided by trend PSA; and trend free PSA velocity % is trend free PSA velocity divided by trend PSA velocity. The results can be as in Table 1.

TABLE 1

Example of values for biomarker trends.

| trend | Value | Standard Deviation |
|---|---|---|
| trend PSA | 3.0 | 0.4 |
| trend PSA velocity | 0.40 | 0.20 |
| trend free PSA % | 17.0% | 2.0% |
| trend free PSA velocity % | 6.0% | 3.0% |

Other information about the man may be available, including, age, measurement of prostate volume in some cases, and other factors that may affect the conditional probabilities.

Typically, no highly specific conditional distributions can be estimated directly from available population data. In an aspect, a disclosed method calculates the needed personalized probabilities.

In an embodiment, a method comprises creating personalized biologic probability models of several states: 1) no cancer conditions of the prostate: healthy and volume growth; 2) cancer at various stages of progression, and 3) combined models of no cancer conditions and various stages of cancer progression. Those models are then combined with trend uncertainty models to create an overall multi-dimensional distribution or part of the distribution relevant to the specific trend results. The distributions can be multi-dimensional in that trend values and trend velocities, or annual rates of change, are considered for at least one biomarker, such as PSA. The disclosed example describes a method for creating four dimensional distributions and probabilities for two biomarkers: PSA and free PSA. In an embodiment, higher dimensional distributions and probabilities are needed when additional biomarkers are considered.

For example, Monte Carlo methods may be used to create four dimensional probability distributions for PSA, PSAV, fPSA % and fPSAV % from random draws from the probability distributions of the underlying biologic and trend uncertainty models. A calculation process can be time consuming and slow a response user inputting and receiving information on the internet or world wide web. The complexity and time of calculation can increase exponentially as additional biomarkers become available and are incorporated into the method. Therefore, efficient methods of calculating the probabilities can be beneficial.

For example, a method focuses on the probabilities of the observed trend values rather than larger four dimensional probability distributions for PSA, PSAV, fPSA % and fPSAV % for the full range of possible outcomes. This approach reduces the amount of calculations necessary to calculate the personalized probabilities needed for the Bayes calculations. In an embodiment, the reduction is achieved in practice using a hierarchical triage approach that aborts a Monte Carlo iteration as soon as one of the values falls outside the target range for first PSA, then PSAV, then fPSA % and finally fPSAV %.

A prostate dynamic screening system can help men and their doctors screen for progressing cancer, long-term conditions and short-term conditions. It provides early warning of progressing cancer while reducing the probability of unnecessary treatment and side effects. The results can be useful inputs to the optimal Treatment Timing system. The prostate is the organ of the body used in many of the examples described herein, however, the methods and systems described herein are useful for a variety of biomarkers for a variety of diseases. Conditions used as examples are progressing prostate cancer, prostate volume growth caused by Benign Prostatic Hyperplasia (BPH) and infections of the prostate. Both PSA and free PSA tests can be used for screening. Other tests may supplement them or replace them.

Figure 5:
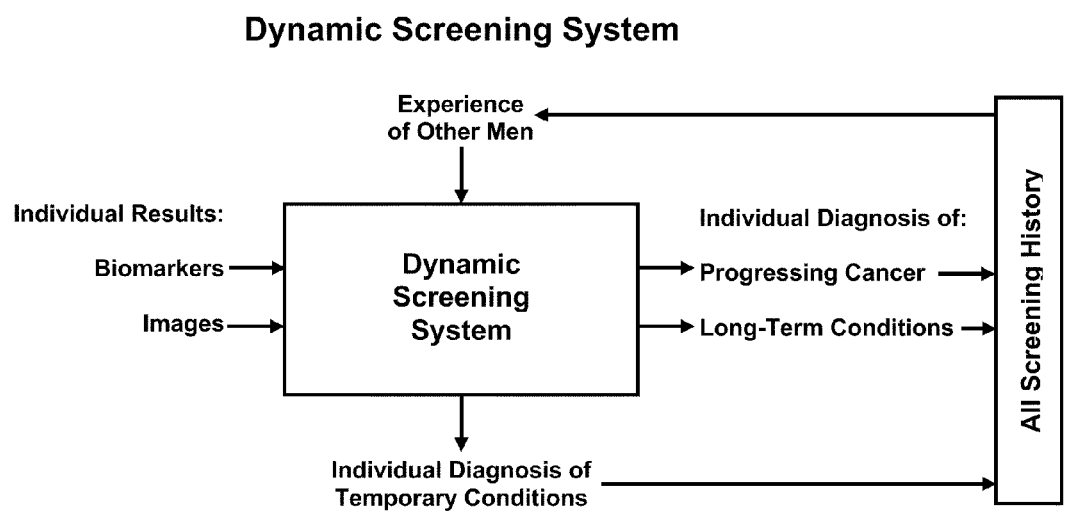
FIG. 5 provides an exemplary overview of an embodiment of a dynamic screening system.

The flow chart on FIG. 5 provides an exemplary overview of an embodiment of a dynamic screening system. For one person, biomarker and image results are input on the left. For the prostate, these are PSA and free PSA test results and ultrasound measurements of prostate volume. The experience of other men is input from the top. A diagnosis of temporary conditions comes out the bottom. For the prostate, an infection is the most common and serious temporary condition. Diagnoses of progressing cancer and long-term conditions (volume growth due to BPH for the prostate) are output on the right. All output becomes part of all screening history and is fed back as the experience of other men to increase the power of dynamic screening.

Figure 6:
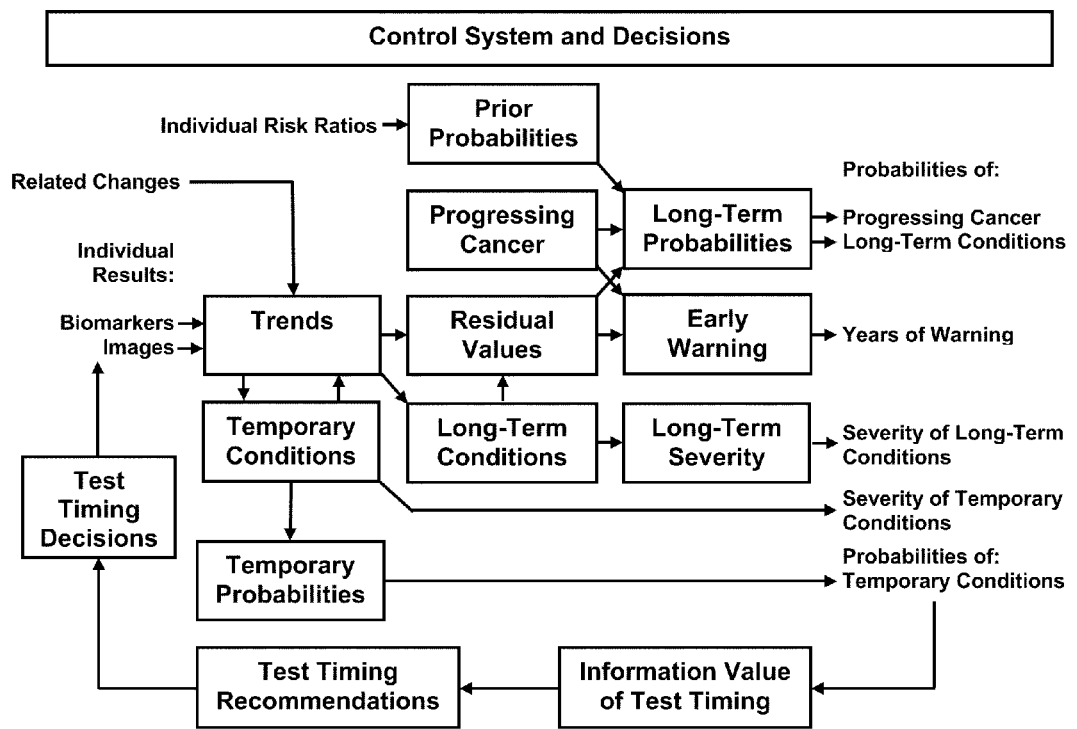
FIG. 6 shows some embodiments of modules of the dynamic screening system.

The flow chart on FIG. 6 shows some embodiments of modules of the dynamic screening system. A user can complete a profile. The prostate strategy system can analyze strategy alternatives and can choose the best life strategy.

Using the dynamic screening system, the man can follow suggestions about the type and timing of primary and secondary screening tests. Typically the system can recommend a baseline prostate volume study and annual PSA and free PSA tests. Free PSA tests are currently recommended; however, other tests may be recommended in the future in conjunction with free PSA or to substitute for it. Tests results can be entered into the system for analysis and guidance. Steadily increasing PSA due to prostate enlargement from BPH, if rapid enough, may lead the system to suggest periodic prostate volume measurements to define the rate of growth. Tests results can be entered into the system for analysis and guidance.

The dynamic screening system can recognize the false alarms caused by infection and other temporary conditions, provide a calming perspective, suggest new PSA and free PSA tests after the infection or condition has passed, and analyze the results of new tests.

The dynamic screening system can recognize early warning of possible cancer progression and suggest additional confirmation tests. Confirmation tests may include other components of PSA such as Pro PSA and any other useful new markers developed in the future. In addition, a new prostate volume study may be suggested, perhaps using more expensive technology if rapid prostate enlargement is a factor. A second round of confirmation tests can be suggested— perhaps six months after the first. Additional confirmation tests can be suggested until progression has been confirmed or rejected.

The dynamic screening system can confirm a high probability of progressing cancer when its calculation shows the probability is high enough to warrant consideration of biopsy and treatment The optimal treatment timing system can calculate the optimal schedule for biopsy and treatment based on ongoing screening tests and the information entered in the profile. The man and his advisors can use the results to schedule a first biopsy and subsequent treatment.

In the feedback learning process, the man or his doctor will provide follow up information for the system to analyze and incorporate for use by other men.

Figure 7:
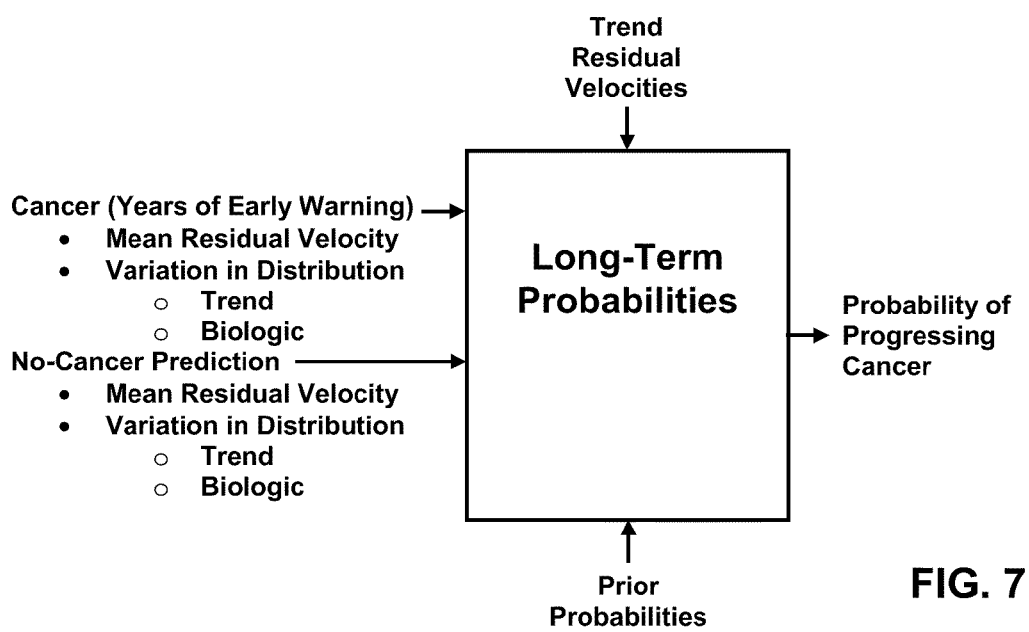
FIG. 7 shows an example of the high level inputs and outputs for estimating the probability of progressing cancer.

The exemplary long-term probabilities module of FIG. 6 estimates the probabilities of one or more long-term conditions, such as progressing cancer or prostate volume growth. FIG. 7 shows an example of the high level inputs and outputs for estimating the probability of progressing cancer. Prior probabilities are the starting point in FIG. 6. Trend residual velocities come from FIG. 6. Velocities and trends may be used in other embodiments. The long-term probabilities module on FIG. 7 adjusts the prior probabilities of progressing cancer based on how the trend residual velocities compare with patterns for progressing cancer and the predicted values for no cancer. A variety of methods can be used to estimate the probability, including Bayesian and simulation methods. The process can involve a variety of cancer stages, characterized by years of early warning, which is measured as years before the transition point, defined as the time of progression when the cure rate begins to decline steeply. Therefore, a module may consider a range of progressing cancer possibilities (different years of early warning) and a no-cancer (not present or not progressing) possibility defined by the no-cancer predicted values. For each of these possibilities a probability distribution can be constructed that can be characterized by a mean and by variation, which can be characterized by standard deviations. There are two sources of variation that can be considered. First, trend variation can be caused by possibly random variation in test results. Second, biologic variation can be caused by differences among men or for a specific man over time.

Figure 8:
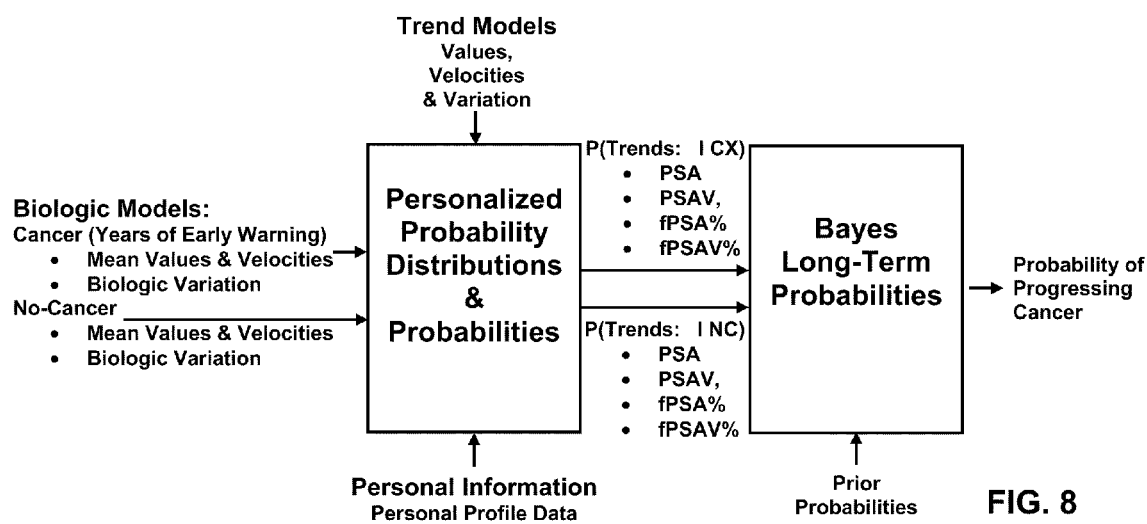
FIG. 8 illustrates an alternative method for creating the long-term probabilities.

The approaches described herein can be used as an alternative method for creating the long-term probabilities, as shown on FIG. 8. The long-term probabilities module is split into a personalized probability distributions module and probabilities module and a Bayes long-term probabilities module. The Bayes calculations in the second module have been disclosed in the above incorporated references. The first module is described below. The outputs of module are probabilities of the observed trend results: PSA, PSAV, fPSA % and fPSAV % conditional on no cancer and cancer for various years (X). These are created using personal information and input from biologic and trend models, as disclosed below.

Figure 9:
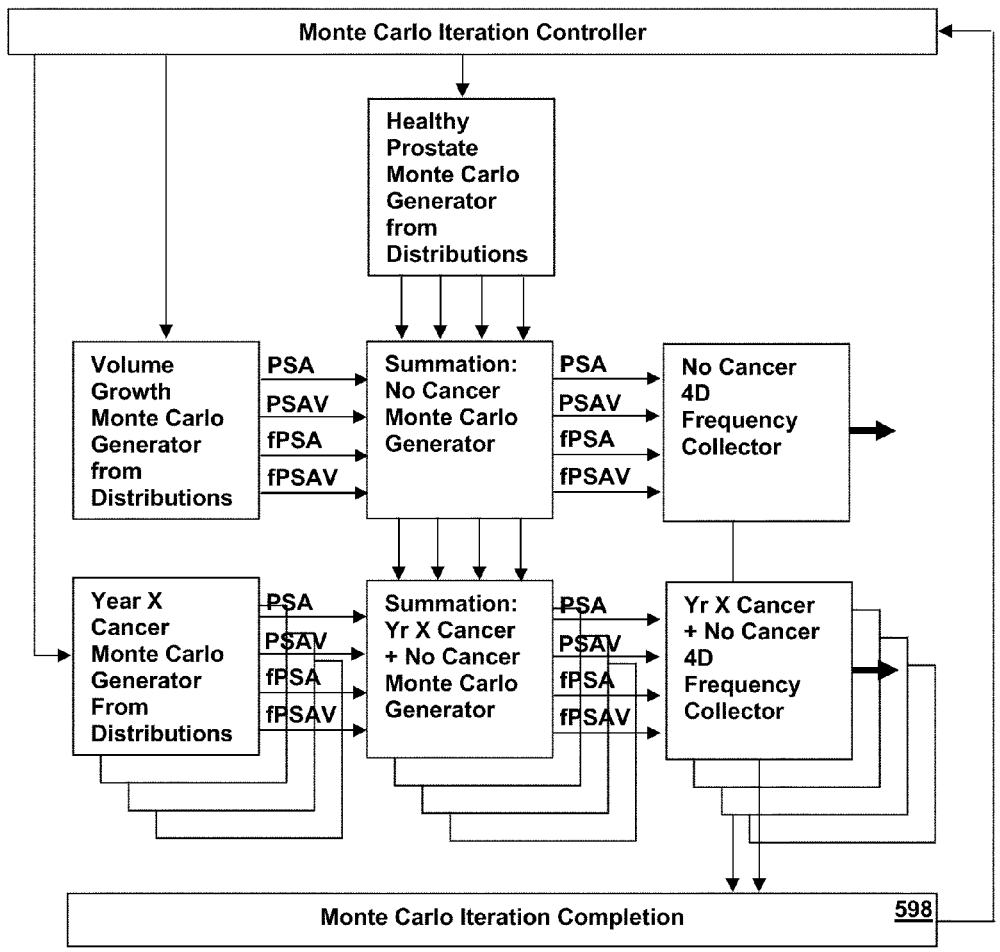
FIG. 9 demonstrates an embodiment of the personalized probability distributions and probabilities module uses a four dimensional frequency generator.

In an embodiment, the personalized probability distributions and probabilities module uses a four dimensional frequency generator, shown on FIG. 9, which calculates personalized probability distributions and probabilities for cancer and no cancer cases in iterative fashion. Each iteration is initiated by the Monte Carlo iteration controller and ended by the Monte Carlo iteration completion module, which returns control to the controller. For each iteration, trend values for a healthy prostate are generated from probability distributions. Trend values for prostate volume growth are generated from probability distributions. No cancer values are calculated in module as the sum of values. The values for each iteration are added to the appropriate four dimensional bucket defined by ranges in four dimensions. As the number of iterations increase, frequency distributions for the no cancer case are built up and output at the end of the process. For each iteration, trend values for each year X cancer case are generated from probability distributions. A range of cases are calculated for year X cancers, where X is a measure of cancer progression. Values for each year X cancer plus no cancer case are calculated in module as the sum of values. The values for each iteration are added to the appropriate four dimensional bucket defined by ranges in four dimensions. As the number of iterations increase, frequency distributions for each year X cancer plus no cancer case are built up and output at the end of the process.

Figure 10:
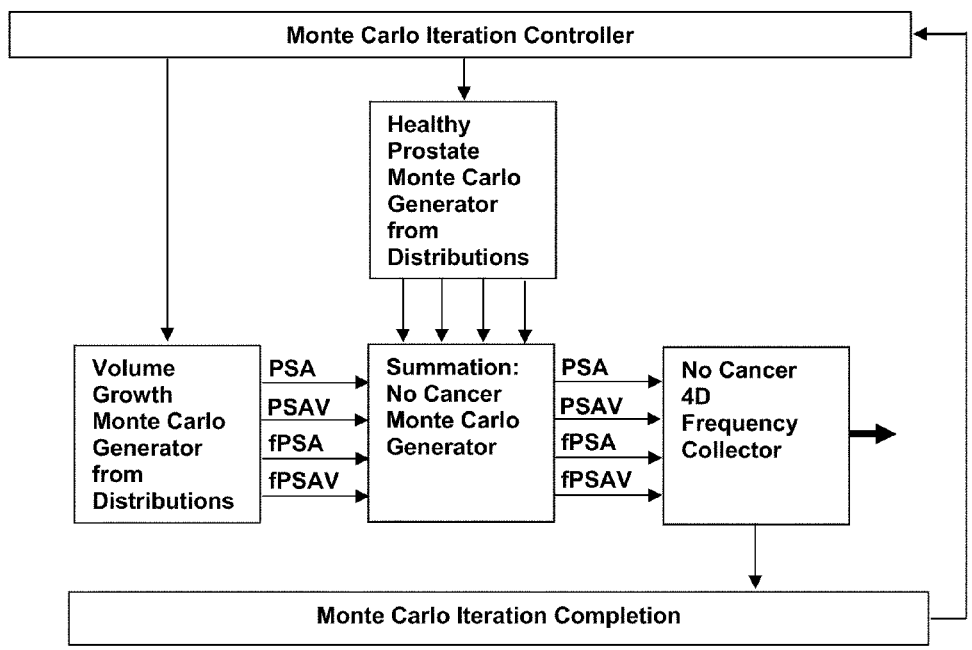
FIG. 10 shows an embodiment of a four dimensional frequency generator that calculates personalized probability distributions and probabilities for the no cancer case in iterative fashion.

It can be computationally more efficient to use independent Monte Carlo processes for the no cancer case and cancer plus no cancer cases. In an embodiment, the four dimensional frequency generator, shown on FIG. 10, calculates personalized probability distributions and probabilities for the no cancer case in iterative fashion. Each iteration is initiated by the Monte Carlo iteration controller and ended by the Monte Carlo iteration completion module, which returns control to the controller. For each iteration, trend values for a healthy prostate are generated from probability distributions. Trend values for prostate volume growth are generated from probability distributions. No cancer values are calculated as the sum of values. The values for each iteration are added to the appropriate four dimensional bucket defined by ranges in four dimensions. As the number of iterations increase, frequency distributions for the no cancer case are built up.

Figure 11:
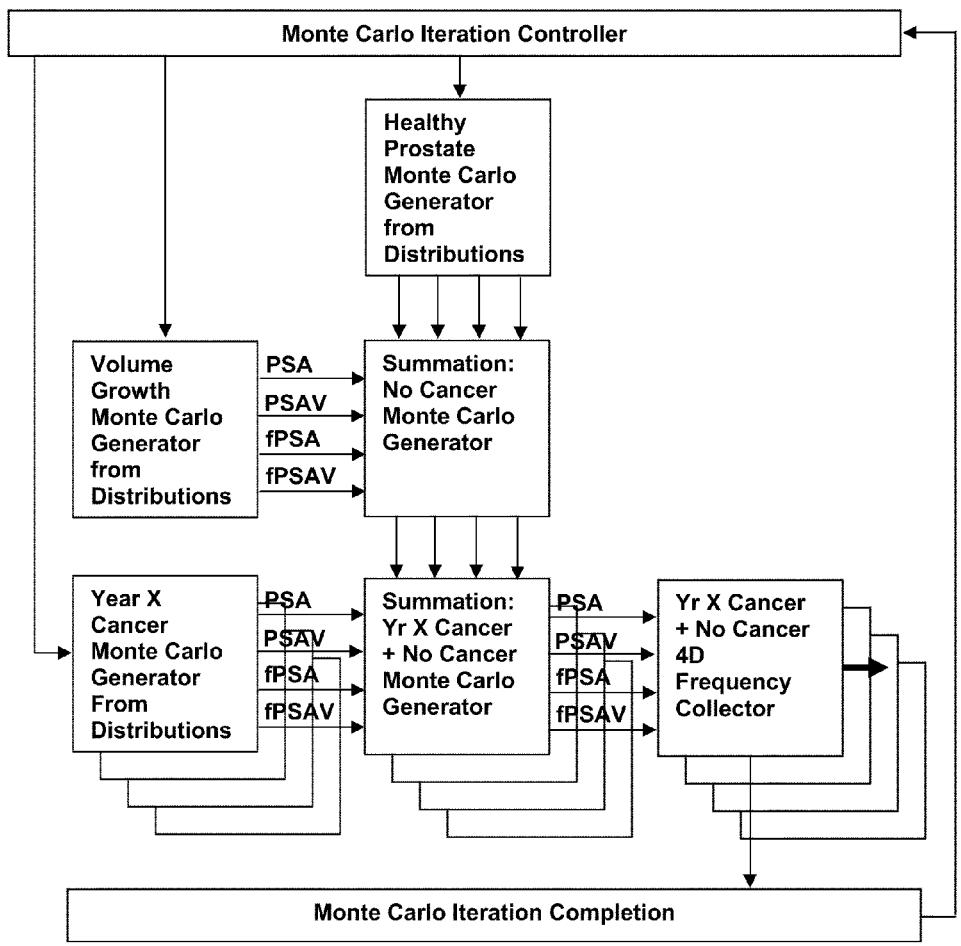
FIG. 11 shows an embodiment of a four dimensional frequency generator that calculates personalized probability distributions and probabilities for cancer plus no cancer cases in iterative fashion.

In another embodiment, the four dimensional frequency generator, shown on FIG. 11, calculates personalized probability distributions and probabilities for cancer plus no cancer cases in iterative fashion. Each iteration is initiated by the Monte Carlo iteration controller and ended by the Monte Carlo iteration completion module, which returns control to the controller. For each iteration, trend values for a healthy prostate are generated from probability distributions. Trend values for prostate volume growth are generated from probability distributions. No cancer values are calculated as the sum of values. For each iteration, trend values for each year X cancer case are generated from probability distributions. A range of cases are calculated for year X cancers, where X is a measure of cancer progression. Values for each year X cancer plus no cancer case are calculated in module as the sum of values from. The values for each iteration are added to the appropriate four dimensional bucket defined by ranges in four dimensions. As the number of iterations increase, frequency distributions for each year X cancer plus no cancer case are built up.

The approach described in this example generates extensive four dimensional distributions that can be used to find the probabilities needed for the Bayes calculations of the probability of progressing cancer. However, the calculations can be time consuming and cause delays in real-time responses to users. The approach of focused probabilities is discussed below to address this if it is an issue for a situation at hand. The number of calculations and the time to perform them can be reduced substantially by focusing narrowly on the probabilities needed for the Bayes calculations rather than on generating extensive four dimensional distributions. Detailed methods for focusing on the needed probabilities are disclosed below.

Figures 12, 13:
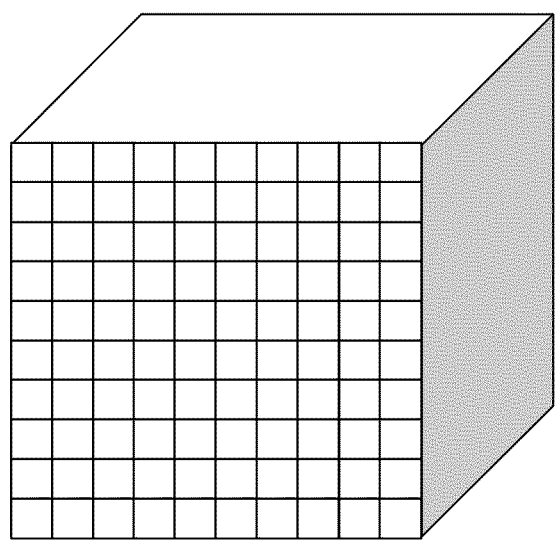
FIG. 12 shows an example of the 100 possible buckets of possible results when each dimension is divided into ten segments.
FIG. 13 shows an example of the 10,000 possible buckets of possible results when each dimension is divided into ten segments (even though only three of the four dimensions can be depicted).

For an exemplary biomarker, such as PSA, two dimensions may be needed, for example, PSA and PSA velocity (PSAV). A two dimensional rectangle of possible Monte Carlo results can be created by dividing each dimension into segments. The example in FIG. 12 shows the 100 possible buckets of possible results when each dimension is divided into ten segments.

As an example, the segments for each of the two dimensions can be as described in Table 2 and 3.

TABLE 2

Ten segments for the PSA dimension

>=0 and <1
>=1 and <2
>=2 and <3
>=3 and <4
>=4 and <5
>=5 and <6
>=6 and <7
>=7 and <8
>=8 and <9
>=9

TABLE 3

Ten segments for the PSAV dimension

>=0.0 and <0.1
>=0.1 and <0.2
>=0.2 and <0.3
>=0.3 and <0.4
>=0.4 and <0.5
>=0.5 and <0.6
>=0.6 and <0.7
>=0.7 and <0.8
>=0.8 and <0.9
>=0.9

In another example, for two tests, such as PSA and free PSA, four dimensions can be important, for example PSA, PSAV, fPSA % and fPSAV %. A four dimensional hyper cube of possible Monte Carlo results can be created by dividing each dimension into segments. The example of FIG. 13 suggests the 10,000 possible buckets of possible results when each dimension is divided into ten segments (even though only three of the four dimensions can be depicted).

In another example, consider a man concerned about prostate cancer with a series of PSA biomarker results from blood tests. Trends can be estimated for each biomarker and analyzed using methods previously disclosed. For example, the results can be as described in Table 4.

TABLE 4

| Trend | Value | Standard Deviation |
|---|---|---|
| trend PSA | 3.0 | 0.4 |
| trend PSA velocity | 0.40 | 0.20 |

The bucket used to collect the frequency of this outcome can be as described in Table 5.

TABLE 5

PSA = 3.0 +/− 0.5 or PSA >2.5 and <3.5
PSAV = 0.4 +/− 0.05 or PSAV >0.35 and <0.45

Figure 14:
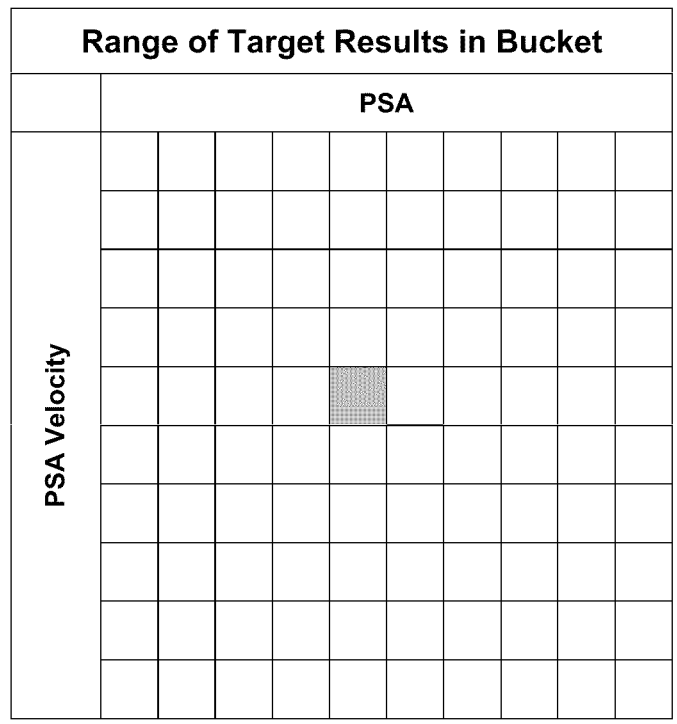
FIG. 14 shows conceptually the bucket of concern defined by the range of PSA and PSAV results around the observed trend results.

The gray rectangle on the table of FIG. 14 shows conceptually the bucket of concern defined by the range of PSA and PSAV results around the observed trend results. For one case, other buckets that are not shaded are not of interest.

For a man concerned about prostate cancer with a series of PSA and free PSA biomarker results from blood tests, trends can be estimated for each biomarker and analyzed using methods previously disclosed. The results can be as in Table 6.

TABLE 6

| trend | Value | Standard Deviation |
|---|---|---|
| trend PSA | 3.0 | 0.4 |
| trend PSA velocity | 0.40 | 0.20 |
| trend free PSA % | 17.0% | 2.0% |
| trend free PSA velocity % | 6.0% | 3.0% |

The bucket used to collect the frequency of this outcome can be as in Table 7.

TABLE 7

| |
|---|
| PSA = 3.0 +/− 0.5 or PSA >2.5 and <3.5 |
| PSAV = 0.4 +/− 0.05 or PSAV >0.35 and <0.45 |
| fPSA % = 17.0% +/− 2.0% or fPSA % >15.0% and <19.0% |
| fPSAV % = 6.0% +/− 2.0% or fPSAV % >4.0% and <8.0% |

Figure 15:
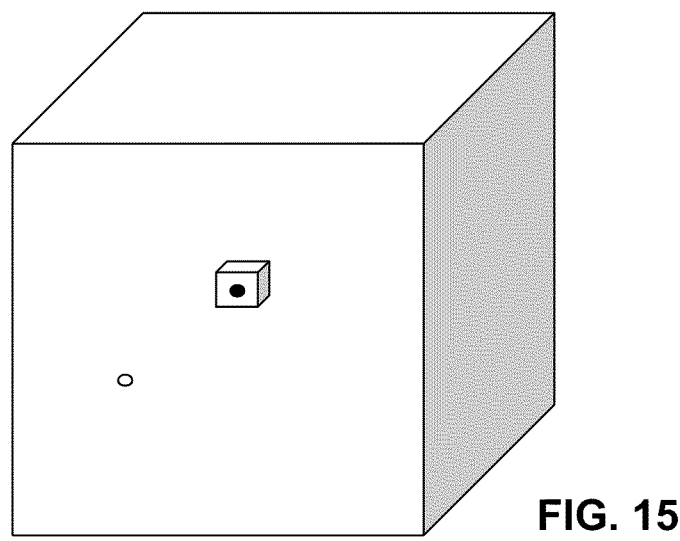
FIG. 15 suggests conceptually the hypercube bucket of concern defined by the range of PSA, PSAV, fPSA % and fPSAV % results around the observed trend results (even though only three of the four dimensions can be depicted).

The small cube inside the large cube shown by the example in FIG. 15 suggests conceptually the hypercube bucket of concern defined by the range of PSA, PSAV, fPSA % and fPSAV % results around the observed trend results (even though only three of the four dimensions can be depicted). For one case, the other buckets that are outside the small cube are not of interest. In general, for a single case trend values for PSA, PSAV, fPSA % and fPSAV % are known, which is a point in the 4D hyper cube. A small hyper cube bucket around the point can be created to collect Monte Carlo results that fall within the ranges. The frequency of the results in the bucket can be used to estimate the probability of the results.

TABLE 8

| |
|---|
| trend PSA +/− PSA Range Delta |
| trend PSAV +/− PSAV Range Delta |
| trend fPSA % +/− fPSA % Range Delta |
| trend fPSAV % +/− fPSAV % Range Delta |

Monte Carlo results that fall with the bucket, like the solid dot in the small cube of FIG. 15, are recorded; and results that fall outside the bucket, like the circle in the large cube of FIG. 15, are not recorded.

Figure 16:
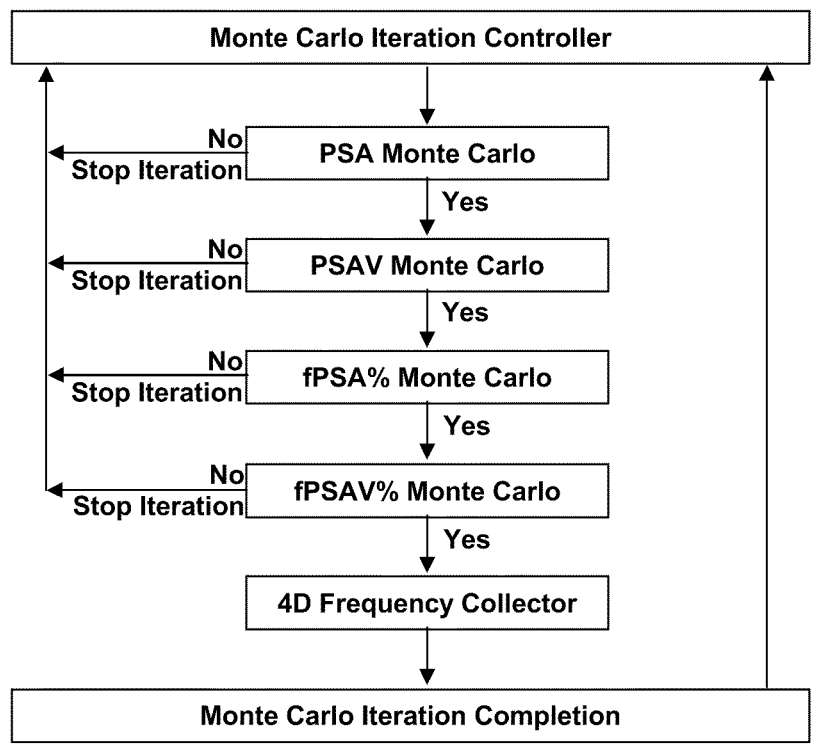
FIG. 16 shows an exemplary four dimensional frequency generator for the no cancer case. Each iteration is initiated by the Monte Carlo iteration controller.

FIG. 16 shows an exemplary four dimensional frequency generator for the no cancer case. Each iteration is initiated by the Monte Carlo iteration controller. For each iteration, PSA is calculated in module using Monte Carlo methods. The process stops for this iteration if PSA falls outside of the target range of the bucket, but the process continues if PSA falls within the target range of the bucket. If the iteration continues, PSAV is calculated in module using Monte Carlo methods. The process stops for this iteration if PSAV falls outside of the target range of the bucket, but the process continues if PSAV falls within the target range of the bucket. If the iteration continues, fPSA % is calculated in module using Monte Carlo methods. The process stops for this iteration if fPSA % falls outside of the target range of the bucket, but the process continues if fPSA % falls within the target range of the bucket. If the iteration continues, FPSAV % is calculated in module using Monte Carlo methods. The process stops for this iteration if FPSAV % falls outside of the target range of the bucket, but the process continues if FPSAV % falls within the target range of the bucket. The four dimensional frequency collector keeps track of the number of Monte Carlo iterations started and the number of outcomes that fall in the 4D bucket. Frequency is calculated by dividing the number of outcomes in the bucket by the number of iterations started. Finally, control is passed to the Monte Carlo iteration completion module.

Figure 17:
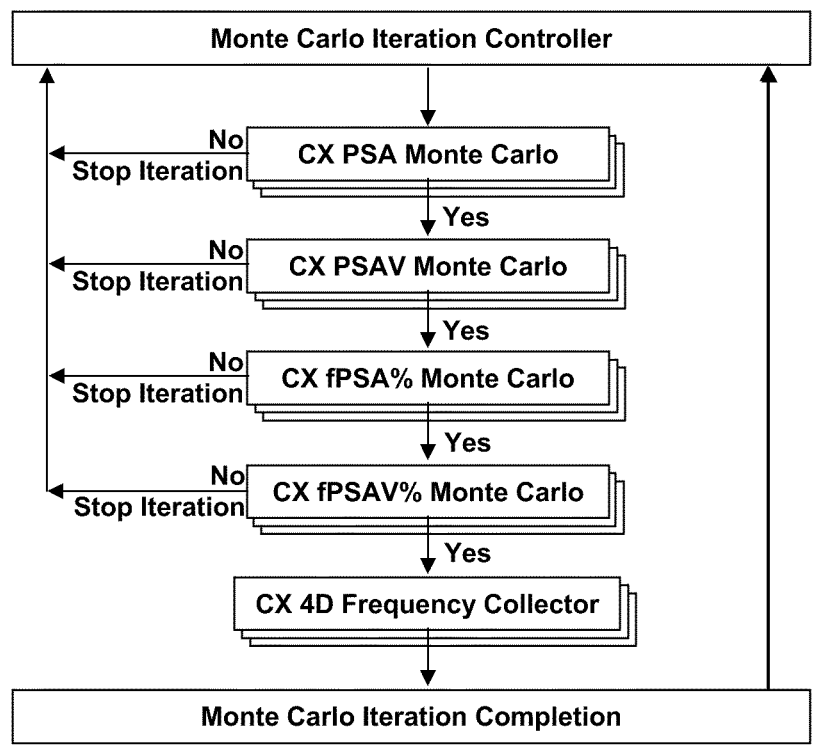
FIG. 17 shows an exemplary Monte Carlo process for generating outcomes for year X cancer from a number of probability distributions, where X is a measure of cancer progression.

FIG. 17 demonstrates an embodiment of a four dimensional frequency generator for each year X cancer plus no cancer case. Each iteration is initiated by the Monte Carlo iteration controller. For each iteration, PSA is calculated using Monte Carlo methods. The process stops for this iteration if PSA falls outside of the target range of the bucket, but the process continues if PSA falls within the target range of the bucket. If the iteration continues, PSAV is calculated using Monte Carlo methods. The process stops for this iteration if PSAV falls outside of the target range of the bucket, but the process continues if PSAV falls within the target range of the bucket. If the iteration continues, fPSA % is calculated using Monte Carlo methods. The process stops for this iteration if fPSA % falls outside of the target range of the bucket, but the process continues if fPSA % falls within the target range of the bucket. If the iteration continues, fPSAV % is calculated using Monte Carlo methods. The process stops for this iteration if fPSAV % falls outside of the target range of the bucket, but the process continues if fPSAV % falls within the target range of the bucket. The four dimensional frequency collector keeps track of the number of Monte Carlo iterations started and the number of outcomes that fall in the 4D bucket. Frequency is calculated by dividing the number of outcomes in the bucket by the number of iterations started. Finally, control is returned to the Monte Carlo iteration completion module.

FIG. 17 shows an exemplary Monte Carlo process for generating outcomes for year X cancer from a number of probability distributions, where X is a measure of cancer progression. For example, X can be measured as the number of years before or after the Transition Point, defined as the time of progression when the cure rate begins to decline steeply. Other reference points for measuring X may work as well. In this example, fifteen year X cases can be considered as in Table 9.

TABLE 9

| |
|---|
| 2 Years After the Transition Point |
| 1 Year After the Transition Point |
| 0 Years = At the Transition Point |
| 1 Year Before the Transition Point |
| 2 Years Before the Transition Point |
| 3 Years Before the Transition Point |
| 4 Years Before the Transition Point |
| 5 Years Before the Transition Point |
| 6 Years Before the Transition Point |
| 7 Years Before the Transition Point |
| 8 Years Before the Transition Point |
| 9 Years Before the Transition Point |
| 10 Years Before the Transition Point |
| 11 Years Before the Transition Point |
| 12 Years Before the Transition Point |

Choices can increase about the functional form of the trend and the window of time over which the trend is estimated as more test results become available over longer periods of time. Better choices obtain more and more valuable information from any given number of test results. An example is presented here of a one dimensional case where only a linear functional form is considered and the impact of a range of window sizes is studied.

In an aspect, four-dimensional frequency distributions from the Monte Carlo generator as described herein may be pre-computed. For the test-result types (each of which corresponds to one of the dimensions of the frequency distribution) that are available, the trend variation for the dimension (as described herein can be compared directly against the generated frequency distribution by the pre-computations. This evaluation produces the probabilities of observing the trend evidence under the assumption of the presence or absence of conditions such as prostate cancer. The frequency distributions and the trend-variation distributions can be smoothed by any number of strategies and thus captured by a single equation or a set of several equations, or they can be captured as frequency values in discrete buckets. The evaluation of one distribution weighted by the other may therefore involve either continuous or discrete variables. The multi-dimensional frequency distribution lends itself to being pre-computed and stored because it is based largely on static values describing the overall population and is personalized for an individual subject by a small number of inputs which capture some fundamental characteristics of the subject. For each discrete combination of those inputs a frequency distribution can be stored. For a subject whose values fall between sets of biomarker values which were used to create stored distributions, interpolation techniques such as linear interpolation or design of experiments may be used to extract a personalized distribution.

Figure 18:
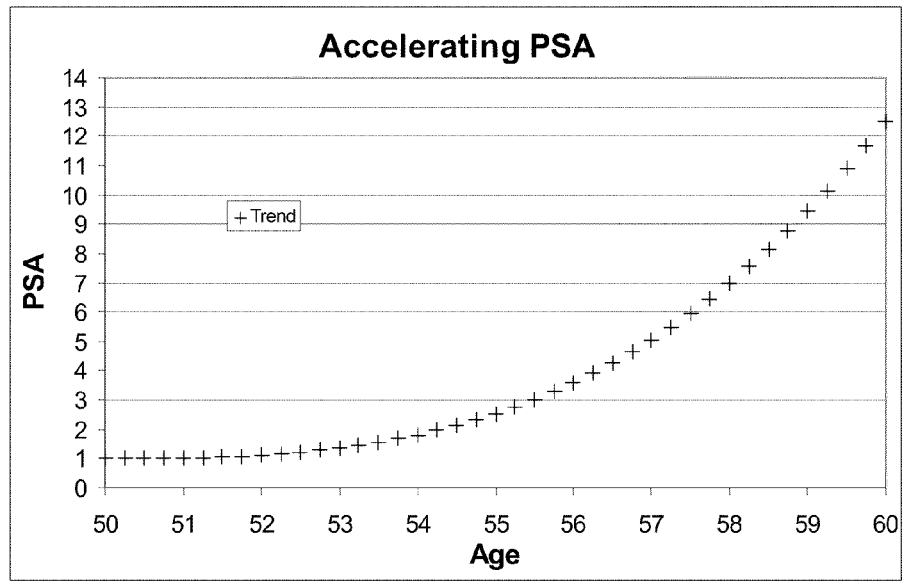
FIG. 18 demonstrates an exemplary pattern of accelerating PSA caused by progressing prostate cancer.
Figure 19:
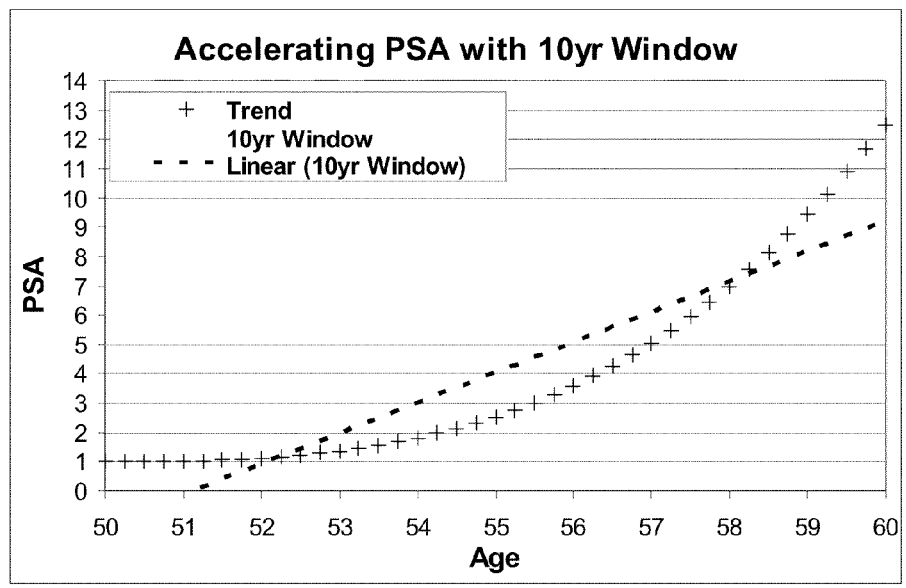
FIG. 19 shows a linear trend that best fits the example data over a ten year period from age 50 to age 60.

FIG. 18 demonstrates an exemplary pattern of accelerating PSA caused by progressing prostate cancer. At age 50 on the left healthy PSA starts at 1.0 and remains constant for over a year. PSA starts to accelerate at an increasing rate until it reaches about 12.5 at age 60 on the right. The dotted line on FIG. 19 shows a linear trend that best fits the example data over a ten year period from age 50 to age 60. The line does not fit the curved data perfectly. The line underestimates PSA from age 50 to about age 52. It overestimates PSA from about age 52 to just over age 58. It underestimates PSA from just over age 58 until age 60. At age 60 when the linear trend underestimates PSA by about 3.2 PSA (12.5 actual minus 9.3 for the linear trend).

Figure 20:
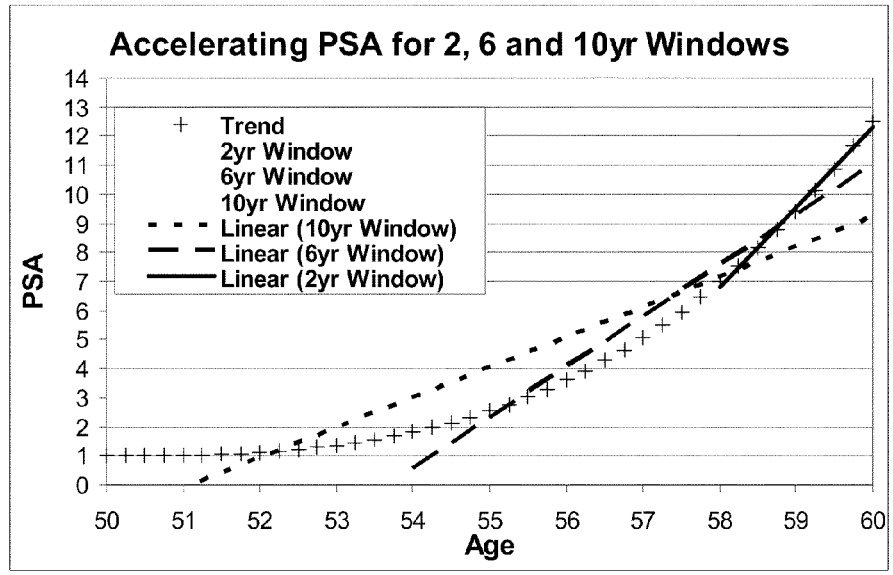
FIG. 20 shows that reducing the estimation window from ten years to six years reduces the underestimation of PSA at age 60 to about 1.4 PSA (12.5 actual minus 11.1 for the linear trend).

The estimate of current PSA at age 60 can be improved by shortening the window over which the linear trend is estimated. The dashed line on FIG. 20 shows that reducing the estimation window from ten years to six years reduces the underestimation of PSA at age 60 to about 1.4 PSA (12.5 actual minus 11.1 for the linear trend). The solid line on FIG. 20 shows that reducing the estimation window from six years to two years further reduces the underestimation of PSA at age 60 to less than 0.1 PSA (12.5 actual minus more than 12.4 for the linear trend).

Figure 21:
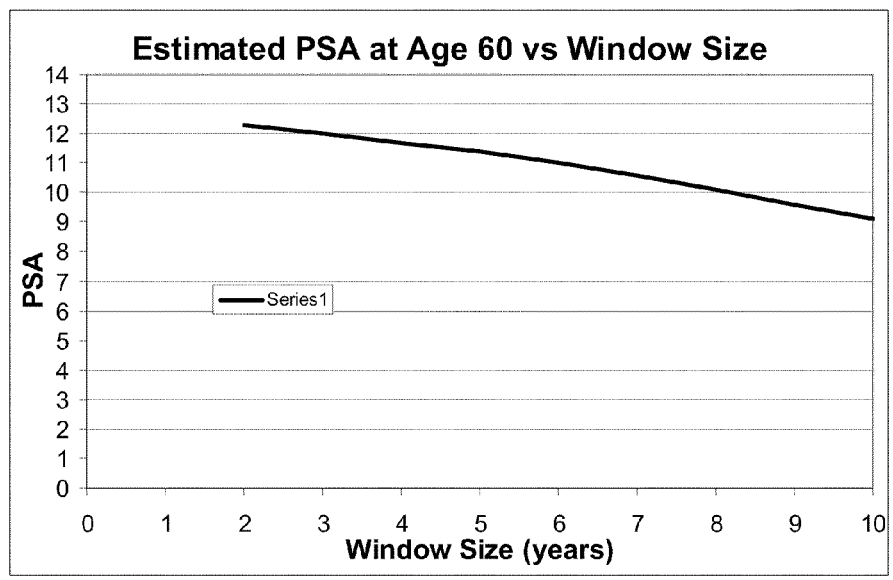
FIG. 21 plots an example of estimated PSA at age 60 and a decline at an accelerating rate as the estimation window size increases.

FIG. 21 plots an example of estimated PSA at age 60 and a decline at an accelerating rate as the estimation window size increases.

Increasing the window size can increase the number of tests considered and the length of time over which they are considered. More tests over a longer time can stabilize the trend and reduce the standard deviation in the estimate of current PSA at age 60 caused by random variation in the PSA test results. The example of FIG. 22 shows how the standard deviation of the estimate of current PSA at age 60 declines as window size increases.

Figure 22:
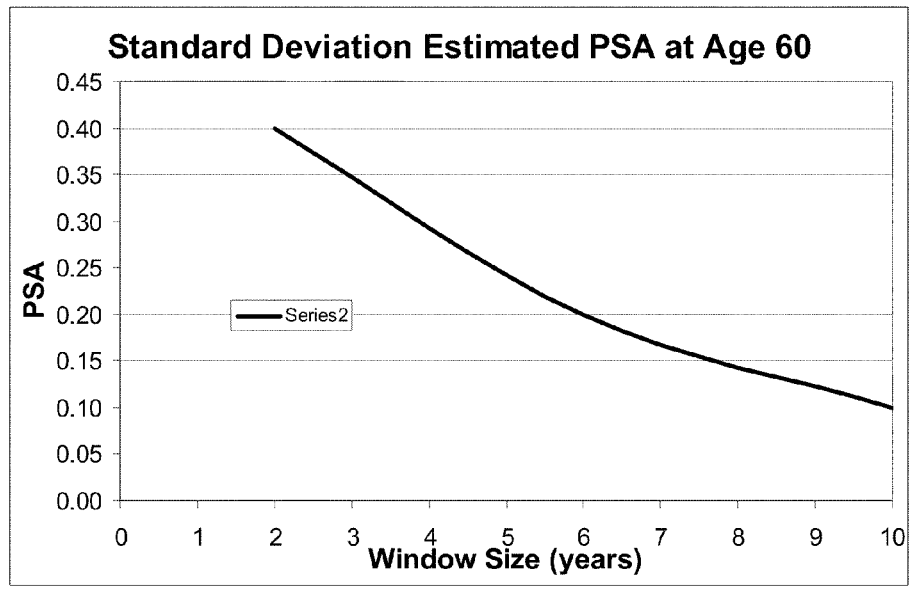
FIG. 22 shows exemplary how the standard deviation of the estimate of current PSA at age 60 declines as window size increases.
Figure 23:
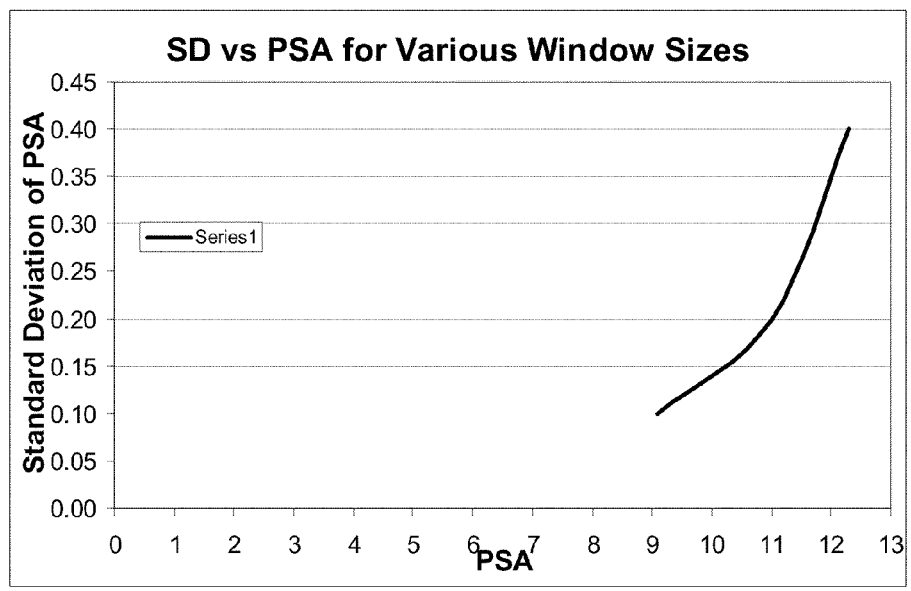
FIG. 23 combines the results shown on FIG. 21 and FIG. 22.

FIG. 23 combines the results shown on FIG. 21 and FIG. 22. The standard deviation of current PSA is plotted against the corresponding estimate of current PSA. The results for a ten year window are shown at the bottom left of the curve, and the results for a two year window are shown at the top right of the curve. The steep slope near the top right of the curve suggests that increasingly short windows provide very little benefit in terms of an increase in estimated PSA but lead to increasing costs in terms of steeply increasing standard deviations.

Figure 24:
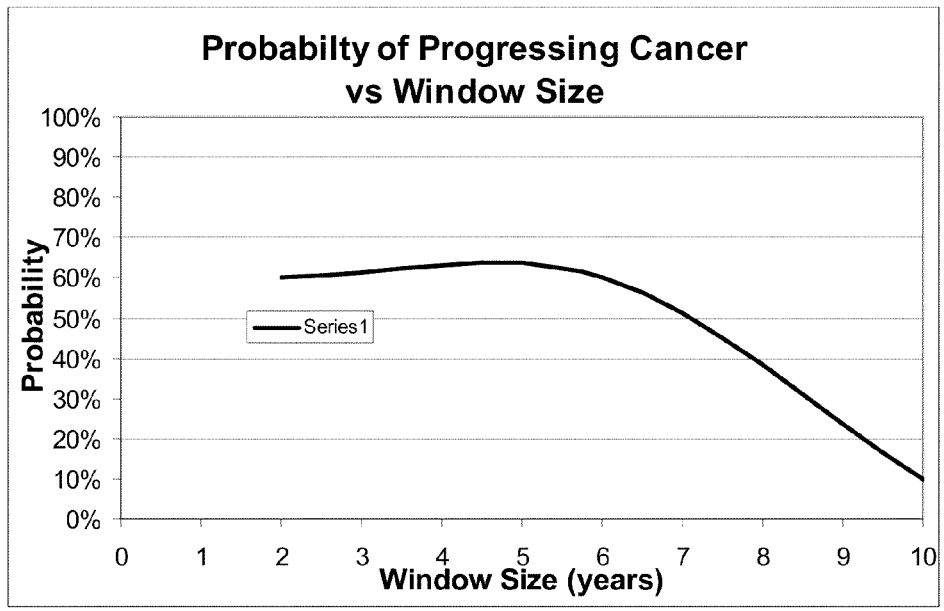
FIG. 24 shows a calculation of the probability of progressing cancer as a function of window size.

In an embodiment, a Bayesian probability of progressing cancer can depend on both current estimates of the trends and on the confidence in them. A higher PSA leads to a higher probability if all other variables remain unchanged. In contrast, a higher standard deviation leads to a lower probability if all other variables remain unchanged because there is less confidence in the estimate of current PSA. Changing window size may either increase or decrease the probability of progressing cancer. For example, a reduction in widow size will increase the estimate of PSA, which will increase the probability, but a reduction in window size will increase the standard deviation, which will decrease the probability. The outcome for probability depends on which of these two effects is stronger. FIG. 24 shows a calculation of the probability of progressing cancer as a function of window size. At the right, the window size is a large ten years, and the probability is low because the correspondingly low PSA estimate dominates. The probability increases as the window size decreases from ten years to about five years, where the maximum probability is reached. Further reductions in window size from five years to two years cause the probability to decrease gradually as the cost of increasing standard deviation outweighs the benefit of increasing PSA estimates.

Figure 25:
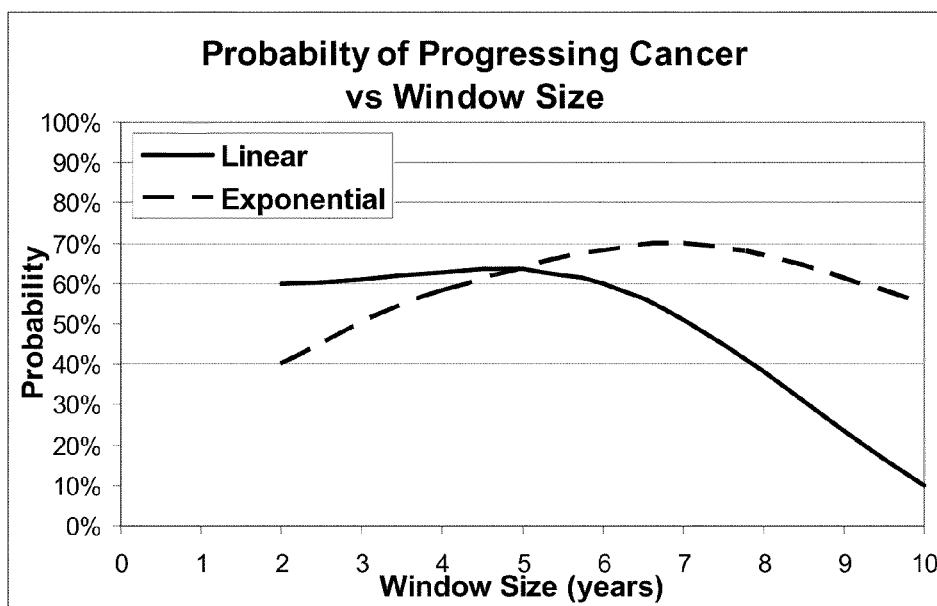
FIG. 25 illustrates the results of an exemplary linear function for estimating the PSA trend.

In these examples, a linear function for estimating the PSA trend has been considered. These results are shown as the solid curve on FIG. 25. FIG. 20 shows how the linear function does an increasingly poor job of matching a curved trend as the window size increases. Dynamic screening can use higher order functions to match curved trends more closely. An exponential function is the preferred higher order function because on average progressing cancer accelerates in an exponential fashion, but other higher order functions can be used. Higher order functions, like an exponential function, provide better fits of curved trends at the expense of higher standard deviations. Standard deviations are higher because the increased degrees of freedom make the trend estimates more sensitive to uncertainty in the test results. The dashed curve on FIG. 25 shows for an exponential function a calculation of the probability of progressing cancer as a function of window size. At the left, the window size is a small two years, and the probability is relatively low because the cost of a large standard deviation outweighs the benefit of a large PSA estimate. The probability increases as the window size increases from two years to about seven years, where the maximum probability is reached. Increased window size increases probability because of the benefit of decreasing standard deviation at little cost from minimally decreasing PSA estimate. Further increases in window size from seven years to ten years cause the probability to decrease gradually as the cost of increasing standard deviation outweighs the benefit of increasing PSA estimates.

Test frequency and the length of the test period help determine which trend function produces the maximum probability of progressing cancer. On FIG. 25 for when seven to ten years of test results are available the maximum probability is reached using the exponential function (dashed line) with a window size of seven years. With five to seven years of test results the maximum probability is reached using the exponential function (dashed curve) and the maximum window size available (equal to the length of the test period). With less than five years of tests results the maximum probability is reached using the linear function (solid curve) and the maximum window size available (equal to the length of the test period).

Figure 26:
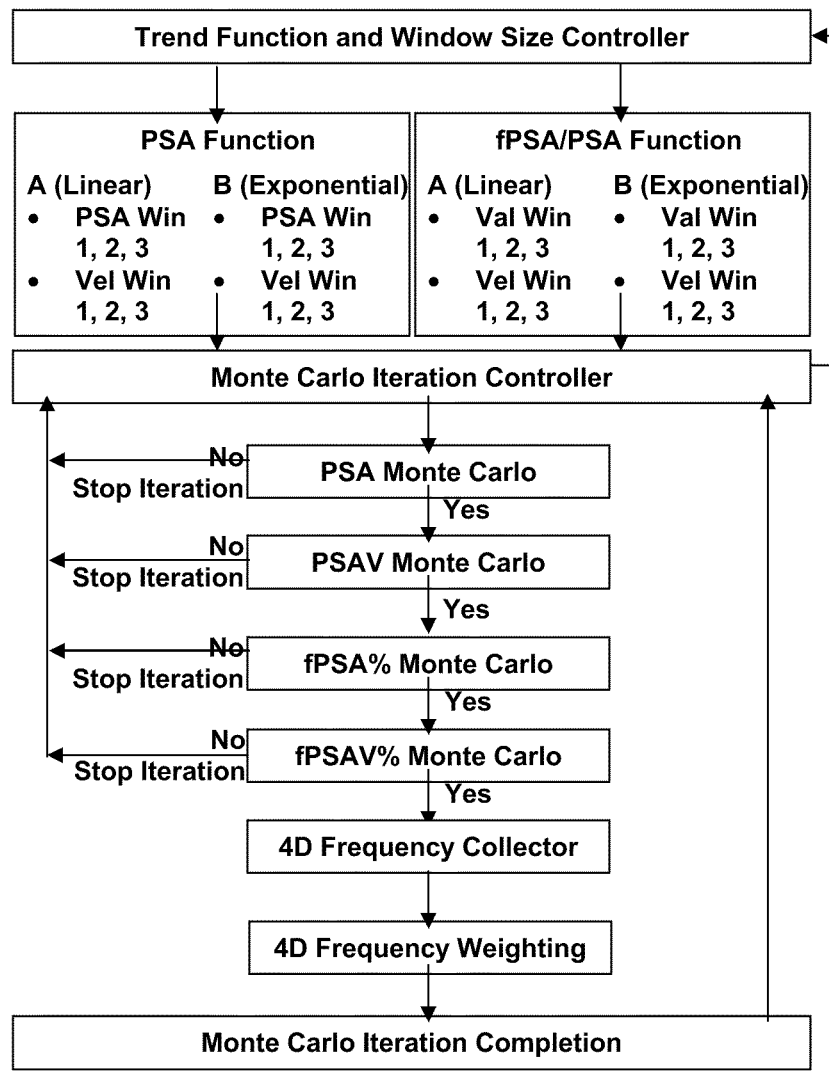
FIG. 26 and FIG. 27 show how variable trend functions and window sizes can be added to the no cancer four dimensional frequency generator and the cancer plus no cancer four dimensional frequency generator.
Figure 27:
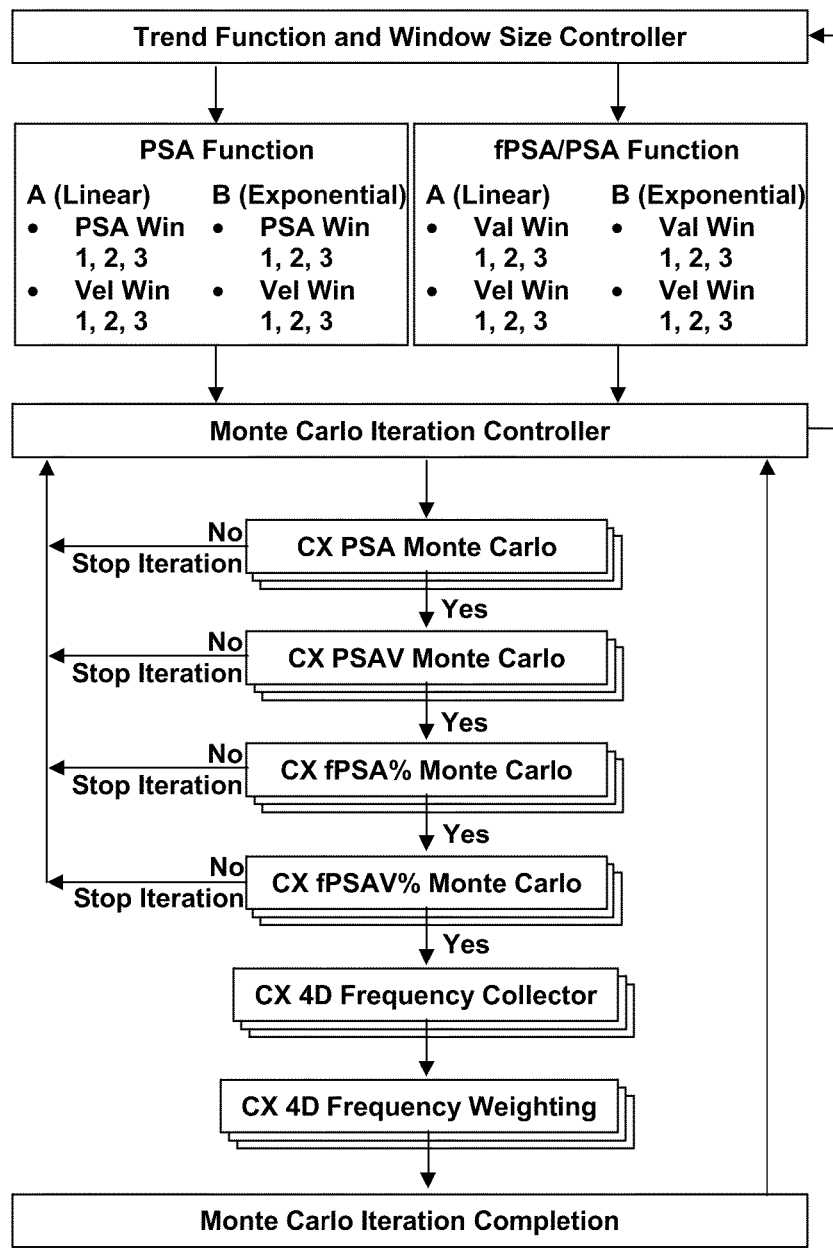

FIG. 26 and FIG. 27 show how variable trend functions and window sizes can be added to the no cancer four dimensional frequency generator and the cancer plus no cancer four dimensional frequency generator. The trend Function and Window Size Controller determines the combination of functions and window sizes used for each run of the Monte Carlo No Cancer Four Dimensional Frequency Generator and No Cancer Four Dimensional Frequency Generator, turns control over the Frequency Generator to run a series of Monte Carlo iterations and finally keeps track of the results returned. The trend function is used to estimate current PSA and PSAV and the often different window sizes for PSA and PSAV. The trend function is used to estimate current PSA, PSAV, FPSA and FPSAV needed to calculate an estimate of current fPSA % and FPSAV % and the often different window sizes for fPSA % and fPSAV %. The trend Function and Window Size Controller continues to vary combinations of functions and window sizes until enough have been run to determine the maximum probability with reasonable accuracy.

It can take a large amount of time to run the dynamic screening system for a sufficiently wide range of combinations of functions and window sizes. Some time can be saved by reducing the number of iterations for each Monte Carlo run. However, reducing iterations increases the risk that only a small number of hits will be detected in the bucket. A small number of hits can make the probability of progressing overly sensitive to random hits. This sensitivity can be reduced by the 4D Frequency Weighting in Module. Hits detected in the bucket are weighted by a function of the 4D distance from the observed values at the center of the bucket. Hits at the center are weighted most highly, and hits farther away are less heavily weighted. The weighting function reduces the impact of near misses and marginal hits and reduces the sensitivity of progressing cancer to them. The weighting function can take the following form:

$Wfn(\Delta)$=the greater of $O$ and $1-c*\Delta$, where $c$ is a constant $\Delta=(n\Delta PSA^2+n\Delta PSAV^2+n\Delta fPSA\%^2+n\Delta fPSAV\%^2)^{0.5}$ $n\Delta PSA=(PSA-tPSA)/nPSA$ where tPSA is the current value of the trend PSA
where nPSA is a normalizing PSA (possibly=tPSA)

$n\Delta PSAV=(PSAV-tPSAV)/nPSAV$ where tPSAV is the current value of the trend PSAV
where nPSAV is a normalizing PSA (possibly=tPSAV)

$n\Delta fPSA\%=(fPSA\%-tfPSA\%)/nfPSA\%$ where tfPSA % is the current value of the trend fPSA %
where nfPSA % is a normalizing fPSA % (possibly=tfPSA %)

$n\Delta fPSAV\%=(fPSAV\%-tfPSAV\%)/nfPSAV\%$ where tfPSAV % is the current value of the trend fPSAV %
where nfPSAV % is a normalizing fPSAV % (possibly=tfPSAV %)

Figure 28:
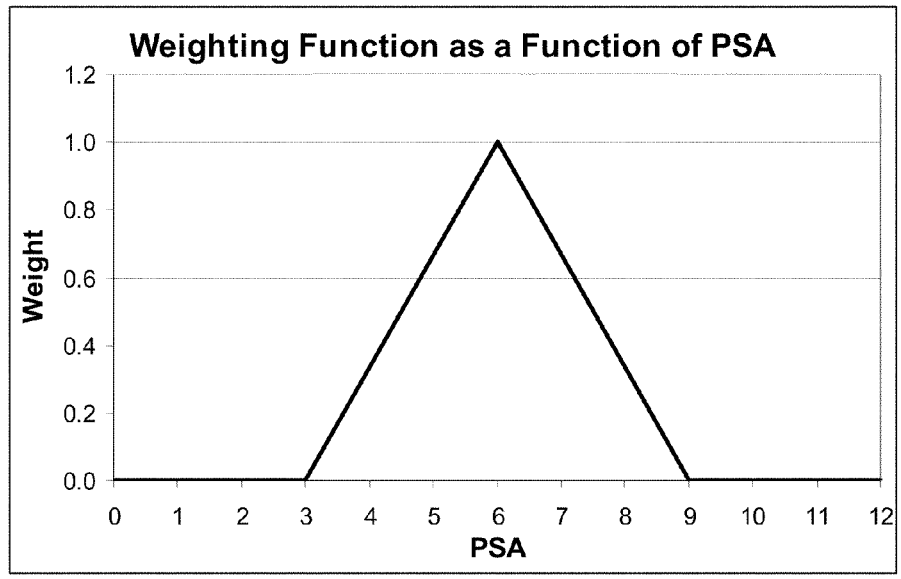
FIG. 28 shows an example of this triangle weighting function as a function of PSA.

FIG. 28 shows an example of this triangle weighting function as a function of PSA. The weight is 0 for PSA from 0 to 3. The weight increases linearly from 0 at PSA 3 to 1 at PSA 6. The weight decreases linearly from 1 at PSA 6 to 0 at PSA 9. The weight is 0 for PSA greater than 9.

Figure 29:
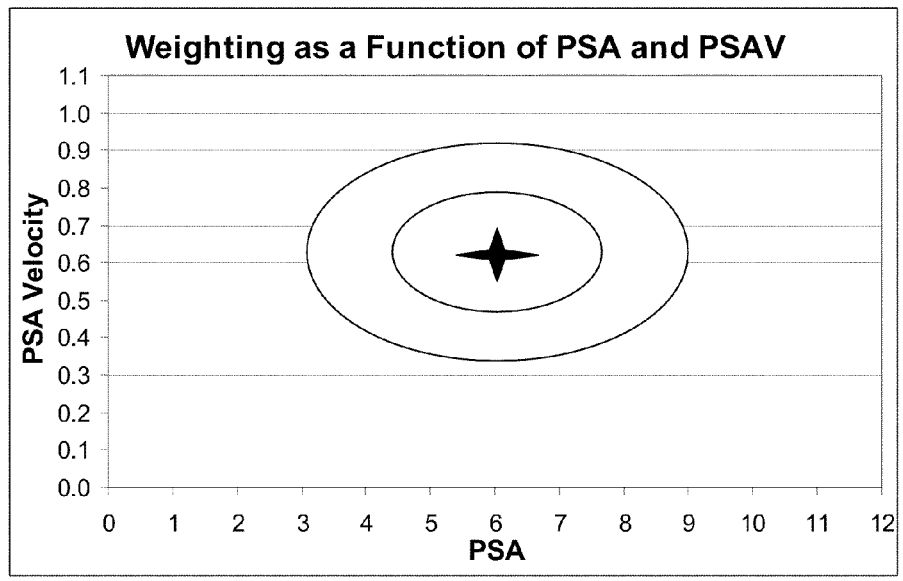
FIG. 29 shows an example of a weighting function as a function of PSA and PSA velocity.

FIG. 29 shows an example of a weighting function as a function of PSA and PSA velocity. The weight is 1 at PSA of 6 and PSAV of 0.6, shown by the star. The weight drops to zero at the outer oval centered on the star. Corresponding weighting functions can be constructed for three dimensions, four dimensions or more dimensions.

Figure 30:
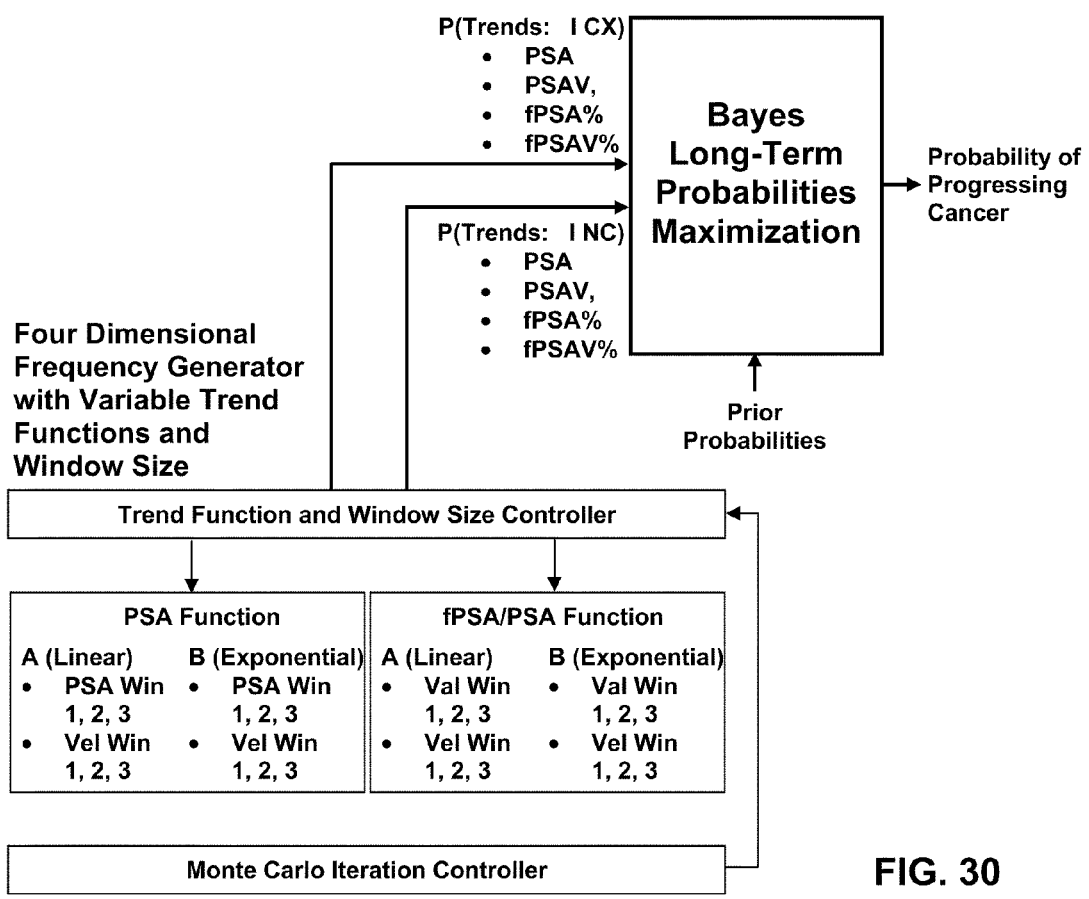
FIG. 30 shows an exemplary Maximum Probability Bayes system.

An exemplary Maximum Probability Bayes system is shown on FIG. 30. The trend Function and Window Size Controller generates four dimensional frequency distributions for no cancer and cancer plus no cancer cases for an appropriate variety of trend functions and window sizes, as shown by FIG. 26 and FIG. 27. The corresponding conditional probabilities are fed to the Bayse Long-Term Probabilities Maximization module. The maximum probability can be estimated and the corresponding functions and window sizes using one or more of a variety of techniques that can include design of experiments, response surface methods, analytic optimization, hill climbing optimization and any other methods that may be effective.

Figure 31:
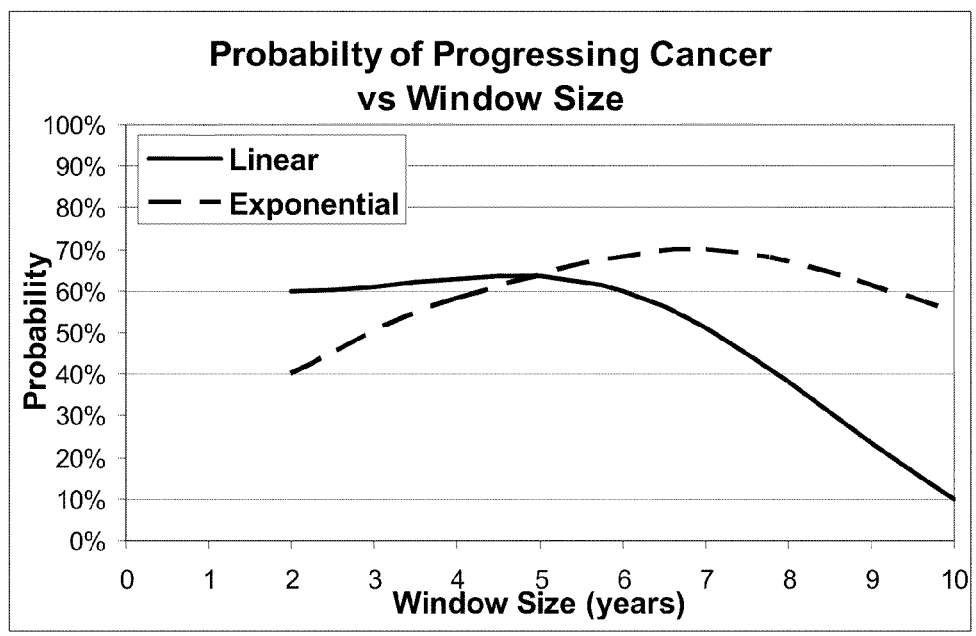
FIG. 31 shows how the results that can be observed for both PSA only using analytic optimization (the curve maximum for each curve) using one dimensional response surfaces (the curves).

For example, FIG. 31 shows how the results that can be observed for both PSA only using analytic optimization (the curve maximum for each curve) using one dimensional response surfaces (the curves). Maximum probability is reached using the linear function (solid curve) and maximum window size for test periods from two to five years. It is reached using the exponential function (dashed curve) for test periods greater than five years with maximum window size for test periods from five to seven years and a seven year window size for longer test periods.

Figure 32:
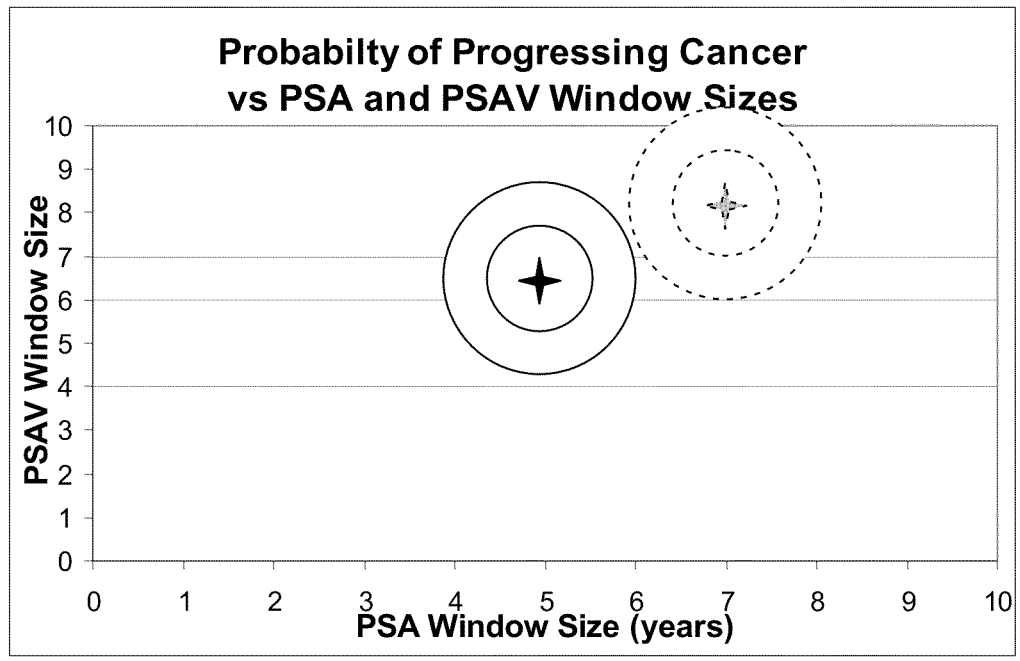
FIG. 32 shows how the results can be observed for both PSA and PSA velocity.

FIG. 32 shows how the results that can be observed for both PSA and PSA velocity. The window size for PSA is shown on the horizontal axis. The window size for PSAV is shown on the vertical axis. Probability is perpendicular to the page and represented as a contour map. The star shows the location of the maximum probability. The two circles around the star show contours of lower probability with the lowest probability shown by the largest circle. These contour maps can be constructed using two dimensional quadratic response surfaces, and the maximums can be found using analytic maximization. In this case, and in many cases, maximum probability is reached using different window sizes for different variables. Moreover, the window sizes that produce the maximum probability are likely to vary as a result of variation in the number of tests, total testing period, the amount of cancer progression and the curvature of the PSA trend, the functional form chosen, and a variety of other variables and circumstances.

Figure 33:
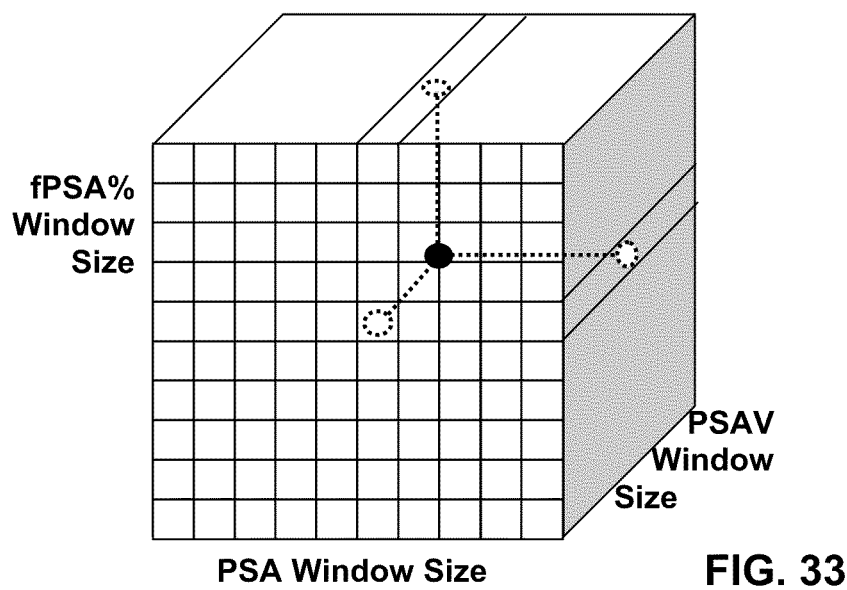
FIG. 33 shows an exemplary concept of maximum probability and window sizes in a 3D situation and suggests how it can work in 4D or higher situations.

FIG. 33 shows an exemplary concept of maximum probability and window sizes in a 3D situation and demonstrates its function in 4D or higher situations.

Embodiments of the present invention extend the capabilities of dynamic screening. The capabilities relate to multiple benign conditions as well as progressing cancer. Included are descriptions covering temporary benign conditions, long-term conditions, both benign and cancer, and tuning distributions using long-term conditions as the example.

PSA and free PSA tests can have results that are greater than or smaller than their predicted trend values. Dynamic screening may label them anomalous and excludes them from subsequent trend estimation if their deviations, including the ratio free PSA to PSA, exceed certain tolerance ranges. Anomalous results with PSA values substantially below the trend are rare and may be caused by a variety of situations, including test error or test recording error. Anomalous results with PSA values substantially above the trend are more frequent and may be caused by one or more benign conditions. Dynamic screening estimates the probability of these benign conditions using Bayesian processes.

Plurality of Medical Conditions

Figure 34:
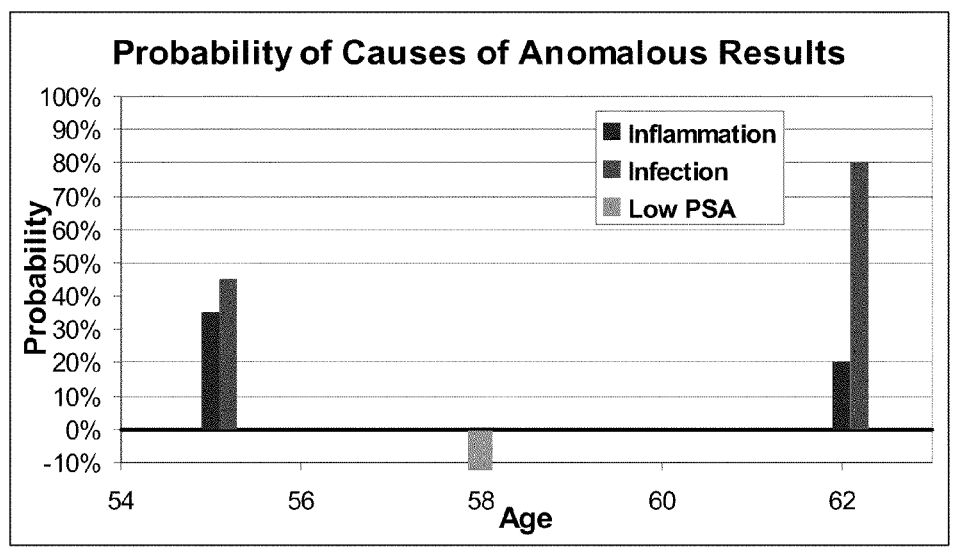
FIG. 34 shows the probability of each of these two temporary benign conditions for anomalous test results over time for a man.

In an embodiment, capabilities are added to dynamic screening to allow the calculation of the probability of benign prostate conditions. Two exemplary conditions include, but are not limited to, inflammation prostatitis and infection prostatitis along with a category for other temporary conditions. FIG. 34 shows the probability of each of these two temporary benign conditions for anomalous test results over time for a man. These probabilities can be used to inform decisions about imaging, testing and treatment of possible conditions. Anomalous test results with PSA values below the trend are indicated by gray bars below the horizontal axis.

Three similar Bayes processes can be used to calculate the probability of the prostate conditions: inflammation prostatitis, infection prostatitis and other temporary conditions. The process for calculating the probability of progressing cancer has been disclosed previously. In an embodiment, the Bayes process uses three elements: the prior probability of the condition, the probability of the observed trend values and the incremental change from them conditional on all conditions and the probability of the observed trend values and the incremental change from them conditional on the absence of the condition but with all other conditions possible. Prior probabilities may be a function of age, race, genetics, demographics, past experience with the conditions and other considerations as shown in FIG. 35.

Figure 36:
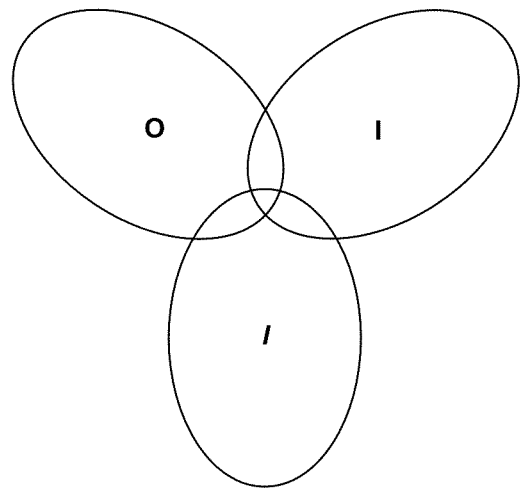
FIG. 36 shows temporary conditions of the prostate are partitioned into 7 different condition combinations that are composed of three different prostate conditions.

Temporary conditions of the prostate are partitioned into 7 different condition combinations that are composed of three different prostate conditions as shown in FIG. 36. This partition allows the use of an extension of Bayes theorem for a partition of the event space—all relevant long-term prostate conditions in this case.

Definitions

Xi=Any one of several prostate conditions, such as O, I, I.
Xj=One specific prostate condition, such as O or I or I.
Yi=Any one of several condition partitions, such as O, OI, OII.
Yj=One specific condition partition, such as O or OI or OII.
Pr(Yj)=Prior probability of condition partition Y.
P(R|Yj)=Conditional probability of results (R) given condition partition) Y.
P(Yj|R=Conditional probability of condition partition Y given results) (R).
P(Xj|R=Conditional probability of condition X given results (R).)

Equations $$P(Yj \mid R) = \frac{Pr(Yj) * P(R \mid Yj)}{\sum Pr(Yi) * P(R \mid Yi) \text{ summed over all } Y \text{ is}},$$

for example:

$$P(OII \mid R) = \frac{Pr(OII) * P(R \mid OII)}{\sum Pr(Yi) * P(R \mid Yi) \text{ summed over all } Y \text{ is}},$$

where:

$$\sum PR(Yi) * P(R \mid Yi) \text{ summed over all } Y \text{ is} =$$

$$Pr(O) * P(R \mid O) + Pr(I) * P(R \mid I) + Pr(I) * P(R \mid I) + Pr(OI) * P(R \mid OI) +$$

$$Pr(OI) * P(R \mid OI) + Pr(II) * P(R \mid II) + Pr(OII) * P(R \mid OII)$$

$$P(Xj \mid R) = \sum P(Yj \mid R) \text{ summed over all } Y \text{ is that contain } Xj, \text{ for}$$

example:

$$P(I \mid R) = P(I \mid R) + P(OI \mid R) + P(II \mid R) + P(OII \mid R)$$

The probability generator for all temporary prostate conditions consolidates output from three separate probability generators: inflammation prostatitis, infection prostatitis and other temporary conditions as shown in FIG. 37 and FIG. 38. Total values are stored from iterations of the Monte Carlo process for four variables: PSA and PSA increment from the trend, and free PSA and free PSA increment from the trend. Ratios are calculated for free PSA % (=free PSA/PSA) and free PSA Increment % (=free PSA increment/PSA increment). Other probability generators are similar with one module removed. For example, the other condition generator starts with the all temporary prostate conditions generator and removes the other conditions generator.

Figure 39:
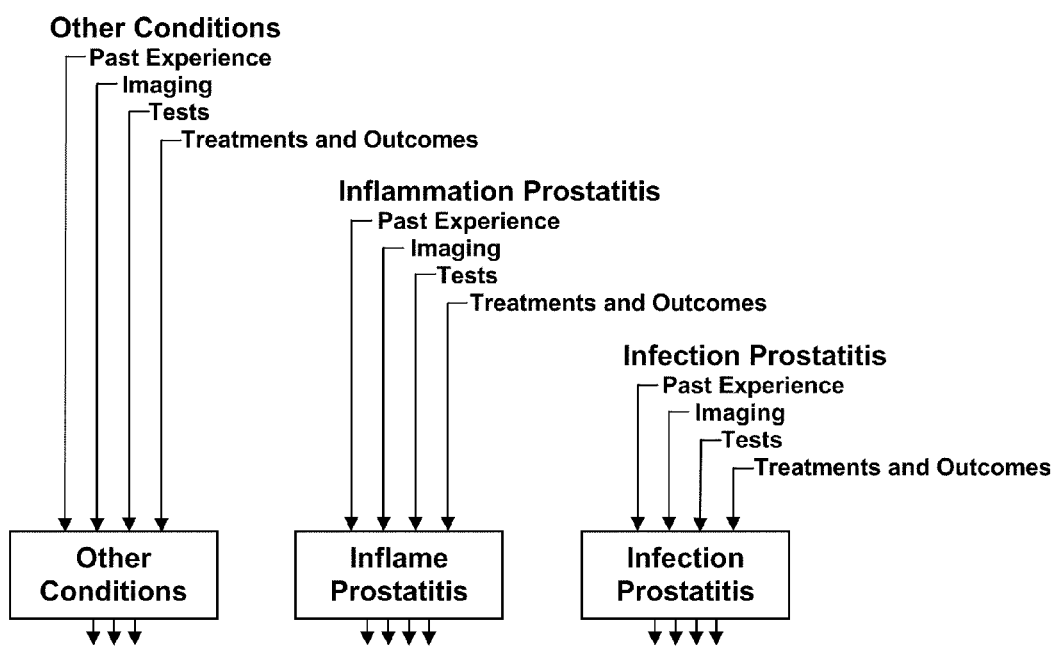
FIG. 39 shows how probability distributions of each prostate condition can be affected by past medical experience with the conditions, and the results of imaging, tests, treatment and other medical procedures.
Figure 40:
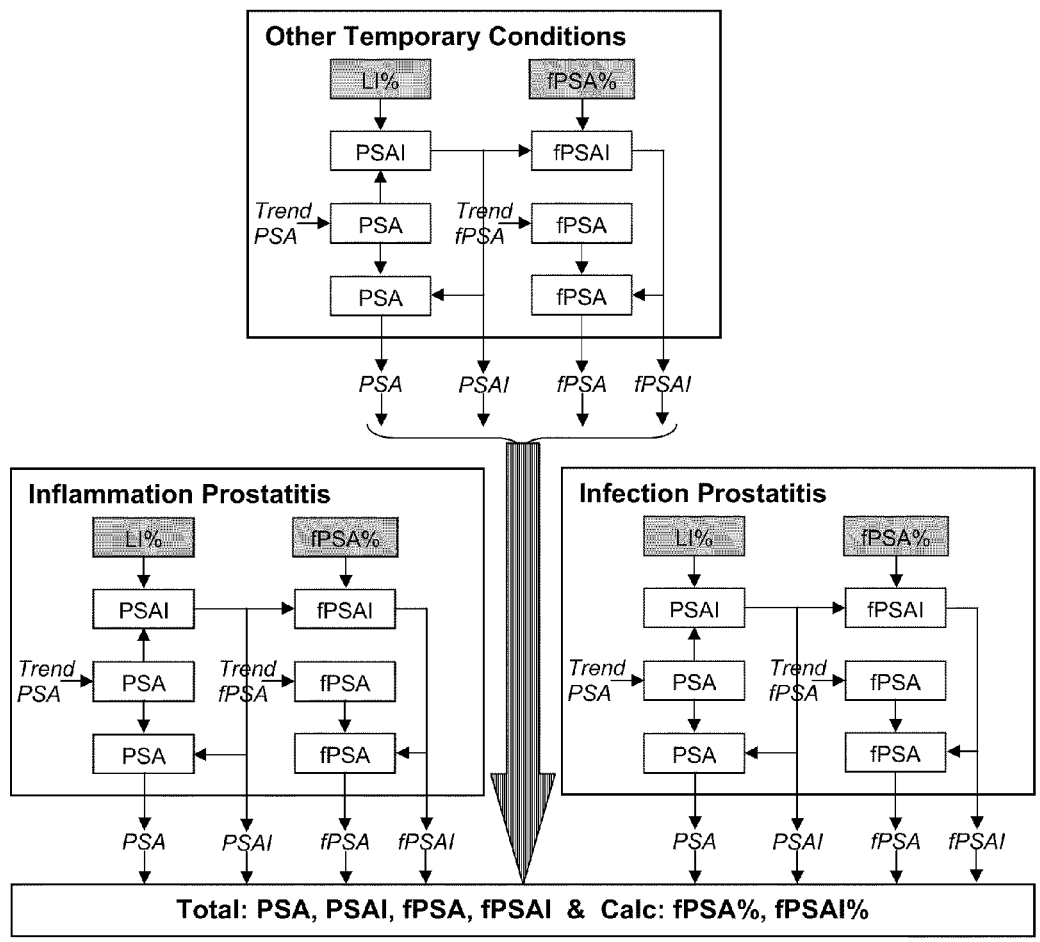
FIG. 40 shows, for example, a negative bacterial culture and no impact from antibiotic treatment may reduce the probability of infection prostatitis and increase the probability of inflammation and the probability of other conditions.

The probability distributions of each prostate condition can be affected by past medical experience with the conditions, and the results of imaging, tests, treatment and other medical procedures as shown in FIG. 39. For example, prostatic secretions can be cultured for bacterial infections. The results can affect the probability distributions produced by the infection prostatitis module. In a similar way, treatment with antibiotics can affect PSA levels. The outcome can affect the distributions produced by the infection prostatitis module. For example, a negative bacterial culture and no impact from antibiotic treatment may reduce the probability of infection prostatitis and increase the probability of inflammation and the probability of other conditions. In contrast, a positive bacterial culture and/or beneficial impact of antibiotic treatment may increase the probability of infection prostatitis to a high level and reduce the probability of inflammation and the probability of other conditions. Examples of this are shown in as shown in FIG. 40.

In an embodiment, other clinical conditions PSA increment is the product of the other conditions leak rate increment, drawn from the other conditions LI % distribution, and trend PSA from the PSA module as shown in FIG. 41. Temporary PSA is the sum of trend PSA from the PSA module and PSA increment. In other conditions, free PSA increment is the product of the other conditions free PSA %, drawn from the other conditions fPSA % distribution (which may be influenced by the healthy and BPH fPSA % s), and calculated PSA increment. Temporary free PSA is the sum of trend free PSA from the free PSA module and free PSA increment.

In an embodiment, inflammation PSA increment is the product of the inflammation leak rate increment, drawn from the inflammation LI % distribution, and trend PSA from the PSA module as shown in FIG. 41. Temporary PSA is the sum of trend PSA from the PSA module and PSA increment. Inflammation free PSA increment is the product of the inflammation free PSA %, drawn from the inflammation fPSA % distribution (which may be influenced by the healthy and BPH fPSA % s), and calculated PSA increment. Temporary free PSA is the sum of trend free PSA from the free PSA module and free PSA increment.

In another embodiment, infection PSA increment is the product of the infection leak rate increment, drawn from the infection LI % distribution, and trend PSA from the PSA module as shown in FIG. 41. Temporary PSA is the sum of trend PSA from the PSA module and PSA increment. Infection free PSA increment is the product of the infection free PSA %, drawn from the infection fPSA % distribution (which may be influenced by the healthy and BPH fPSA % s), and calculated PSA increment. Temporary free PSA is the sum of trend free PSA from the free PSA module and free PSA increment.

A total and calculation module can consolidate output from the separate probability generators for the three temporary prostate conditions: other temporary conditions, inflammation prostatitis, and infection prostatitis. Values are totaled for four variables: PSA and PSA increment, and free PSA and free PSA increment. Ratios are calculated for free PSA % (=free PSA/PSA) and free PSA increment % (=free PSA increment/PSA increment).

Figure 42:
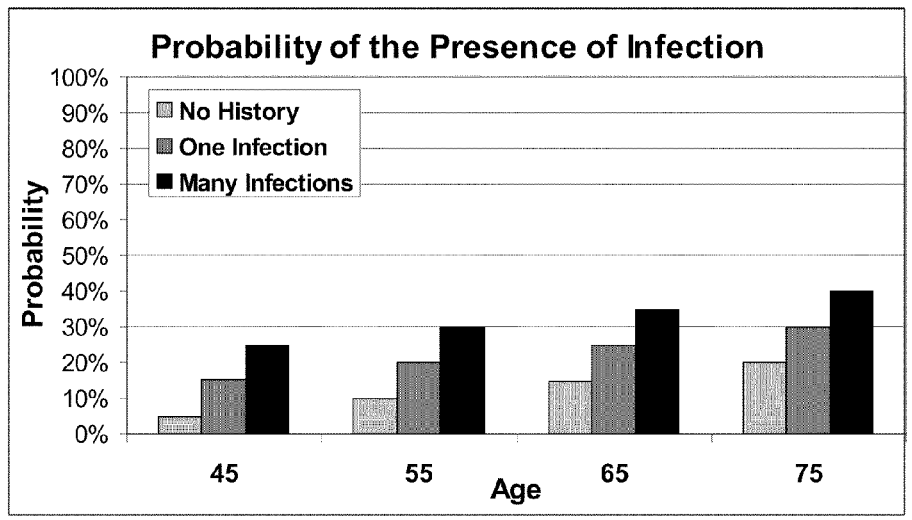
FIG. 42 shows an example of how the probability of the presence of infection (P %) for a man tends to increase with age and past history of infection.

The graph in FIG. 42 shows an example of how the probability of the presence of infection (P %) for a man tends to increase with age and past history of infection. The more a man has had past infections the more likely he is to have one now.

Figure 43:
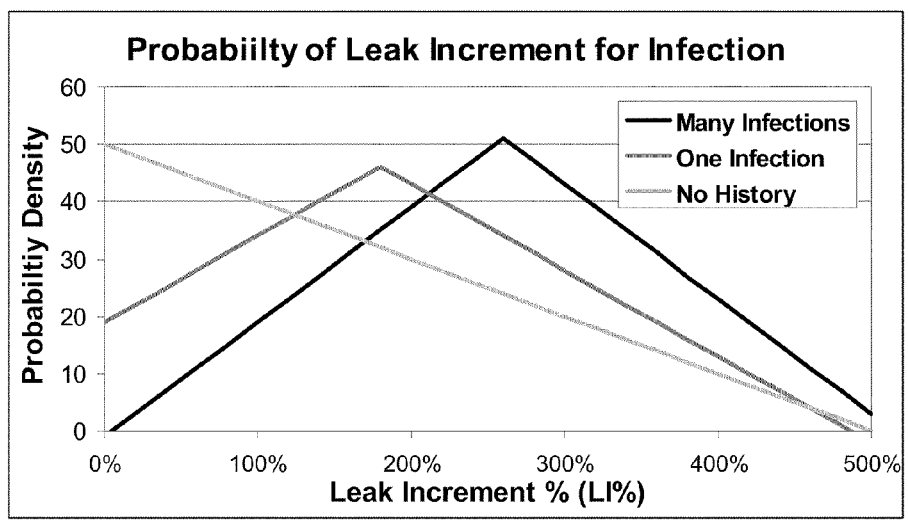
FIG. 43 shows the probability density for an infection leak increment percent (LI %) can depend on past experience.

The probability density for an infection leak increment percent (LI %) can depend on past experience as shown in FIG. 43. A man with no history of infections will have a declining population based distribution, shown in light gray. However, one or many infections with high LI % s will shift the distributions to higher peaks at larger LI % s, as shown by the dark gray and black distributions.

Figure 44:
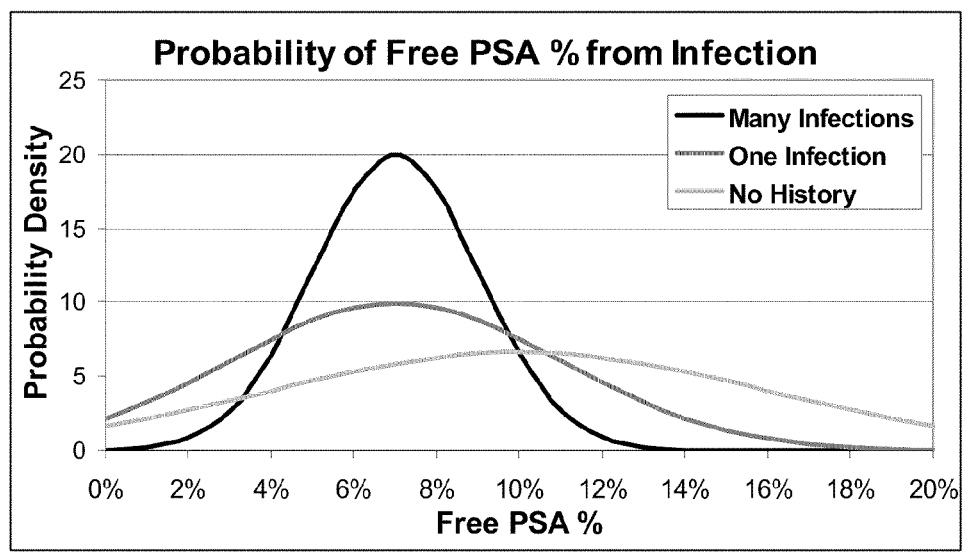
FIG. 44 shows the probability density for free PSA % (fPSA %) can also depend on past experience.

The probability density for free PSA % (fPSA %) can also depend on past experience as shown in FIG. 44. A man with no history of infections will have a low and broad population based distribution, shown in light gray. However, one or many infections with very low fPSA %s will shift the distributions to higher peaks at smaller fPSA %s, as shown by the dark gray and black distributions.

In an aspect, an elevated or increasing PSA trend is an indication that a long-term condition may be affecting the prostate. Dynamic screening can estimate the probability of these conditions using Bayesian processes.

Figure 45:
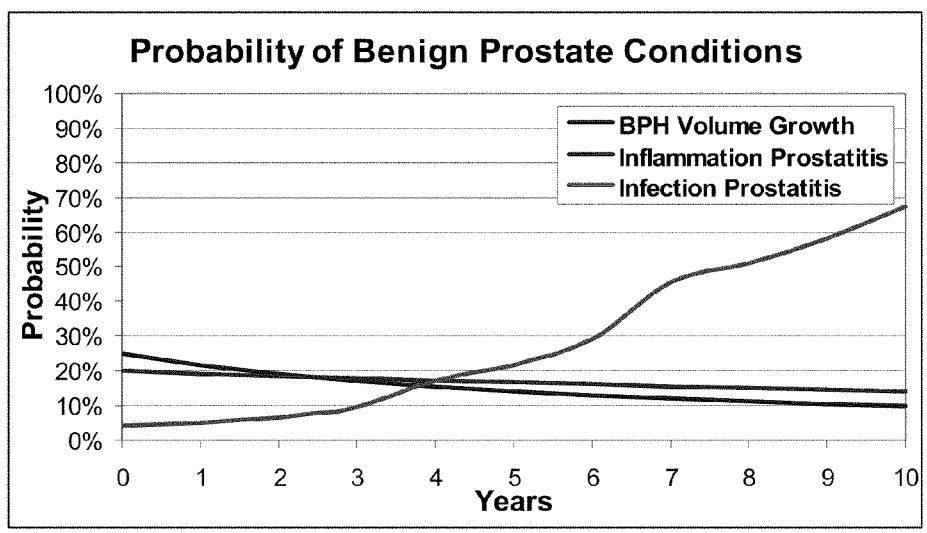
FIG. 45 shows how the probability of each of these three benign conditions can change over time for a man.

In an embodiment, probability of other long-term prostate conditions, in addition to progressing cancer, can be calculated. For example, long-term conditions considered include, but are not limited to, volume growth due to BPH, inflammation prostatitis and infection prostatitis. The exemplary graph in FIG. 45 shows how the probability of each of these three benign conditions can change over time for a man. These probabilities can be used to inform decisions about imaging, testing and treatment of possible conditions.

In another embodiment, four similar Bayes processes are used to calculate the probability of the prostate conditions: volume growth due to BPH, inflammation prostatitis, infection prostatitis and progressing cancer as shown in FIG. 46. The process for calculating the probability of progressing cancer has been disclosed previously. The Bayes process uses three elements: the prior probability of the condition, the probability of the observed trend values conditional on all conditions and the probability of the observed trend values conditional on the absence of the condition but with all other conditions possible. Prior probabilities may be a function of age, race, genetics, demographics and other considerations.

The status of the prostate is partitioned into 16 different condition combinations that are composed of five different prostate conditions as shown in FIG. 47. The condition combinations are mutually exclusive and collectively exhaustive. This partition allows the use of an extension of Bayes theorem for a partition of the event space—all relevant long-term prostate conditions in this case.

Definitions

Xi=Any one of several medical conditions, such as H, V, C.
Xj=One specific condition, such as H or V or C.
Yi=Any one of several condition partitions, such as H, HV, HVI/C.
Yj=One specific condition partition, such as H or HV or HVI/C.
Pr(Yj)=Prior probability of condition partition Y.
P(R|Yj)=Conditional probability of results (R) given condition partition Y.
P(Yj|R)=Conditional probability of condition partition Y given results (R).
P(Xj|R)=Conditional probability of condition X given results (R).

Equations $$P(Yj \mid R) = \frac{Pr(Yj) * P(R \mid Yj)}{\sum Pr(Yi) * P(R \mid Yi) \text{ summed over all } Y \text{ is}},$$

for example:

$$P(HVC \mid R) = \frac{Pr(HVC) * P(R \mid HVC)}{\sum Pr(Yi) * P(R \mid Yi) \text{ summed over all } Y \text{ is}},$$

where:

$\sum Pr(Yi) * P(R \mid Yi)$ summed over all $Y$ is =

$Pr(H) * P(R \mid H) + Pr(HV) * P(R \mid HV) + Pr(HI) * P(R \mid HI) +$ $Pr(HI) * P(R \mid HI) + Pr(HC) * P(R \mid HC) + Pr(HVI) * P(R \mid HVI) +$ $Pr(HVI) * P(R \mid HVI) + Pr(HVC) * P(R \mid HVC) +$ $Pr(HII) * P(R \mid HII) + Pr(HIC) * P(R \mid HIC) +$ $Pr(HIC) * P(R \mid HIC) + Pr(HVII) * P(R \mid HVII) +$ $Pr(HVIC) * P(R \mid HVIC) + Pr(HVIC) * P(R \mid HVIC) +$ $Pr(HIIC) * P(R \mid HIIC) + Pr(HVIIC) * P(R \mid HVIIC)$ $P(Xj \mid R) = \sum P(Yj \mid R)$ summed over all $Y$ is that contain $Xj$, for example:

$P(H \mid R) = P(H \mid R)$ $P(V \mid R) = P(HV \mid R) + P(HVI \mid R) + P(HVI \mid R) + P(HVC \mid R) +$ $P(HVII \mid R) + P(HVIC \mid R) + P(HVIC \mid R) + P(HVIIC \mid R)$ $P(C \mid R) = P(HC \mid R) + P(HVC \mid R) + P(HIC \mid R) +$ $P(HIC \mid R) + P(HVIC \mid R) + P(HVIC \mid R) + P(HIIC \mid R)$ In an aspect of the invention, a probability generator for all prostate conditions consolidates output from five exemplary separate probability generators for a healthy prostate and the four prostate that include without limitation: volume growth due to BPH, inflammation prostatitis, infection prostatitis and progressing cancer as shown in FIG. 48, FIG. 49, and FIG. 50. Total values are stored from iterations of the Monte Carlo process for six exemplary variables that include without limitation: prostate volume and volume velocity, PSA and PSA velocity, and free PSA and free PSA velocity. Ratios can be calculated for free PSA % (=free PSA/PSA) and free PSA velocity % (=free PSA velocity/PSA velocity). In an embodiment, other probability generators can be similar with one module removed. For example, the no BPH volume growth generator starts with the all prostate conditions generator and removes the BPH volume growth generator.

Figure 51:
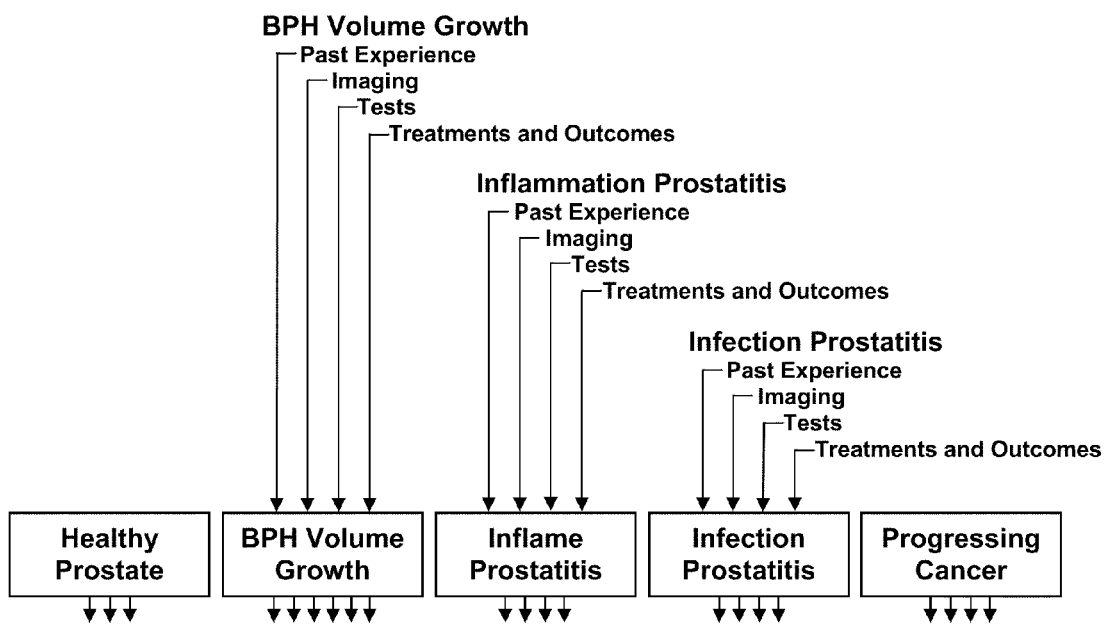

The probability distributions of each prostate condition can be affected by past experience and the results of imaging, tests, treatment and other medical procedures as shown in FIG. 51. For example, the prostate can be imaged using ultrasound or MRI equipment and its volume can be measured from the images. This measurement constrains the distributions of prostate volume, PSA and free PSA. For example, prostatic secretions can be cultured for bacterial infections. The results will affect the probability distributions produced by the infection prostatitis module. In a similar way, treatment with antibiotics can affect PSA levels. The outcome can affect the distributions produced by the infection prostatitis module. For example, a negative bacterial culture and no impact from antibiotic treatment will reduce the probability of infection prostatitis and increase the probability of other conditions, including progressing cancer. In contrast, a positive bacterial culture and/or beneficial impact of antibiotic treatment will increase the probability of infection prostatitis to a high level and reduce the probability of other conditions, including progressing cancer.

Figure 52:
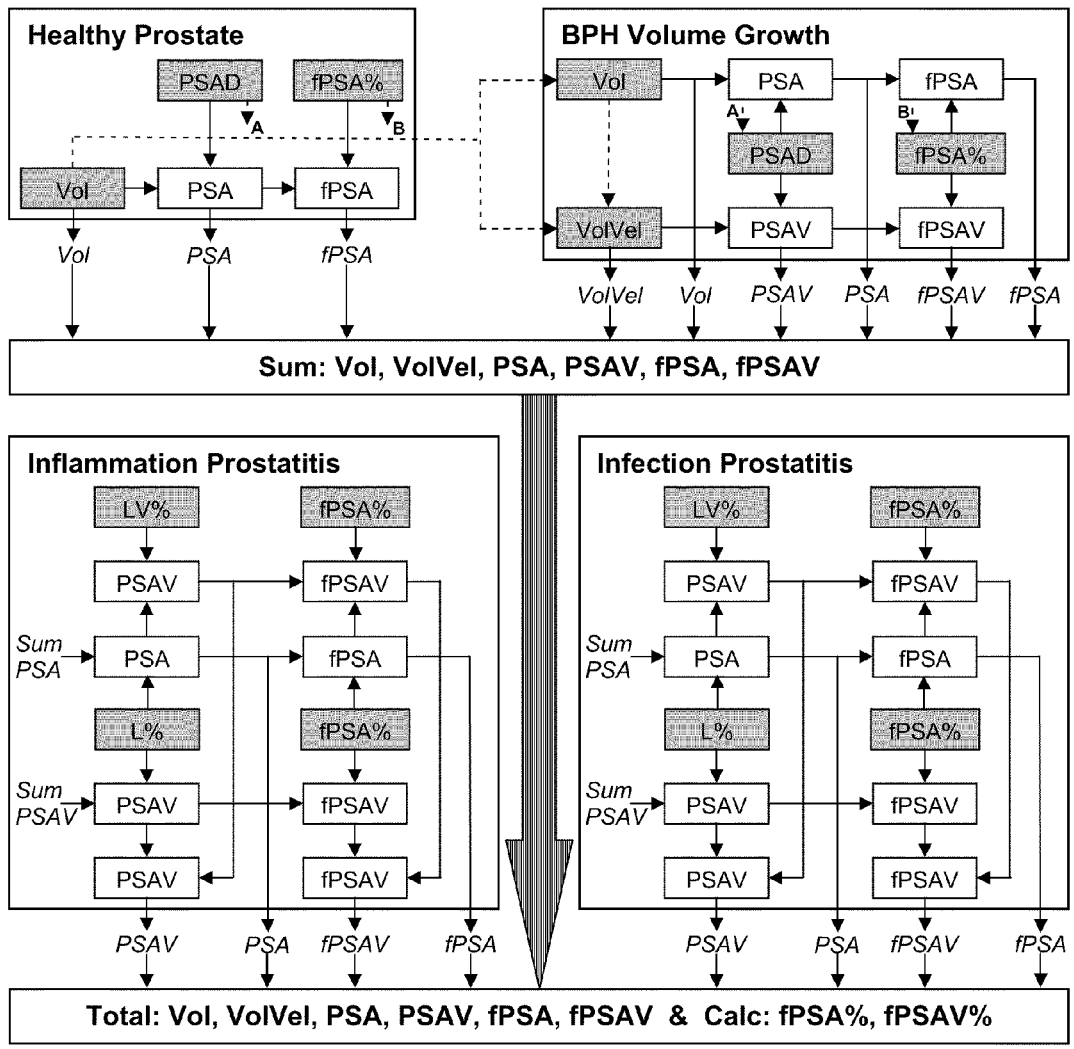
FIG. 52 shows an embodiment of the no cancer probability generators.

The flow charts in FIG. 52 show an embodiment of the no cancer probability generators. The small gray boxes show the probability distributions from which draws are made during each Monte Carlo iteration. In an embodiment, healthy prostate volume can be drawn from the Vol distribution. PSA is the product of PSA density, drawn from the healthy PSAD distribution, and the healthy prostate volume draw. Free PSA is the product of the free PSA %, drawn from the fPSA % distribution, and calculated PSA. In another embodiment, BPH volume is drawn from the Vol distribution, which may be influenced by the healthy Vol distribution as shown by the dotted line. BPH volume velocity is drawn from the VolVel distribution, which may be influenced by the healthy Vol distribution and the BPH Vol distribution, as shown by the dotted lines. PSA is the product of PSA density, drawn from the BPH PSAD distribution (which may be influenced by the healthy PSAD distribution as shown by the A connector), and the BPH prostate volume draw. PSA velocity is the product of PSA density, drawn from the BPH PSAD distribution (which may be influenced by the healthy PSAD distribution as shown by the A connector), and the BPH prostate volume velocity draw. Free PSA is the product of the free PSA %, drawn from the BPH fPSA % distribution (which may be influenced by the healthy fPSA % distribution as shown by the B connector), and calculated PSA. Free PSA velocity is the product of the free PSA %, drawn from the BPH fPSA % distribution (which may be influenced by the healthy fPSA % distribution as shown by the B connector), and calculated PSA velocity. A summation module can add healthy prostate and BPH volume growth variables: volume, volume velocity, PSA, PSA velocity, free PSA and free PSA velocity.

In an embodiment, inflammation prostatitis PSA is the product of the inflammation leak rate, drawn from the inflammation L % distribution, and Sum PSA from the summation module. PSA velocity has two sources. First, PSA velocity is the product of the leak rate velocity, drawn from the LV % distribution, which may be influenced by L %, and calculated inflammation PSA. Second, PSA velocity is the product of the leak rate, drawn from the inflammation L % distribution, and Sum PSA velocity from the summation module. Both sources of PSA velocity are summed in the module. Inflammation prostatitis free PSA can be the product of inflammation free PSA %, drawn from the inflammation fPSA % distribution (which may be influenced by the healthy and BPH fPSA % s), and calculated inflammation PSA. Free PSA velocity has two sources. First, free PSA velocity is the product of the free PSA %, drawn from the fPSA % distribution, and calculated inflammation PSA velocity (which came from the leak rate velocity %. Second, free PSA velocity is the product of the free PSA %, drawn from the inflammation fPSA % distribution, and calculated inflammation PSA velocity (which came from PSAV caused by volume velocity). Both sources of free PSA velocity are summed in the module.

Figure 56:
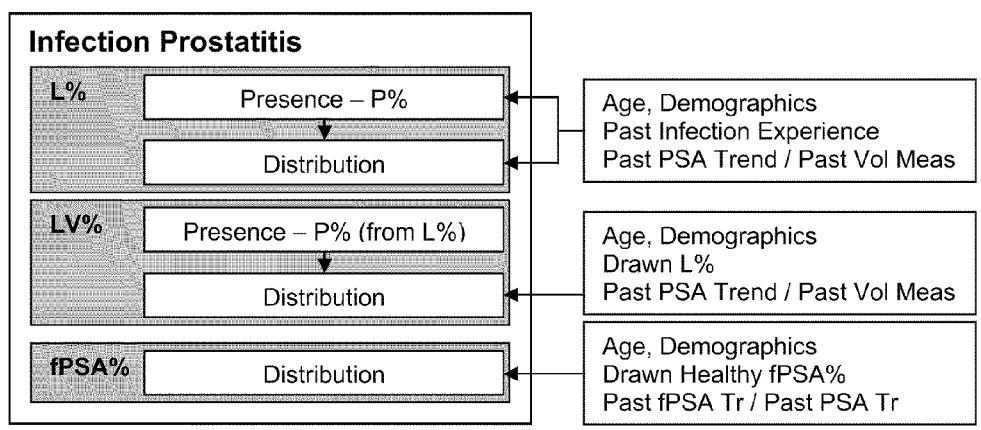
FIG. 56 shows an embodiment of an infection prostatitis module that has three distributions for Monte Carlo draws: L %, LV % and fPSA %.

In an embodiment, infection prostatitis PSA is the product of the infection leak rate, drawn from the infection L % distribution, and Sum PSA from the summation module as shown in FIG. 56. PSA velocity has two sources. First, PSA velocity is the product of the leak rate velocity, drawn from the LV % distribution, which may be influenced by L %, and calculated infection PSA. Second, PSA velocity is the product of the leak rate, drawn from the infection L % distribution, and Sum PSA velocity from the summation module. Both sources of PSA velocity are summed in the module. Infection prostatitis free PSA can be the product of infection free PSA %, drawn from the infection fPSA % distribution (which may be influenced by the healthy and BPH fPSA % s), and calculated infection PSA. Free PSA velocity has two sources. First, free PSA velocity is the product of the free PSA %, drawn from the fPSA % distribution, and calculated infection PSA velocity (which came from the leak rate velocity %). Second, free PSA velocity is the product of the free PSA %, drawn from the infection fPSA % distribution, and calculated infection PSA velocity (which came from PSAV caused by volume velocity). Both sources of free PSA velocity are summed in the module.

In an example, a total and calculation module consolidates output from the separate probability generators for the four benign prostate conditions: healthy prostate, volume growth due to BPH, inflammation prostatitis, infection prostatitis and progressing cancer. Values are totaled for six variables: prostate volume and volume velocity, PSA and PSA velocity, and free PSA and free PSA velocity. Ratios are calculated for free PSA % (=free PSA/PSA) and free PSA velocity % (=free PSA velocity/PSA velocity).

In an embodiment, a healthy prostate module has three distributions for Monte Carlo draws: Vol, PSAD and fPSA % as shown in FIG. 53. Vol is the healthy volume distribution from which a man's volume is drawn in each Monte Carlo iteration. It is affected by age, demographics and past volume measurements. An example for Vol is shown with a mean of 28.0 ccs and standard deviation of 4.3 ccs. PSAD is the healthy PSA density distribution from which a man's PSA density is drawn in each Monte Carlo iteration. It is affected by age, demographics and past PSA trends and volume measurements. An example for PSAD is shown with a mean of 0.035 PSA/cc and standard deviation of 0.008. fPSA % is the healthy free PSA % distribution from which a man's fPSA % is drawn in each Monte Carlo iteration. It is affected by age, demographics and past free PSA and PSA trends. An example for fPSA % is shown with a mean of 28% and standard deviation of 7%.

Figure 54:
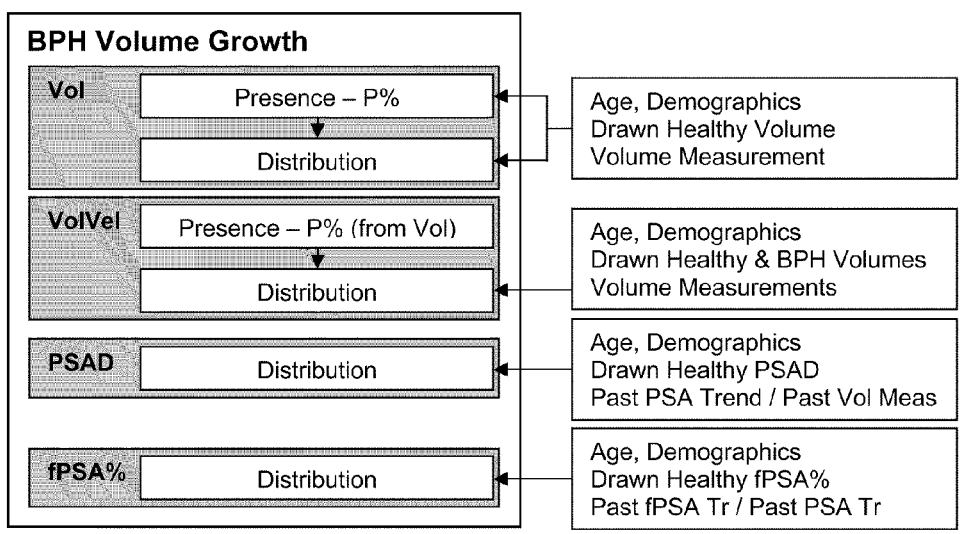
FIG. 54 shows an embodiment of a BPH volume growth module that has four distributions for Monte Carlo draws: Vol, VolVel, PSAD and fPSA %.

In an embodiment, the BPH volume growth module has four distributions for Monte Carlo draws: Vol, VolVel, PSAD and fPSA % as shown in FIG. 54. Vol is the BPH volume multiplier distribution from which a man's volume increase ratio to his healthy volume is drawn in each Monte Carlo iteration. Vol has two parts: the presence probability, P %, and the distribution of its values. P % is the binary probability that BPH is present and has caused an increase in the PSA trend. It is affected by age, demographics, the healthy volume draw and past volume measurements. P % is set equal to 100% for the certain module in the bold box. The distribution density function is likely to decline in density with increasing Vol. It may change based on past experience. VolVel is the BPH volume velocity distribution from which a man's volume velocity is drawn in each Monte Carlo iteration. VolVel is the annual rate of increase in prostate volume due to BPH. VolVel has two parts: the presence probability, P %, and the distribution of its values. P % is either 1 or 0 based on the P % draw in the Vol module. P % is set equal to 100% for the certain module in the bold box. The distribution density function is likely to decline in density with increasing VolVel. It may change based on age, demographics, drawn values for healthy and BPH volumes, and volume measurements. PSAD is the BPH volume PSA density distribution from which a man's BPH PSA density is drawn in each Monte Carlo iteration. It is affected by age, demographics, drawn healthy PSAD and past PSA trends and volume measurements. An example for PSAD is shown with a mean equal to the BPH % times the healthy PSAD draw and standard deviation of CV % times the mean. BPH % tends to roughly 100% because BPH density is similar to healthy density. fPSA % is the BPH volume growth free PSA % distribution from which a man's fPSA % is drawn in each Monte Carlo iteration. It is affected by age, demographics and past free PSA and PSA trends. An example for fPSA % is shown. It has a mean of BPH % times the drawn healthy fPSA %. Typically, BPH % is greater than 100% because BPH volume growth tends to increase free PSA %. CV % may be relatively small.

Figure 55:
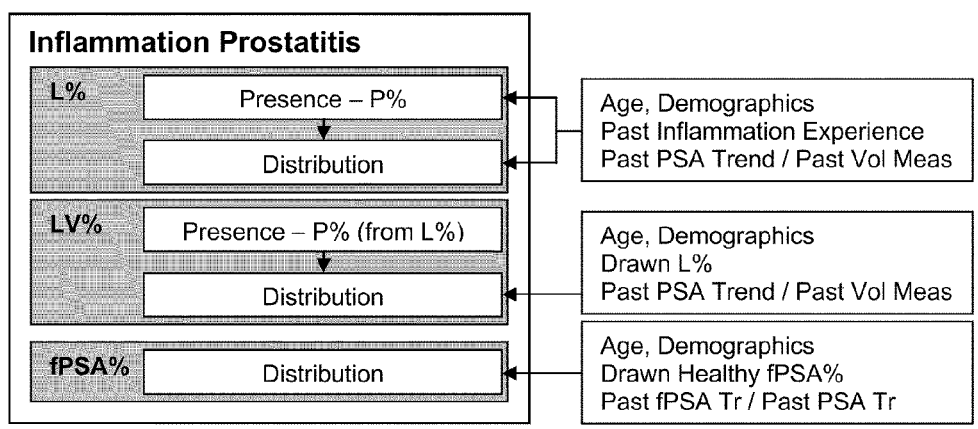
FIG. 55 shows an embodiment of an inflammation prostatitis module that has three distributions for Monte Carlo draws: L %, LV % and fPSA %.

In an embodiment, the inflammation prostatitis module has three distributions for Monte Carlo draws: L %, LV % and fPSA % as shown in FIG. 55. L % is the leak rate percent and has two parts: the presence probability, P %, and the distribution of its values. P % is the binary probability that inflammation is present and has caused an increase in the PSA trend. It is based on age, demographics and past experience with inflammation. P % is set equal to 100% for the certain module in the bold box. The distribution density function is likely to decline in density with increasing L %. It may change based on past experience. LV % is the leak rate velocity percent and describes how increasing inflammation increases the amount of PSA over time by leaking higher percentages of PSA. LV % has two parts: the presence probability, P %, and the distribution of its values. P % is either 1 or 0 based on the P % draw in the L % module. P % is set equal to 100% for the certain module in the bold box. The distribution density function is likely to decline in density with increasing LV %. It may change based on past experience. An example for fPSA % is shown with the mean equal to Inflammation % times the ratio of healthy plus BPH free PSA to PSA. Typically, Inflammation % is roughly 100% because inflammation tends to increase the amount of PSA leakage without changing the free PSA % substantially—resulting in a relatively small CV %.

In an embodiment, the infection prostatitis module has three distributions for Monte Carlo draws: L %, LV % and fPSA % as shown in FIG. 56. L % is the leak rate percent and has two parts: the presence probability, P %, and the distribution of its values. P % is the binary probability that infection is present and has caused an increase in the PSA trend. It is based on age, demographics and past experience with infection. P % is set equal to 100% for the certain module in the bold box. The distribution density function is likely to decline in density with increasing L %. It may change based on past experience. LV % is the leak rate velocity percent and describes how increasing infection increases the amount of PSA over time by leaking higher percentages of PSA. LV % has two parts: the presence probability, P %, and the distribution of its values. P % is either 1 or 0 based on the P % draw in the L % module. P % is set equal to 100% for the certain module in the bold box. The distribution density function is likely to decline in density with increasing LV %. It may change based on past experience. An example for fPSA % is shown with the mean equal to Infection % times the ratio of healthy plus BPH free PSA to PSA. Typically, Infection % is much less than 100% because infection tends to decrease the amount of PSA leakage while decreasing free PSA % substantially. CV % may be relatively large.

Model Tuning

An enormous amount of data can be needed to define all the underlying distributions completely. In practice, the amount of data needed to define the distributions is not practical to obtain. Therefore, an iterative process is needed to tune the parameters of the underlying distributions so that known relationships are satisfied and the overall distributions conform to population studies.

Figure 58:
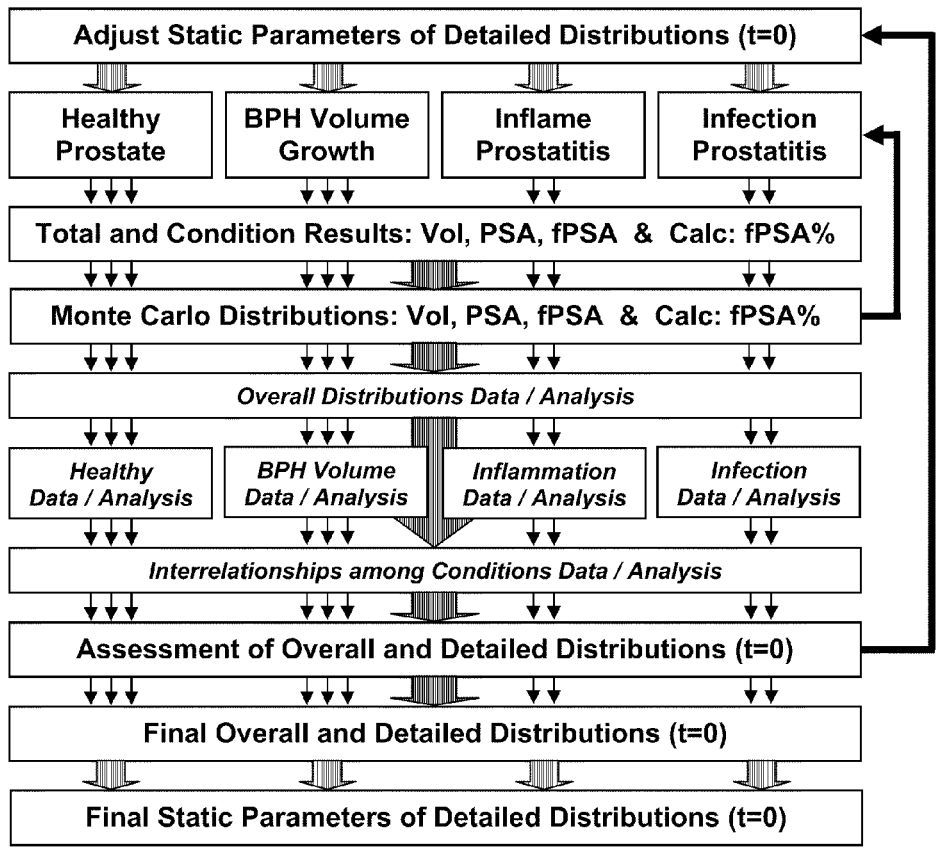
FIG. 58 shows exemplary tuning of parameters and validation of detailed distributions.

In an aspect, an iterative Monte Carlo process generates multi-dimensional distributions for men of a given age without prostate cancer. Static parts of the distribution (no velocities as shown below) can be validated against available distributions. For example, the Center for Disease Control has published distributions of PSA, free PSA and free PSA % for U.S. men in ten year age ranges from age forty to age eighty and above, and the Mayo Clinic has published prostate volume and PSA distributions for men from age forty to age eighty in Olmsted County, Minn. Distributions like these constrain the overall distributions generated by the Monte Carlo process. Details of these distributions and other medical studies constrain the results of the specific probability generators and the relationships among them. For example, the CDC distributions show a significant decline in free PSA % for higher levels of PSA. This result strongly suggests that infection prostatitis accounts for an increasing proportion of higher PSA results because it is the only benign condition that produces free PSA in a percent that is significantly lower than the other benign conditions. Exemplary tuning of parameters and validation of detailed distributions is demonstrated in as shown in FIG. 58.

Figure 57:
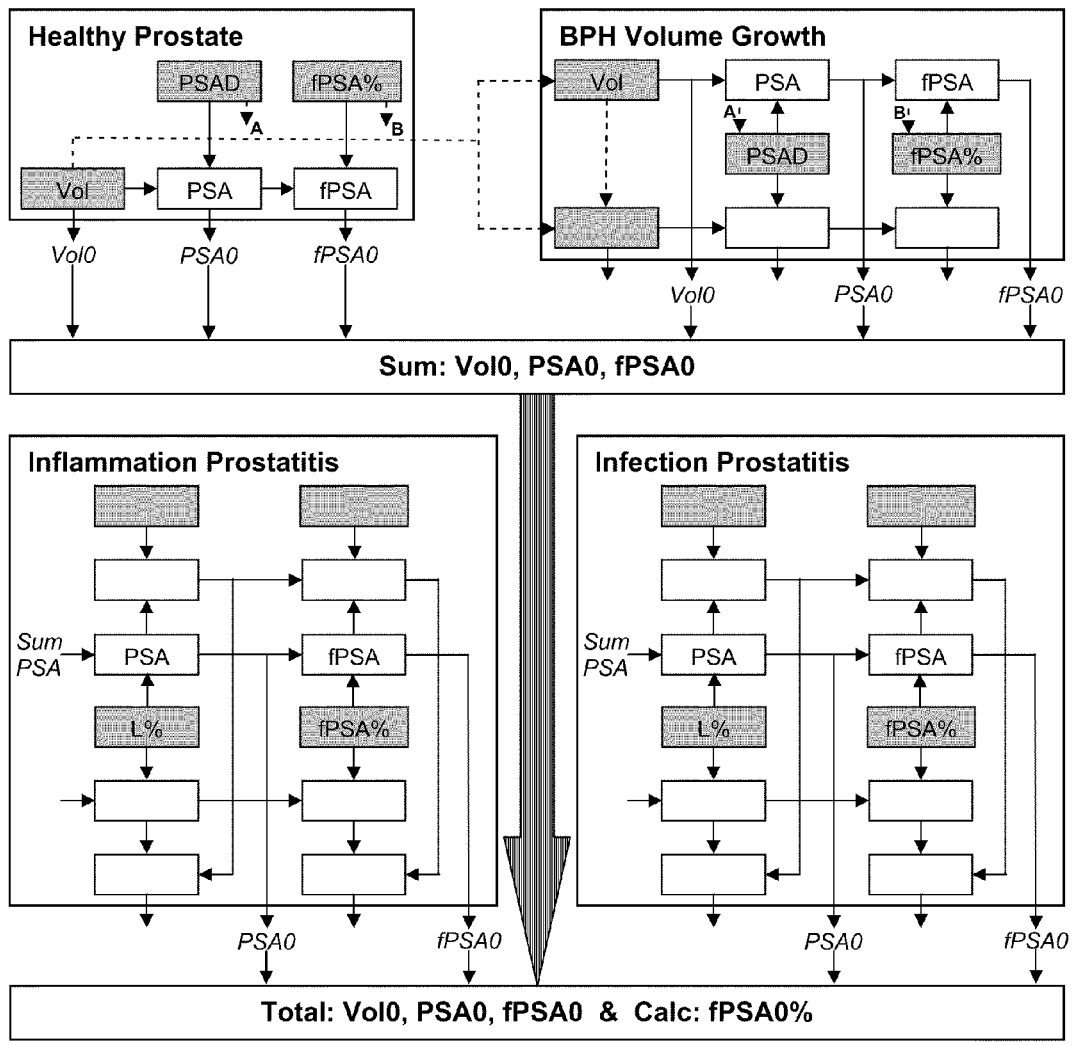
FIG. 57 shows an embodiment of a first step of a tuning process of the invention that is to tune the no cancer static distribution for a given age (t=0), such as age 55.

In an embodiment, the first step of a tuning process of the invention is to tune the no cancer static distribution for a given age (t=0), such as age 55. No velocities need be calculated for this static distribution as shown in FIG. 57. Unused modules are shown as blank in the figure. Starting parameters for all underlying distributions, the gray boxes, are chosen consistent with known relationships, and an iterative Monte Carlo process is run. The resulting multi-dimensional distribution is compared to the population distribution. New parameters for all underlying distributions are chosen consistent with known relationships, and an iterative Monte Carlo process is run again. The resulting multi-dimensional distribution is compared to the population distribution. Over many cycles through this process the multi-dimensional distribution converges on the population distribution while maintaining known relationships to the extent possible. Advanced solution algorithms may be used to speed the convergence process. This tuning process is repeated for a range of ages, such as age 45, 55, 65 and 75.

In another embodiment of a tuning process of the invention, the next step is to tune the velocity distribution parameters. Static results for a given year plus the changes caused by velocities accumulated over a ten year period should yield the static distribution ten years later. An iterative Monte Carlo process using static and velocity parameters generates multi-dimensional distributions for men ten years later without prostate cancer. Static parts of the distribution can be validated against available distributions. For example, the Center for Disease Control has published distributions of PSA, free PSA and free PSA % for U.S. men in ten year age ranges from age forty to age eighty and above, and the Mayo Clinic has published prostate volume and PSA distributions for men from age forty to age eighty in Olmsted County, Minn. Distributions like these constrain the overall distributions generated by the Monte Carlo process. Details of these distributions and other medical studies constrain the results of the specific probability generators and the relationships among them.

Figure 59:
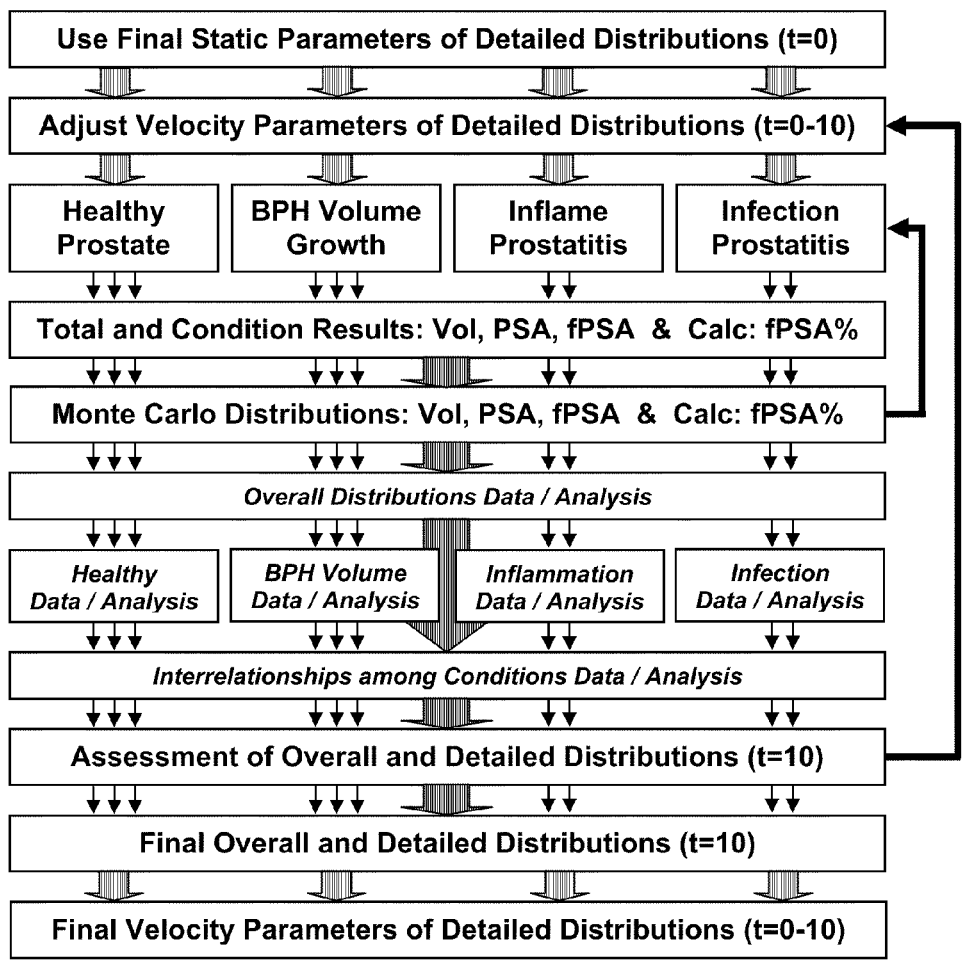
FIG. 59 and FIG. 60 show embodiments of a second step that is to tune velocity parameters to achieve the no cancer static distribution for ten years later (t=10), such as age 65.
Figure 60:
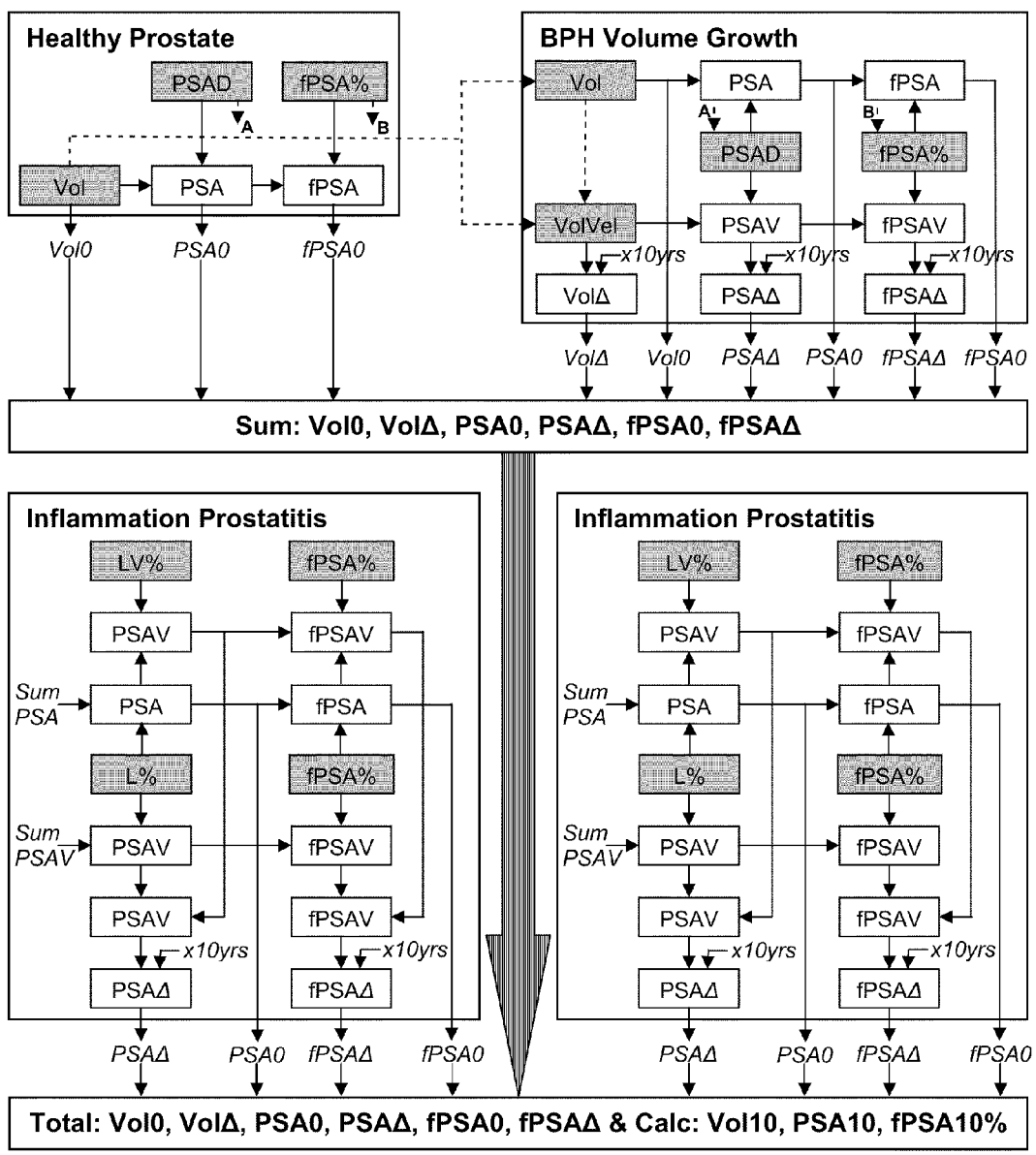

In another embodiment, a tuning process involves using the parameters for the no cancer static distribution for a given age (t=0), such as age 55. A second step is to tune velocity parameters to achieve the no cancer static distribution for ten years later (t=10), such as age 65 as shown in FIG. 59 and FIG. 60. Starting parameters for all underlying velocity distributions are chosen consistent with known relationships, and an iterative Monte Carlo process is run. The resulting multi-dimensional static distribution for ten years later is compared to the population distribution. New parameters for all underlying velocity distributions are chosen consistent with known relationships, and an iterative Monte Carlo process is run again. The resulting multi-dimensional static distribution is compared to the population distribution. Over many cycles through this process the multi-dimensional static distribution converges on the population distribution while maintaining known relationships to the extent possible. Advanced solution algorithms may be used to speed the convergence process. This tuning process is repeated for a range of ages.

Integrated Health Systems

In another aspect, a medical information system for assessing a disease of a subject is provided that comprises: an input device for receiving subject data; a processor that assesses a probability of said data relating to historical data; a storage unit in communication with the processor having a database for: (i) storing the subject data; (ii) storing historical data related to the disease; and an output device that transmits information relating to the probability of said data relating to historical data to an end user.

Also provided herein is a method for assessing a disease in a subject comprising: collecting data from the subject corresponding to a biomarker for the disease at least two different times, wherein the data corresponding to the at least two different times form a trend; exporting said data for manipulation of said data by executing a method herein; and importing the results of said manipulation to an end user. For example, data is collected at a first location, such as a hospital, the data is exported to a second location, such as a remote server in any remote location, where a method of the invention is executed to obtain information regarding the disease in a subject, and then the information is imported from the remote location back to the first location, such as the point-of-care in the hospital, or the information is imported to a third location, such as a database.

It is further noted that the systems and methods may be implemented on various types of computer architectures, such as for example on a networked system or in a client-server configuration, or in an application service provider configuration, on a single general purpose computer or workstation. The systems and methods may include data signals conveyed via networks (for example, local area network, wide area network, internet, combinations thereof), fiber optic medium, carrier waves, and wireless networks for communication with one or more data processing devices. The data signals can carry any or all of the data disclosed herein (for example, user input data, the results of the analysis to a user) that is provided to or from a device.

Additionally, the methods and systems described herein may be implemented on many different types of processing devices by program code comprising program instructions that are executable by the device processing subsystem. The software program instructions may include source code, object code, machine code, or any other stored data that is operable to cause a processing system to perform methods described herein.

The systems' and methods' data (for example, associations, mappings) may be stored and implemented in one or more different types of computer-implemented ways, such as different types of storage devices and programming constructs (for example, data stores, RAM, ROM, Flash memory, flat files, databases, programming data structures, programming variables, IF-THEN (or similar type) statement constructs). It is noted that data structures describe formats for use in organizing and storing data in databases, programs, memory, or other computer-readable media for use by a computer program.

The systems and methods may be provided on many different types of computer-readable media including computer storage mechanisms (for example, CD-ROM, diskette, RAM, flash memory, computer's hard drive, magnetic tape, and holographic storage) that contain instructions (for example, software) for use in execution by a processor to perform the methods' operations and implement the systems described herein.

The computer components, software modules, functions, data stores and data structures described herein may be connected directly or indirectly to each other in order to allow the flow of data needed for their operations. It is also noted that the meaning of the term module includes but is not limited to a unit of code that performs a software operation, and can be implemented for example as a subroutine unit of code, or as a software function unit of code, or as an object (as in an object-oriented paradigm), or as an applet, or in a computer script language, or as another type of computer code. The software components and/or functionality may be located on a single computer or distributed across multiple computers depending upon the situation at hand.

In yet another aspect, a computer readable medium is provided including computer readable instructions, wherein the computer readable instructions instruct a processor to execute step a) of the methods described above. The instructions can operate in a software runtime environment.

In yet another aspect, a data signal is provided that can be transmitted using a network, wherein the data signal includes said posterior probability calculated in a step of the methods described above. The data signal can further include packetized data that is transmitted through wired or wireless networks.

In an aspect, a computer readable medium comprises computer readable instructions, wherein the instructions when executed carry out a calculation of the probability of a medical condition in a patient based upon data obtained from the patient corresponding to at least one biomarker. The computer readable instructions can operate in a software runtime environment of the processor. In an embodiment, a software runtime environment provides commonly used functions and facilities required by the software package. Examples of a software runtime environment include, but are not limited to, computer operating systems, virtual machines or distributed operating systems. As will be appreciated by those of ordinary skill in the art, several other examples of runtime environment exist. The computer readable instructions can be packaged and marketed as a software product or part of a software package. For example, the instructions can be packaged with an assay kit for PSA.

The computer readable medium may be a storage unit. It is appreciated by those skilled in the art that computer readable medium can also be any available media that can be accessed by a server, a processor, or a computer. The computer readable medium can be incorporated as part of the computer-based system, and can be employed for a computer-based assessment of a medical condition.

In an embodiment, the calculation of a probability can be carried out on a computer system. The computer system can comprise any or all of the following: a processor, a storage unit, software, firmware, a network communication device, a display, a data input, and a data output. A computer system can be a server. A server can be a central server that communicates over a network to a plurality of input devices and/or a plurality of output devices. A server can comprise at least one storage unit, such as a hard drive or any other device for storing information to be accessed by a processor or external device, wherein the storage unit can comprise one or more databases. In an embodiment, a database can store hundreds to millions of data points corresponding to a biomarker from hundreds to millions of subjects. A storage unit can also store historical data read from an external database or as input by a user. In an embodiment, a storage unit stores data received from an input device that is communicating or has communicated with the server. A storage unit can comprise a plurality of databases. In an embodiment, each of a plurality of databases corresponds to each of a plurality of biomarkers. In another embodiment, each of a plurality of databases corresponds to each of a plurality of possible medical conditions of a subject. An individual database can also comprise information for a plurality of possible medical conditions or a plurality of biomarkers or both. Further, a computer system can comprise multiple servers.

A processor can access data from a storage unit or from an input device to perform a calculation of an output from the data. A processor can execute software or computer readable instructions as provided by a user, or provided by the computer system or server. The processor may have a means for receiving patient data directly from an input device, a means of storing the subject data in a storage unit, and a means for processing data. The processor may also include a means for receiving instructions from a user or a user interface. The processor may have memory, such as random access memory, as is well known in the art. In one embodiment, an output that is in communication with the processor is provided.

After performing a calculation, a processor can provide the output, such as from a calculation, back to, for example, the input device or storage unit, to another storage unit of the same or different computer system, or to an output device. Output from the processor can be displayed by data display. A data display can be a display screen (for example, a monitor or a screen on a digital device), a print-out, a data signal (for example, a packet), an alarm (for example, a flashing light or a sound), a graphical user interface (for example, a webpage), or a combination of any of the above. In an embodiment, an output is transmitted over a network (for example, a wireless network) to an output device. The output device can be used by a user to receive the output from the data-processing computer system. After an output has been received by a user, the user can determine a course of action, or can carry out a course of action, such as a medical treatment when the user is medical personnel. In an embodiment, an output device is the same device as the input device. Example output devices include, but are not limited to, a telephone, a wireless telephone, a mobile phone, a PDA, a flash memory drive, a light source, a sound generator, a fax machine, a computer, a computer monitor, a printer, an iPOD, and a webpage. The user station may be in communication with a printer or a display monitor to output the information processed by the server.

A client-server, relational database architecture can be used in embodiments of the invention. A client server architecture is a network architecture in which each computer or process on the network is either a client or a server. Server computers are typically powerful computers dedicated to managing disk drives (file servers), printers (print servers), or network traffic (network servers). Client computers include PCs (personal computers) or workstations on which users run applications, as well as example output devices as disclosed herein. Client computers rely on server computers for resources, such as files, devices, and even processing power. In some embodiments of the invention, the server computer handles all of the database functionality. The client computer can have software that handles all the front-end data management and can also receive data input from users.

A database can be developed for a medical condition in which relevant information is filtered or obtained over a communication network (for example, the internet) from one or more data sources, such as a public remote database, an internal remote database, and a local database. A public database can include online sources of free data for use by the general public, such as, for example, databases supplied by the U.S. Department of Health and Human Services. For example, an internal database can be a private internal database belonging to particular hospital, or a SMS (Shared Medical system) for providing data. A local database can comprise, for example, biomarker data relating to a medical condition. The local database may include data from a clinical trial. It may also include data such as blood test results, patient survey responses, or other items from patients in a hospital.

Subject data can be stored with a unique identifier for recognition by a processor or a user. In another step, the processor or user can conduct a search of stored data by selecting at least one criterion for particular patient data. The particular patient data can then be retrieved.

In an example, a subject or medical professional enters medical data from a biomarker assay into a webpage. The webpage transmits the data to a computer system or server, wherein the data is stored and processed. For example, the data can be stored in databases the computer systems. Processors in the computer systems can perform calculations comparing the input data to historical data from databases available to the computer systems. The computer systems can then store the output from the calculations in a database and/or communicate the output over a network to an output device, such as a webpage or email. After a user has received an output from the computer system, the user can take a course of medical action according to the output. For example, if the user is a physician and the output is a probability of cancer above a threshold value, the physician can then perform or order a biopsy of the suspected tissue.

Figure 61:
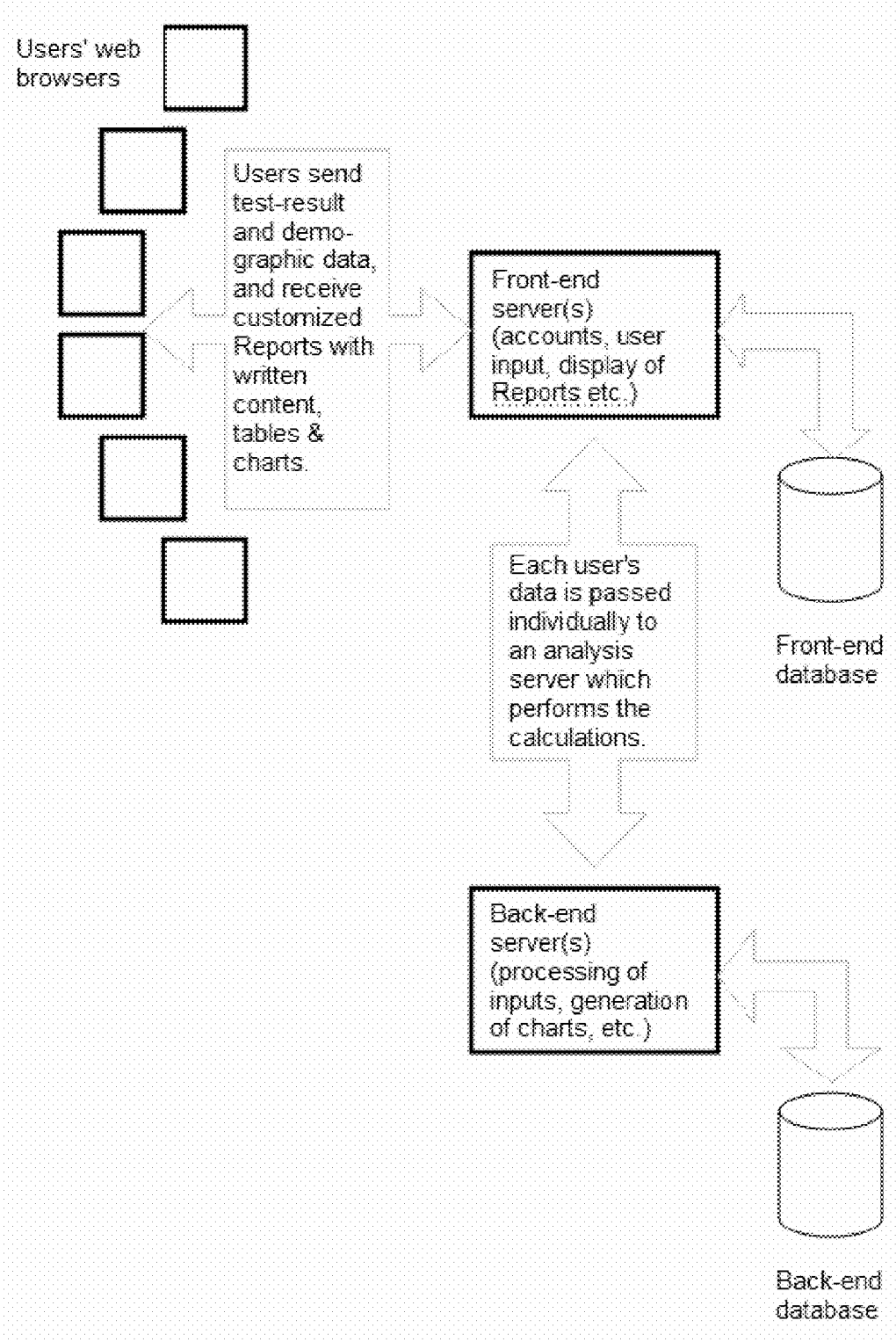
FIG. 61 illustrates an exemplary computer system of the invention comprising a plurality of graphical user interfaces, a front end server comprising databases, and a back end server capable of performing calculations of probabilities.

FIG. 61 demonstrates an example computer system of the invention. A set of users can use a web browser to enter data from a biomarker assay into a graphical user interface of a webpage. The webpage is a graphical user interface associated with a front end server, wherein the front end server can communicate with the user's input device (for example, a computer) and a back end server. The front end server can either comprise or be in communication with a storage device that has a front-end database capable of storing any type of data, for example user account information, user input, and reports to be output to a user. Data from each user (for example, biomarker values and subject profiles) can be then be sent to a back end server capable of manipulating the data to generate a result. For example, the back end server can calculate a probability that a subject has a medical condition using the data input by the user. A back end server can comprise historical data relating to a medical condition to be evaluated, or a plurality of medical conditions. The back end server can then send the result of the manipulation or calculation back to the front end server where it can be stored in a database or can be used to generate a report. The results can be transmitted from the front end server to an output device (for example, a computer with a web browser) to be delivered to a user. A different user can input the data and receive the data. In an embodiment, results are delivered in a report. In another embodiment, results are delivered directly to an output device that can alert a user.

In an embodiment, a method of the invention comprises obtaining a sample from a subject, wherein the sample contains a biomarker. The sample can be obtained by the subject or by a medical professional. Examples of medical professionals include, but are not limited to, physicians, emergency medical technicians, nurses, first responders, psychologists, medical physics personnel, nurse practitioners, surgeons, dentists, and any other obvious medical professional as would be known to one skilled in the art. The sample can be obtained from any bodily fluid, for example, amniotic fluid, aqueous humor, bile, lymph, breast milk, interstitial fluid, blood, blood plasma, cerumen (earwax), Cowper's fluid (pre-ejaculatory fluid), chyle, chyme, female ejaculate, menses, mucus, saliva, urine, vomit, tears, vaginal lubrication, sweat, serum, semen, sebum, pus, pleural fluid, cerebrospinal fluid, synovial fluid, intracellular fluid, and vitreous humour. In an example, the sample is obtained by a blood draw, where the medical professional draws blood from a subject, such as by a syringe. The bodily fluid can then be tested to determine the prevalence of the biomarker. Biological markers, also referred to herein as biomarkers, according to the present invention include without limitation drugs, prodrugs, pharmaceutical agents, drug metabolites, biomarkers such as expressed proteins and cell markers, antibodies, serum proteins, cholesterol, polysaccharides, nucleic acids, biological analytes, biomarker, gene, protein, or hormone, or any combination thereof. At a molecular level, the biomarkers can be polypeptide, glycoprotein, polysaccharide, lipid, nucleic acid, and a combination thereof.

Example biomarker assays include, but are not limited to, DNA assays, including DNA microarrays, Southern blots, Northern blots, ELISAs, flow cytometry, Western blots, PSA assays, and immunoassays. The information from the assay can be quantitative and sent to a computer system of the invention. The information can also be qualitative, such as observing patterns or fluorescence, which can be translated into a quantitative measure by a user or automatically by a reader or computer system. In an embodiment, the subject can also provide information other than biomarker assay information to a computer system, such as race, height, weight, age, gender, eye color, hair color, family medical history and any other information that may be useful to the user, as would be obvious.

Information can be sent to a computer system automatically by a device that reads or provides the data from a biomarker assay. In another embodiment, information is entered by a user (for example, the subject or medical professional) into a computer system using an input device. The input device can be a personal computer, a mobile phone or other wireless device, or can be the graphical user interface of a webpage. For example, a webpage programmed in JAVA can comprise different input boxes to which text can be added by a user, wherein the string input by the user is then sent to a computer system for processing. The subject may input data in a variety of ways, or using a variety of devices. Data may be automatically obtained and input into a computer from another computer or data entry system. Another method of inputting data to a database is using an input device such as a keyboard, touch screen, trackball, or a mouse for directly entering data into a database.

In another embodiment, a system can further include a medical test for testing said subject for said medical condition. The medical test can be a PSA assay. In yet another embodiment, a system can further include a medical treatment for treating said subject for said medical condition. The medical treatment can be selected from a group including the following: a pharmaceutical, surgery, organ resection, and radiation therapy.

In an embodiment, a computer system comprises a storage unit, a processor, and a network communication unit. For example, the computer system can be a personal computer, laptop computer, or a plurality of computers. The computer system can also be a server or a plurality of servers. Computer readable instructions, such as software or firmware, can be stored on a storage unit of the computer system. A storage unit can also comprise at least one database for storing and organizing information received and generated by the computer system. In an embodiment, a database comprises historical data, wherein the historical data can be automatically populated from another database or entered by a user.

In an embodiment, a processor of the computer system accesses at least one of the databases or receives information directly from an input device as a source of information to be processed. The processor can perform a calculation on the information source, for example, performing dynamic screening or a probability calculation method. After the calculation the processor can transmit the results to a database or directly to an output device. A database for receiving results can be the same as the input database or the historical database. An output device can communicate over a network with a computer system of the invention. The output device can be any device capable delivering processed results to a user. Example output devices include, but are not limited to, a telephone, a wireless telephone, a mobile phone, a PDA, a flash memory drive, a light source, a sound generator, a fax machine, a computer, a computer monitor, a printer, an iPOD, and a webpage.

An output of a computer system may assume any form, such as a computer program, webpage, or print-out. Any other suitable representation, picture, depiction or exemplification may be used.

Communication between devices or computer systems of the invention can be any method of digital communication including, for example, over the internet Network communication can be wireless, ethernet-based, fiber optic, or through fire-wire, USB, or any other connection capable of communication as would be obvious to one skilled in the art. In an embodiment, information transmitted by a system or method of the invention can be encrypted by any method as would be obvious to one skilled in the art. In the field of medicine, or diagnostics, encryption may be necessary to maintain privacy of the data, as well as deter theft of information.

It is further noted that the systems and methods may include data signals conveyed via networks (for example, local area network, wide area network, internet), fiber optic medium, carrier waves, wireless networks for communication with one or more data processing or storage devices. The data signals can carry any or all of the data disclosed herein that is provided to or from a device.

Additionally, the methods and systems described herein may be implemented on many different types of processing devices by program code comprising program instructions that are executable by the device processing subsystem. The software program instructions may include source code, object code, machine code, or any other stored data that is operable to cause a processing system to perform methods described herein. Other implementations may also be used, however, such as firmware or even appropriately designed hardware configured to carry out the methods and systems described herein.

The methods herein may be packaged as a computer program product, such as the expression of an organized set of instructions in the form of natural or programming language statements that is contained on a physical media of any nature (for example, written, electronic, magnetic, optical or otherwise) and that may be used with a computer or other automated data processing system of any nature (but preferably based on digital technology). Such programming language statements, when executed by a computer or data processing system, cause the computer system to act in accordance with the particular content of the statements. Computer program products include without limitation: programs in source and object code and/or test or data libraries embedded in a computer readable medium. Furthermore, the computer program product that enables a computer system or data processing equipment device to act in preselected ways may be provided in a number of forms, including, but not limited to, original source code, assembly code, object code, machine language, encrypted or compressed versions of the foregoing and any and all equivalents.

Information before, after, or during processing can be displayed on any graphical display interface in communication with a computer system (for example, a server). A computer system may be physically separate from the instrument used to obtain values from the subject. In an embodiment, a graphical user interface also may be remote from the computer system, for example, part of a wireless device in communication with the network. In another embodiment, the computer and the instrument are the same device.

An output device or input device of a computer system can include one or more user devices comprising a graphical user interface comprising interface elements such as buttons, pull down menus, scroll bars, fields for entering text, and the like as are routinely found in graphical user interfaces known in the art. Requests entered on a user interface are transmitted to an application program in the system (such as a Web application). In one embodiment, a user of user device in the system is able to directly access data using an HTML interface provided by Web browsers and Web server of the system.

A graphical user interface may be generated by a graphical user interface code as part of the operating system or server and can be used to input data and/or to display input data. The result of processed data can be displayed in the interface or a different interface, printed on a printer in communication with the system, saved in a memory device, and/or transmitted over a network. A user interface can refer to graphical, textual, or auditory information presented to a user and may also refer to the control sequences used for controlling a program or device, such as keystrokes, movements, or selections. In another example, a user interface may be a touch screen, monitor, keyboard, mouse, or any other item that allows a user to interact with a system of the invention as would be obvious to one skilled in the art.

In yet another aspect, a method of taking a course of medical action by a user is provided including initiating a course of medical action based on a posterior probability delivered from an output device to said user.

The course of medical action can be delivering medical treatment to said subject. The medical treatment can be selected from a group consisting of the following: a pharmaceutical, surgery, organ resection, and radiation therapy. The pharmaceutical can include, for example, a chemotherapeutic compound for cancer therapy. The course of medical action can include, for example, administration of medical tests, medical imaging of said subject, setting a specific time for delivering medical treatment, a biopsy, and a consultation with a medical professional.

The course of medical action can include, for example, repeating a method described above.

A method can further include diagnosing the medical condition of the subject by said user with said posterior probability from said output device.

A system or method can involve delivering a medical treatment or initiating a course of medical action. If a disease has been assessed or diagnosed by a method or system of the invention, a medical professional can evaluate the assessment or diagnosis and deliver a medical treatment according to his evaluation. Medical treatments can be any method or product meant to treat a disease or symptoms of the disease. In an embodiment, a system or method initiates a course of medical action. A course of medical action is often determined by a medical professional evaluating the results from a processor of a computer system of the invention. For example, a medical professional may receive output information that informs him that a subject has a 97% probability of having a particular medical condition. Based on this probability, the medical professional can choose the most appropriate course of medical action, such as biopsy, surgery, medical treatment, or no action. In an embodiment, a computer system of the invention can store a plurality of examples of courses of medical action in a database, wherein processed results can trigger the delivery of one or a plurality of the example courses of action to be output to a user. In an embodiment, a computer system outputs information and an example course of medical action. In another embodiment, the computer system can initiate an appropriate course of medical action. For example, based on the processed results, the computer system can communicate to a device that can deliver a pharmaceutical to a subject. In another example, the computer system can contact emergency personnel or a medical professional based on the results of the processing. Courses of medical action a patient can take include self-administering a drug, applying an ointment, altering work schedule, altering sleep schedule, resting, altering diet, removing a dressing, or scheduling an appointment and/or visiting a medical professional. A medical professional can be for example a physician, emergency medical personnel, a pharmacist, psychiatrist, psychologist, chiropractor, acupuncturist, dermatologist, urologist, proctologist, podiatrist, oncologist, gynecologist, neurologist, pathologist, pediatrician, radiologist, a dentist, endocrinologist, gastroenterologist, hematologist, nephrologist, ophthalmologist, physical therapist, nutritionist, physical therapist, or a surgeon.

Medical professionals may take medical action when alerted by the methods of the invention of the medical condition of a subject. Examples of an alert include, but are not limited to, a sound, a light, a printout, a readout, a display, an alarm, a buzzer, a page, an e-mail, a fax alert, telephonic communication, or a combination thereof. The alert may communicate to the user the raw subject data, the calculated probability of the subject data.

The medical action can be based on rules imposed by the medical professional or the computer system. Courses of medical action include, but are not limited to, surgery, radiation therapy, chemotherapy, prescribing a medication, evaluating mental state, delivering pharmaceuticals, monitoring or observation, biopsy, imaging, and performing assays and other diagnostic tests. In an embodiment, the course of medical action may be inaction. Medical action also includes, but is not limited to, ordering more tests performed on the patient, administering a therapeutic agent, altering the dosage of an administered therapeutic agent, terminating the administration of a therapeutic agent, combining therapies, administering an alternative therapy, placing the subject on a dialysis or heart and lung machine, performing computerized axial tomography (CAT or CT) scan, performing magnetic resonance imaging (MRI), performing a colonoscopy, administering a pain killer, prescribing a medication. In some embodiments, the subject may take medical action. For example, a diabetic subject may administer a dose of insulin.

Figure 62:
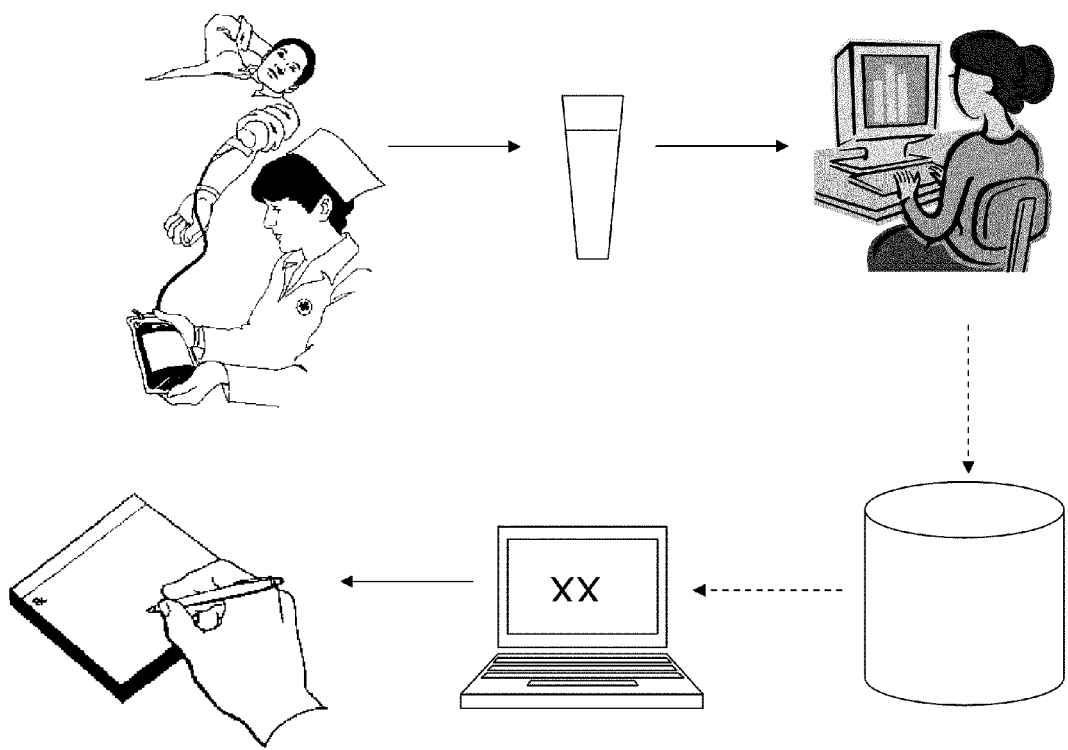
FIG. 62 illustrates an exemplary method of delivering a probability that a subject has a medical condition to a user and using the probability to take a course of medical action.

FIG. 62 illustrates a method of delivering a probability that a subject has a medical condition to a user and using the probability to take a course of medical action. A blood sample is drawn from a patient by a medical professional. In other embodiments, any method of obtaining a biomarker values from a subject may be used as would be obvious to one skilled in the art, such as swabs and urine tests. In FIG. 62, the sample is assayed for a biomarker and biomarker values are generated. As described herein, there may be many suitable methods for generating and obtaining biomarker values. The values can then input into a computer by a medical professional or other user, such as the subject or an assistant. The data can then be processed by a method of the invention to calculate the probability that a subject has the medical condition. An output is generated and delivered to a user on a computer monitor, for example, the output delivers the probability of a subject having a medical condition and is display on a personal computer or laptop of the subject's doctor. The output can also be delivered to the subject himself or to a different medical professional. In another embodiment, the output is delivered to a notification system, such as an alarm or another computer-based program. In FIG. 62, based on the output, a physician can take a medical action as described herein. In this example, the output initiates a medical professional writing a prescription.

Figure 63:
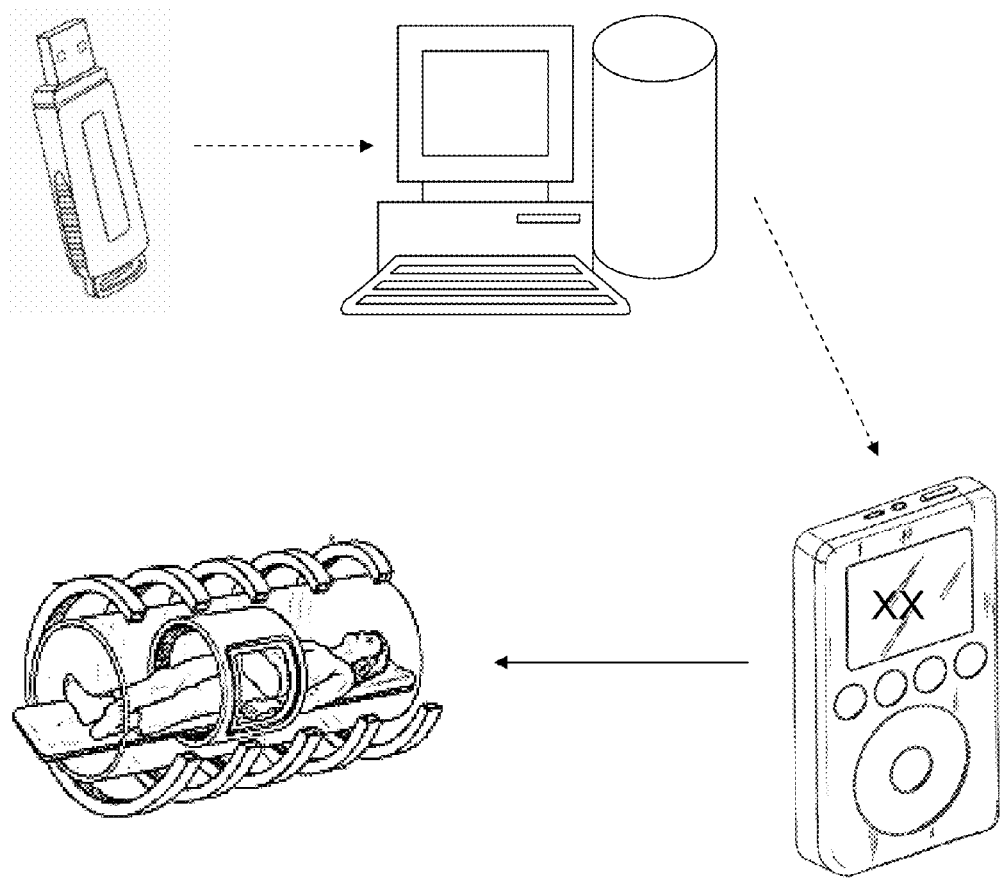
FIG. 63 and FIG. 64 illustrate exemplary courses of events related to a method or system of the invention.

FIG. 63 illustrates a course of events related to the invention. Data regarding a biomarker corresponding to a medical condition from a patient are stored on a USB flash drive storage device. Data are input into a computer system and data are processed by a calculation method of the invention. For example, the computer system can be a server that receives data from multiple input devices and can distribute results of a calculation method to a plurality of output devices. In the example in FIG. 63, the results of the calculation method are a probability that a patient has a medical condition. The results delivered to the output device can also be suggestions of courses of medical action, reports based on the biomarker data, or warning or notification of the status of the patient and/or calculation. FIG. 63 also demonstrates displaying a probability of the medical condition of the subject on an output device such as an iPOD. In this example, after reviewing the output, a user decides the course of medical action is a patient needs to obtain an MR image.

Figure 64:
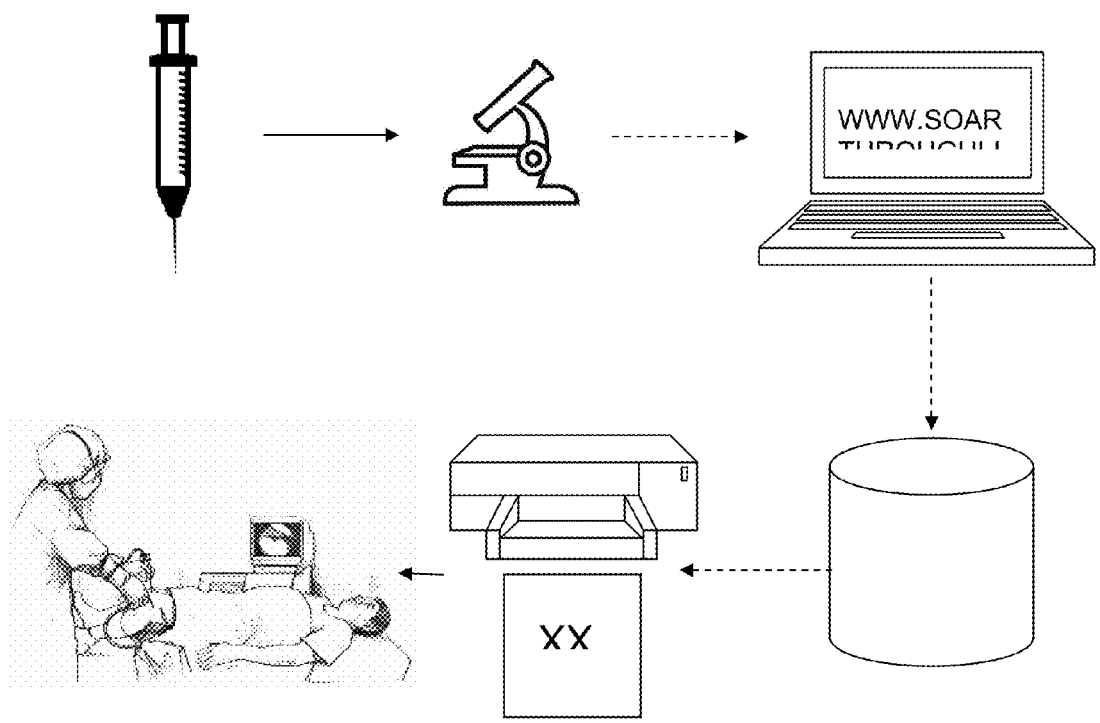

FIG. 64 illustrates another example practice of the invention. A sample is taken from a patient by a syringe and the sample is analyzed for a biomarker using a microscope to obtain a biomarker value corresponding to a medical condition. Using a graphical user interface, such as a website, a user can enter the results of the analysis into the graphical user interface, or input device. The result of the biomarker analysis is transmitted from an input device, such as a laptop computer and the biomarker values are processed using a calculation method the invention in a server of the invention. A probability of the subject from which the biomarker values were obtained is output to a printout from a printer to a user, such as the subject's physician. In this example, the physician may take a course of medical action that comprises delivering a medical treatment, such as performing an invasive surgical procedure, such as a biopsy, based on results of the calculation.

Business Methods

In another aspect, a business method is disclosed that comprises: receiving a first value of at least one biomarker of a subject; calculating a first plurality of posterior probabilities of the occurrence of a plurality of medical conditions of said subject with a computer system using said a first value; delivering said first plurality of posterior probabilities to a user; receiving a second value of at least one biomarker of a subject and a result of a course of medical action taken by said user based upon said delivery of said first plurality of posterior probabilities; calculating a second plurality of posterior probabilities of the occurrence of a plurality of medical conditions of said subject with said computer system using said a second value and said result of a course of the medical action; and delivering said second plurality of posterior probabilities to said user. In an embodiment, the first or second values are received from a user, such as a user selected from the group consisting of the following: a physician, a health care provider, a pharmacy, an insurance company, and the subject. A first or second value can also be received from said user through a webpage or an electronic device or an assay device.

In another embodiment, the first or second values are received from a device, such as a device selected from the group consisting of the following: a lab test device, a point-of-care assay device, a personal electronic device, an electronic medical record, and a computer system.

Calculating can be carried out by a Monte Carlo engine and can be a Bayesian statistical calculation.

In an embodiment, a plurality of medical conditions is at least four medical conditions, for example from the group consisting of: prostatitis due to inflammation, prostatitis due to infection, prostate cancer, benign prostate hyperplasia, and no prostate disease. A biomarker value can be from a PSA or fPSA assay.

A result of a course of medical action can be selected from the group consisting of the following: a test result, a diagnosis, a cure, an effect, and no effect. Posterior probabilities can be delivered to a user through an electronic medical record or a webpage or an electronic device with a display or a printout.

In an embodiment, the computer system comprises a processor, a storage unit, and a device for network communication.

In an embodiment, a business method is carried out for a fee, for example each delivery of posterior probabilities is carried out for a fee.

A business method can further comprise suggesting a course of medical action to said user based on said posterior probabilities, and the suggestion can be provided for a fee.

In an embodiment of a business method of the invention, a posterior probability of a medical condition is delivered to a user, wherein the user, without limitation, is a patient, a medical person (such as a physician), a health systems, or a lab. For example, a subject can have a blood test that is assayed in a lab or at the point-of-care and then a user sends the information from the assay to company (such as over the internet), where the company performs processes or calculations with the information and delivers an output (such as a probability of the occurrence of a disease) to the user. The company can provide the output for a fee.

In an embodiment, a business method comprises selling services of the calculations and delivery of information directly to patients. For example, the patients can use this information with their physicians.

In an embodiment, tokens can be sold to a user for a company to perform a calculation method the invention and delivery of the results of the calculation method to the user. For example, tokens can be sold singly or in blocks of more than one. Further, each token can allow the user to obtain one analysis as delivered by a business method of the invention.

In another embodiment, a user of a token is a physician, insurance company, or health system. In another embodiment of a method when a subject has a periodically scheduled test, the results of the tests and other patient information, including a history of biomarker results, can be entered or uploaded to a computer system and then the company can analyze the data and provide a report for use that includes probabilities for one or more medical conditions, for example a doctor reading the report with a patient.

A company can also use a method of the invention to sell services to testing labs. For example, a token method as described herein can be used. In an embodiment, labs may offer a package of services that include blood draws, biomarker analysis and analysis as provided by the invention.

In another embodiment, a company performs an analysis for insurance company reimbursement.

Digital health services, such as WebMD, may offer a calculation method of the invention as a value added service in conjunction with medical information and other analysis services.

As new technology is developed to deliver blood test results at the point of care within a short time, perhaps minutes, in an embodiment of the invention the device doing the test can communicate to a computer system wirelessly, through a docking station or other physical link or by other means, including manual entry of the results. The computer system can have software and/or a storage medium that receives the test results and other information about the patient and for performing a calculation method of the invention. A computer system can be on remote servers that can process the new data along with other patient information already stored in the system. Parallel processing can be used to analyze the data and create a report quickly, perhaps in minutes. A report can be transmitted to the computer in the doctor's office for viewing on screen or for printing and use as hard copy. For example, the doctor may review the report with the patient and decide on a course of medical action. For example, the doctor and patient may decide on ultrasound imaging to measure the volume of the patient's prostate. The prostate volume measured can be entered into a computer system for further analysis that can then create a new report that can be transmitted to the doctor's display for viewing or printing. For example, the doctor may review the new results with the patient and decide on a new course of medical action. For example, the doctor and patient may decide to culture prostate secretions for infection and start a course of antibiotics to treat the possible infection.

In another embodiment with new technology developed to deliver automated blood tests for a variety of biomarkers at one time, automated protein profile equipment reports the levels of a wide variety of proteins and other biomarkers in a sample. Biomarker values can be automatically uploaded to a computer system as described herein and can be added to other patient information already stored in the system. For example, new probabilities can be calculated for all medical conditions being considered. The doctor and/or the patient can consider the results and choose appropriate courses of medical action.

Individuals can vary in their predisposition for various conditions. In an embodiment, methods of the invention incorporate these predispositions or risk factors into the prior probabilities of each condition for each individual. For example, genetic testing might show a man has a three times higher than normal risk of prostate cancer. Family history or race might suggest other men have a two times higher than normal risk of prostate cancer. Several risk factors can be combined into an overall risk ratio that reflects a person increased or reduced risk of a condition compared to an overall population. Risk factors can include without limitation: gene profile, family history, race, obesity (BMI), physical condition, geographic location of home and work over time, diet and exercise regimen, exposure to environmental factors and other things.

An individual's future predisposition to various conditions can depend on their past incidence of that condition and other related conditions. In another embodiment, methods of the invention incorporate these predispositions or risk factors into either the prior probabilities of each condition for each individual or an explicit algorithm that may be a Bayes process. For example, a man with a history of prostatitis caused by infection has an increased risk of that condition in the future. If a prior probability is adjusted then algorithms are used to combine the risk factor based on past history with other risk factors into an overall risk ratio that reflects a person increased or reduced risk of a condition compared to an overall population. Alternatively, a different algorithm can be used to calculate a new posterior probability of a condition based on the details of the past history of that condition and related conditions, perhaps using a Bayes process.

It is to be understood that the exemplary methods and systems described herein may be implemented in various forms of hardware, software, firmware, special purpose processors, or a combination thereof. Preferably, a calculation method of the present invention is implemented in software as an application program tangibly embodied on one or more program storage devices. The application program may be executed by any machine, device, or platform comprising suitable architecture. It is to be further understood that, because some of the systems and methods depicted in the Figures are preferably implemented in software, the actual connections between the system components (or the process steps) may differ depending upon the manner in which the method is programmed. Given the teachings herein, one of ordinary skill in the related art will be able to contemplate or practice these and similar implementations or configurations of the present invention.

All the examples disclosed herein are to be considered non-limiting. As an illustration, it should be understood that for the processing flows described herein, the steps and the order of the steps may be altered, modified, removed, and/or augmented and still achieve the desired outcome.

What is claimed is:

1. A method of performing a course of medical action for a medical condition of a subject comprising:
   a) obtaining a first series of PSA values from a subject;
   b) performing a first dynamic analysis using a computer system, comprising:
      i) fitting said first series of PSA values to form a first fitted trend;
      ii) estimating a first characteristic of said first fitted trend, wherein said first characteristic is a first PSA velocity defined as a rate of change in trend PSA; iii) calculating one or more probabilities of the occurrence of one or more medical conditions of said subject using said first characteristic, wherein said one or more medical conditions comprises a prostate medical condition selected from the group consisting of the following: prostatitis due to inflammation prostatitis due to infection prostate cancer, benign prostate hyperplasia, and no prostate disease;
   c) determining if the results of said first dynamic analysis have reached a first threshold for medical action, wherein said threshold corresponds to a probability that the subject has a medical condition, wherein the probability is based on analysis of PSA velocity population data; and
   d) performing a first course of medical action for a first medical condition if said results of said first dynamic analysis reaches said threshold, wherein said first course of medical action is treatment with antibiotics and/or anti-inflammatory medication; measurement of prostate volume; continued PSA tests; a free PSA test; a proPSA test; a biopsy, medical imaging; or medical treatment for prostate cancer.

2. The method of claim 1, wherein said subject is a human.

3. The method of claim 1, wherein said computer system comprises a device for network communication, a storage unit, and a processor.

4. The method of claim 3, wherein said computer system comprises a Monte Carlo engine.

5. The method of claim 1, wherein said first dynamic analysis further comprises estimating a second characteristic of said first fitted trend, wherein said second characteristic is a first PSA variation.

6. The method of claim 5, further comprising:
e) obtaining a second series of PSA values from said subject, wherein at least one of said second series of PSA values is measured after performing said first course of medical action;
f) performing a second dynamic analysis on a computer system, comprising:
i) comparing said PSA value measured after performing said first course of medical action to said first series of PSA values and said first fitted trend;
ii) estimating a third characteristic of said second series of PSA values, wherein said characteristic is a second PSA velocity or a second PSA variation;
g) determining if the results of said second dynamic analysis have reached a second threshold for medical action, wherein said threshold is based on analysis of population data and the results of said first dynamic analysis; and
h) performing a second course of medical action for a second medical condition when the results of said second dynamic analysis reach said second threshold.

7. The method of claim 5, further comprising:
e) obtaining a second series of PSA values from said subject, wherein at least one of said second series of PSA values is measured after performing said first course of medical action;
f) performing a second dynamic analysis on a computer system, comprising:
i) fitting said second series of PSA values to form a second fitted trend;
ii) estimating a third characteristic of said second fitted trend, wherein said characteristic is a second PSA velocity or a second PSA variation;
g) obtaining the results of said first course of medical action;
h) determining if the results of said second dynamic analysis have reached a second threshold for medical action, wherein said second threshold is based on analysis of population data, the results of said first dynamic analysis, and the results of said first course of medical action; and
i) performing a second course of medical action for a second medical condition if the results of said second dynamic analysis reach said second threshold.

8. The method of claim 1, further comprising:
e) obtaining a second series of PSA values from said subject, wherein at least one of said second series of PSA values is measured after performing said first course of medical action;
f) performing a second dynamic analysis on a computer system, comprising:
i) comparing said PSA value measured after performing said first course of medical action to said first series of PSA values and said first fitted trend;
ii) estimating a second characteristic of said second series of PSA values, wherein said characteristic is a second PSA velocity or a PSA variation;
g) determining if the results of said second dynamic analysis have reached a second threshold for medical action, wherein said threshold is based on analysis of population data and the results of said first dynamic analysis; and
h) performing a second course of medical action for a second medical condition when the results of said second dynamic analysis reach said second threshold.

9. The method of claim 8, wherein said second characteristic is said second PSA velocity, and said second PSA velocity is calculated using a PSA test value obtained before said first course of medical action and said PSA test value measured after said first course of medical action.

10. The method of claim 8, wherein said second characteristic is said PSA variation.

11. The method of claim 8, wherein said first or second course of medical action is treatment with antibiotics and/or anti-inflammatory medication; measurement of prostate volume; continued PSA tests; a free PSA test; a proPSA test; a biopsy; medical imaging; or medical treatment for prostate cancer.

12. The method of claim 8, wherein said first or second threshold is further based on a personal characteristic of said subject, wherein said personal characteristic is selected from the group consisting of said subject's: age, demographics, life expectancy, Emotional Weights, family history, medical history, and expected side effects of treatment.

13. The method of claim 8, wherein said first or second threshold is calculated using Monte Carlo methods.

14. The method of claim 8, wherein Bayesian analysis is used in the process of determining if the results of said first or second dynamic analysis have reached said first or second threshold for medical action.

15. The method of claim 1, further comprising:
e) obtaining a second series of PSA values from said subject, wherein at least one of said second series of PSA values is measured after performing said first course of medical action;
f) performing a second dynamic analysis on a computer system, comprising:
i) fitting said second series of PSA values to form a second fitted trend;
ii) estimating a second characteristic of said second fitted trend, wherein said characteristic is a second PSA velocity or a PSA variation;
g) obtaining the results of said first course of medical action;
h) determining if the results of said second dynamic analysis have reached a second threshold for medical action, wherein said second threshold is based on analysis of population data, the results of said first dynamic analysis, and the results of said first course of medical action; and
i) performing a second course of medical action for a second medical condition if the results of said second dynamic analysis reach said second threshold.

16. The method of claim 15, wherein said second characteristic is said PSA variation.

17. The method of claim 15, wherein said first or second course of medical action is treatment with antibiotics and/or anti-inflammatory medication; measurement of prostate volume; continued PSA tests; a free PSA test; a proPSA test; a biopsy; medical imaging; or medical treatment for prostate cancer.

18. The method of claim 15, wherein said second medical condition is selected from the group consisting of: prostatitis due to inflammation, prostatitis due to infection, prostate cancer at various stages of progression, benign prostatic hyperplasia, and no prostate disease.

19. The method of claim 15, wherein said first and second medical conditions are the same.

20. The method of claim 15, wherein said first and second medical conditions are different.

21. The method of claim 15, wherein said first or second threshold is further based on a personal characteristic of said subject, wherein said personal characteristic is selected from the group consisting of said subject's: age, demographics, life expectancy, Emotional Weights, family history, medical history, and expected side effects of treatment.

22. The method of claim 15, wherein said first or second threshold is calculated using Monte Carlo methods.

23. The method of claim 15, wherein Bayesian analysis is used in the process of determining if the results of said first or second dynamic analysis have reached said first or second threshold for medical action.

24. The method of claim 1 or 15, wherein said fitting is to an exponential function.

25. The method of claim 1, 8, or 15, wherein said first or second threshold is further based on a personal characteristic of said subject, wherein said personal characteristic is selected from the group consisting of said subject's: age, demographics, life expectancy, Emotional Weights, family history, medical history, and expected side effects of treatment.

26. The method of claim 25, wherein said method comprises generating probability distributions based on Monte Carlo simulations that use a database of PSA values measured in a plurality of subjects.

27. The method of claim 26, wherein said method comprises generating probability distributions based on Monte Carlo simulations that use a database of PSA values measured in a plurality of subjects.

28. The method of claim 1, 8, or 15, wherein said first or second threshold is calculated using Monte Carlo methods.

29. The method of claim 1, 8, or 15, wherein Bayesian analysis is used in the process of determining if the results of said first or second dynamic analysis have reached said first or second threshold for medical action.

30. The method of claim 8 or 15, wherein said second medical condition is selected from the group consisting of: prostatitis due to inflammation, prostatitis due to infection, prostate cancer at various stages of progression, benign prostatic hyperplasia, and no prostate disease.

31. The method of claim 8 or 15, wherein said first and second medical conditions are the same.

32. The method of claim 8 or 15, wherein said first and second medical conditions are different.

33. A method comprising:
a. receiving a series of PSA values of a subject;
b. performing a dynamic analysis using a computer system, comprising:
   i) fitting said series of PSA values to form a fitted trend;
   ii) estimating a characteristic of said fitted trend, wherein said characteristic is a PSA velocity defined as a rate of change in trend PSA; iii) calculating one or more probabilities of the occurrence of one or more medical conditions of said subject using said first characteristic, wherein said one or more medical conditions comprises a prostate medical condition selected from the group consisting of the following: prostatitis due to inflammation, prostatitis due to infection, prostate cancer, benign prostate hyperplasia, and no prostate disease;
c. determining if the results of said dynamic analysis have reached a first threshold for medical action for a medical condition, wherein said threshold corresponds to a probability that the subject has a medical condition, wherein the probability is based on analysis of PSA velocity population data; and
d. delivering the results of said determining step to a user for use in selecting a course of medical action, wherein said course of medical action is treatment with antibiotics and/or anti-inflammatory medication; measurement of prostate volume; continued PSA tests; a free PSA test; a proPSA test; a biopsy, medical imaging; or medical treatment for prostate cancer.

34. The method of claim 33, wherein the series of PSA values are received from a user.

35. The method of claim 34, wherein the user is selected from the group consisting of the following: a physician, a health care provider, a pharmacy, an insurance company, and the subject.

36. The method of claim 34, wherein said series of PSA values is received from said user through a webpage.

37. The method of claim 34, wherein said series of PSA values is received from said user through an electronic device.

38. The method of claim 34, wherein said series of PSA values is received from said user through an assay device.

39. The method of claim 33, wherein the series of PSA values is received from a device.

40. The method of claim 39, wherein the device is selected from the group consisting of the following: a lab test device, a point-of-care assay device, a personal electronic device, an electronic medical record, and a computer system.

41. The method of claim 33, wherein said computer system comprises a Monte Carlo engine.

42. The method of claim 33, wherein the results of said determining step are delivered to a user through an electronic medical record.

43. The method of claim 33, wherein the results of said determining step are delivered to a user through a webpage.

44. The method of claim 33, wherein said the results of said determining step are delivered to a user through an electronic device with a display.

45. The method of claim 33, wherein the results of said determining step are delivered to a user through a printout.

46. The method of claim 33, wherein said computer system comprises a processor, a storage unit, and a device for network communication.

47. The method of claim 33, wherein the method is carried out for a fee.

48. The method of claim 47, wherein each delivery of the results of said determining step is carried out for a fee.

49. The method of claim 33 further comprising suggesting a course of medical action to said user based on said results of said determining step or the results of said dynamic analysis.

50. The method of claim 49, wherein said suggesting is provided for a fee.

* * * * *